US009669049B2

(12) United States Patent
Gruber et al.

(10) Patent No.: US 9,669,049 B2
(45) Date of Patent: Jun. 6, 2017

(54) COMPOSITIONS COMPRISING GAMMA RETROVIRUS VECTORS AND METHODS OF TREATING PROLIFERATIVE DISORDERS

(75) Inventors: Harry E. Gruber, Rancho Santa Fe, CA (US); Douglas J. Jolly, Encinitas, CA (US); Derek G. Ostertag, San Diego, CA (US); Ryan S. Burnett, San Diego, CA (US); Amy H. Lin, San Diego, CA (US); Tiffany Huang, San Diego, CA (US); Joan M. Robbins, San Diego, CA (US)

(73) Assignee: Tocagen Inc., San Diego, CA (US)

( * ) Notice: Subject to any disclaimer, the term of this patent is extended or adjusted under 35 U.S.C. 154(b) by 456 days.

(21) Appl. No.: 13/882,487

(22) PCT Filed: Oct. 31, 2011

(86) PCT No.: PCT/US2011/058595
§ 371 (c)(1),
(2), (4) Date: Aug. 20, 2013

(87) PCT Pub. No.: WO2012/058673
PCT Pub. Date: May 3, 2012

(65) Prior Publication Data
US 2013/0323301 A1    Dec. 5, 2013

Related U.S. Application Data

(60) Provisional application No. 61/408,623, filed on Oct. 31, 2010, provisional application No. 61/408,625, filed on Oct. 31, 2010, provisional application No. 61/408,875, filed on Nov. 1, 2010, provisional application No. 61/415,532, filed on Nov. 19, 2010.

(51) Int. Cl.
| | |
|---|---|
| *A61K 31/56* | (2006.01) |
| *A61K 31/58* | (2006.01) |
| *A61K 31/573* | (2006.01) |
| *A61K 31/713* | (2006.01) |
| *A61K 31/7088* | (2006.01) |
| *A61K 39/21* | (2006.01) |
| *A61K 39/395* | (2006.01) |
| *C12N 15/867* | (2006.01) |
| *A61K 35/768* | (2015.01) |
| *A61K 9/127* | (2006.01) |
| *A61N 5/10* | (2006.01) |

(52) U.S. Cl.
CPC .......... *A61K 31/7088* (2013.01); *A61K 9/127* (2013.01); *A61K 31/56* (2013.01); *A61K 31/573* (2013.01); *A61K 31/58* (2013.01); *A61K 31/713* (2013.01); *A61K 35/768* (2013.01); *A61K 39/21* (2013.01); *A61K 39/3955* (2013.01); *A61K 39/39558* (2013.01); *A61N 5/10* (2013.01); *C12N 15/867* (2013.01); *C12N 2740/13032* (2013.01)

(58) Field of Classification Search
CPC ...... A61K 31/56; A61K 31/573; A61K 31/58; A61K 31/7088; A61K 31/713; A61K 39/21; A61K 39/3955; A61K 2300/00; C61K 31/768; C12N 15/86; C12N 2740/10011
See application file for complete search history.

(56) References Cited

U.S. PATENT DOCUMENTS

| | | | |
|---|---|---|---|
| 6,033,905 | A | 3/2000 | Eiden et al. |
| 6,117,681 | A | 9/2000 | Salmons et al. |
| 6,303,380 | B1 | 10/2001 | Lin et al. |
| 6,410,313 | B1 | 6/2002 | Kasahara et al. |
| 6,448,390 | B1 | 9/2002 | Albritton et al. |
| 6,451,304 | B1 | 9/2002 | Friedmann et al. |
| 6,576,463 | B1 | 6/2003 | Kasahara et al. |
| 6,806,080 | B2 | 10/2004 | Kasahara et al. |
| 6,899,871 | B2 | 5/2005 | Kasahara et al. |
| 6,953,688 | B2 | 10/2005 | Ferrick et al. |
| 7,056,730 | B2 | 6/2006 | Pedersen et al. |
| 2002/0068362 | A1 | 6/2002 | Murray et al. |
| 2002/0137889 | A1 | 9/2002 | Soong et al. |

(Continued)

FOREIGN PATENT DOCUMENTS

| | | |
|---|---|---|
| WO | 9920742 A2 | 4/1999 |
| WO | 9936561 A1 | 7/1999 |

(Continued)

OTHER PUBLICATIONS

Pao, et al. Use of avian retroviral vectors to introduce transcriptional regulators into mammalian cells for analyses of tumor maintenance, PNAS, 100(15):8764-8769 (2003).*
Brown, B.D. et al. In vivo administration of lentiviral vectors triggers a type I interferon response that restricts hepatocyte gene transfer and promotes vector clearance. Blood, 109:2797-2805 (2007).*
Kasahara, N. "Viroreplicative Gene Therapy Targeted to Prostate Cancer", U.S. Army Medical Research and Material Command, Grant No. W81XWH-08-1, 0510, covering Aug. 1, 2008 to Jul. 21, 2010), published Aug. 2010.*
Solodushko V, et al. Dexamethasone and mifepristone increase retroviral infectivity through different mechanisms. Am. J. Physiol. Lung Cell Mol. Physiol., 2009, vol. 297, p. L538-L545.*

(Continued)

*Primary Examiner* — Robert Landsman
*Assistant Examiner* — Bruce D Hissong
(74) *Attorney, Agent, or Firm* — Gavrilovich, Dodd & Lindsey LLP

(57) ABSTRACT

This disclosure relates to replication competent viral vectors for treating cell proliferative disorders. The disclosure further relates to the use of such replication competent viral vectors for delivery and expression of a heterologous nucleic acid in normal and diseased tissues and methods and compositions that facilitate such delivery and expression to tissues in vivo and in vitro. The disclosure further relates to replication competent retroviral vectors for these uses and in conjunction with methods and compositions that facilitate in vivo therapeutics.

27 Claims, 18 Drawing Sheets

(56) References Cited

U.S. PATENT DOCUMENTS

| | | |
|---|---|---|
| 2003/0003565 A1 | 1/2003 | Dubensky |
| 2003/0157070 A1 | 8/2003 | Jolly |
| 2003/0157718 A1 | 8/2003 | Pedersen et al. |
| 2003/0165466 A1 | 9/2003 | Gromeier et al. |
| 2003/0219410 A1 | 11/2003 | Calatrava |
| 2004/0068762 A1 | 4/2004 | Attar et al. |
| 2004/0096972 A1 | 5/2004 | Audit et al. |
| 2004/0142449 A1 | 7/2004 | Tonjes et al. |
| 2004/0146489 A1 | 7/2004 | Yu et al. |
| 2004/0197308 A1 | 10/2004 | Takahashi et al. |
| 2004/0248827 A1 | 12/2004 | Zheng et al. |
| 2005/0002903 A1 | 1/2005 | Kasahara et al. |
| 2005/0059004 A1 | 3/2005 | Atabekov et al. |
| 2007/0003522 A1 | 1/2007 | Albritton |
| 2007/0254357 A1 | 11/2007 | Gregory et al. |
| 2008/0008685 A1 | 1/2008 | Kasahara |
| 2008/0227736 A1 | 9/2008 | Chen et al. |
| 2009/0169580 A1 | 7/2009 | Whelan et al. |
| 2012/0052554 A1 | 3/2012 | Kasahara et al. |

FOREIGN PATENT DOCUMENTS

| | | |
|---|---|---|
| WO | 014266 A1 | 1/2001 |
| WO | 2006127980 A2 | 11/2006 |
| WO | 2007095201 A2 | 8/2007 |
| WO | 2007107156 A2 | 9/2007 |
| WO | 2008151633 A2 | 12/2008 |
| WO | 2010002937 A1 | 1/2010 |
| WO | 2010036986 A2 | 4/2010 |
| WO | 2010045002 A2 | 4/2010 |
| WO | 2011126864 A2 | 10/2011 |
| WO | 2012021794 A1 | 2/2012 |

OTHER PUBLICATIONS

Attar, et al. "New transgenic non-human mammal expression a reporter nucleic acid under the regulation of androgen response elements, useful as models for identifying and developing selective androgen receptor modulators for treating cancer", Score Results to Attar et al, downloaded Jan. 13, 2013.*

Friedmann et al., "Producing replication-incompetent retrovirus vectors, by transfecting cells with a provirus plasmid that encodes gag, a proviruss plasmid that encodes pol, and an envelope protein encoding construct", Score Result to Friedmann et al, downloaded Jan. 14, 2013.*

Thompson, M.R. et al. Pattern recognition receptors and the innate immune response to viral infection. Viruses, 2011, vol. 3, p. 920-940.*

Roscigno et al., "A mutational analysis of the polypyrimidine tract of introns. Effects of sequence differences in pyrimidine tracts on splicing," J. Biol. Chem. 268:11222-11229 (1993).

Saavedra et al., "The simian retrovirus-1 constitutive transport element, unlike the HIV-1 RRE, uses factors required for cellular mRNA export," Curr. Biol. 7:619-628 (1997).

Sanders, D. A. "No false start for novel pseudotyped vectors," Curr. Opin. Biotechnol. 13, 437-442 (2002).

Segall et al., "Characterization and Detection of Artificial Replication-Competent Lentivirus of Altered Host Range," Molecular Therapy 8:118-129 (2003).

Shikova-Lekova et al. "Replication-competent hybrids between murine leukemia virus and foamy virus," J. Virol. 77, 7677-7681 (2003).

Shin et al., "Replication of lengthened Moloney murine leukemia virus genomes is impaired at multiple stages," J. Virol. 74:2694-2702 (2000).

Short et al., "Correlation of leukemogenic potential of murine retroviruses with transcriptional tissue preference of the viral long terminal repeats," J. Virol. 61:1067-1072 (1987).

Sliva et al., "Stable integration of a functional shRNA expression cassette into the murine leukemia virus genome," Virology 351(1):218-225 (2006).

Sodroski et al., "Repetitive structure in the long-terminal-repeat element of a type II human T-cell leukemia virus," Proc. Natl. Acad. Sci. USA 81:4617-4621. 1984.

Soifer et al., "A Novel, Helper-Dependent, Adenovirus-Retrovirus Hybrid Vector: Stable Transduction by a Two-Stage Mechanism," Molecular Therapy 5(5):599-608 (2002).

Solly et al., "Replicative retroviral vectors for cancer gene therapy," Cancer Gene Ther. 10:30-39 (2003).

Staffa et al., Identification of positive and negative splicing regulatory elements within the terminal tat-rev exon of human immunodeficiency virus type 1. Mol. Cell Biol. 15:4597-4605 (1995).

Stuhlmann et al., "Construction and properties of replication-competent murine retroviral vectors encoding methotrexate resistance," Mol. Cell. Biol. 9:100-108 (1989).

Subramanian et al., "Temperature-sensitive replication-competent adenovirus shRNA vectors to study cellular genes in virus-induced apoptosis," Methods in Molecular Medicine 130:125-134 (2007).

Sun et al., "Chronic gene delivery of interferon-inducible protein 10 through replication competent retrovirus vectors suppresses tumor growth," Cancer Gene Ther. 12:900-912 (2005).

Svarovskaia et al., Retroviral mutation rates and reverse transcriptase fidelity, Front. Biosci. 8:d117-d134 (2003).

Swanstrom et al., "Synthesis, assembly, and processing of viral proteins," In Retroviruses (Coffin, J. M., Hughes, S. H. & Varmus, H., eds), pp. 263-334, (1997). Cold Spring Harbor Laboratory Press, Plainview, NY.

Tai et al., "Antibody-Mediated Targeting of Replication-Competent Retroviral Vectors," Human Gene Therapy 14:789-802 (2003).

Tai et al., "Single-Shot, Multicycle Suicide Gene Therapy by Replication-Competent Retrovirus Vectors Achieves Long-Term Survival Benefit in Experimental Glioma," Molecular Therapy 12(5):842-851 (2005).

Tai et al., "Replication-competent retrovirus vectors for cancer gene therapy," Frontiers in Bioscience 13:3083-95 (2008).

Takeuchi et al., "Type C retrovirus inactivation by human complement is determined by both the viral genome and the producer cell," J. Virol. 68: 8001-8007 (1994).

Trubetskoy et al., "R region sequences in the long terminal repeat of a murine retrovirus specifically increase expression of unspliced RNAs," J. Virol. 73:3477-3483 (1999).

Valsamakis et al., The human immunodeficiency virus type 1 polyadenylylation signal: a 3' long terminal repeat element upstream of the AAUAAA necessary for efficient polyadenylylation, Proc. Natl. Acad. Sci. USA 88:2108-2112 (1991).

Van Santen et al., "mRNA precursor splicing in vivo: sequence requirements determined by deletion analysis of an intervening sequence," Proc. Natl Acad. Sci. USA 82:2885-2889 (1985).

Wang et al., "Highly Efficient and Tumor-Restricted Gene Transfer to Malignant Gliomas by Replication-Competent Retroviral Vectors," Human Gene Therapy 14:117-127 (2003).

Wang et al., "A murine leukemia virus with Cre-LoxP excisible coding sequences allowing superinfection, transgene delivery, and generation of host genomic deletions," Retrovirology 1(5) (2004).

Warmann et al., "Adenovirus-mediated cytosine deaminase/5-fluorocytosine suicide gene therapy of human hepatoblastoma in vitro," Pediatric Blood & Cancer, 53: 145-151 (2009).

Xie et al., "Adenovirus-mediated tissue-targeted expression of a caspase-9-based artificial death switch for the treatment of prostate cancer," Cancer Res. 61:6795-6804 (2001).

Xie et al., "Enhanced Retinal Ganglion Cell Differentiation by ath5 and NSCL1 Coexpression," IOVS 45(9):2922-2928 (2004).

Yamashita et al., "The cell cycle independence of HIV infections is not determined by known karyophilic viral elements," PLoS Pathog. 1:e18 (2005).

Yap et al., "Trim5alpha protein restricts both HIV-1 and murine leukemia virus," Proc. Natl. Acad. Sci. USA 101:10786-10791 (2004).

Yi, et al., "Retroviral gene therapy: safety issues and possible solutions," Curr. Gene Ther. 5:25-35 (2005).

Yin et al., "Insertion of sequences into the 3' untranslated region of a replication-competent spleen necrosis virus vector disrupts env gene expression," Arch Virol (1999) 144:73-87.

(56) References Cited

OTHER PUBLICATIONS

Young et al., "Chimeric Retroviral Helper Virus and Picornavirus IRES Sequence To Eliminate DNA Methylation for Improved Retroviral Packaging Cells," J. Virol. 74(11):5242-5249 (2000).
Young, Lee W. International Search Report and Written Opinion. International Application No. PCT/US2009/049322. Date of mailing: Sep. 2, 2009.
Altaner et al., "Prodrug cancer gene therapy," Cancer Letters, 2008, vol. 270, No. 2, pp. 191-201.
Fulci et al., "Cyclophosphamide enhances glioma virotherapy by inhibiting innate immune responses," PNAS, 2006, vol. 103, No. 34, pp. 12873-12878.
Hee, Choi Sung, International Search Report and Written Opinion, Korean Intellectual Property Office, PCT/US2011/058595, May 24, 2012.
Saito et al., "Oncolytic virotherapy for oral squamous cell carcinoma using replication-competent viruses," Oral Oncology, 2009, Vo.. 45, No. 12, pp. 1021-1027.
Sterman et al., "A pilot study of systemic corticosteroid administration in conjunction with intrapleural adenoviral vector administration in patients with malignant pleural mesothelioma," Cancer Gene Therapy, 2000, vol. 7, No. 12, pp. 1511-1518.
Tai et al., "Single-shot, multicycle suicide gene therapy by replication-competent retrovirus vectors achieves long-term survival benefit in experimental glioma," Molecular Therapy, 2005, vol. 12, No. 5, pp. 842-851.
Wang et al., "Use of replication-competent retroviral vectors in an immunocompetent intracranial glioma model," Neurosurg. Focus, 2006, vol. 20, No. 4, E25.
Becamel, Philippe, International Preliminary Report on Patentability and Written Opinion, PCT/US2013/058595, The International Bureau of WIPO, May 10, 2013.
Aagaard et al., "Fv1-like restriction of N-tropic replication-competent murine leukaemia viruses in mCAT-1-expressing human cells," Journal of General Virology 83:439-442 (2002).
Addison et al., "Comparison of the human versus murine cytomegalovirus immediate early gene promoters for transgene expression by adenoviral vectors," J. Gen. Virol. 78:1653-1661 (1997).
Akbulut et al., "Cytotoxic effect of replication-competent adenoviral vectors carrying L-plastin promoter regulated E1A and cytosine deaminase genes in cancers of the breast, ovary, and colon," Cancer Gene Therapy 10:388-395 (2003).
Akbulut et al., "Vector targeting makes 5-fluorouracil chemotherapy less toxic and more effective in animal models of epithelial neoplasms," 10(22):7738-46 (2004).
Ambrose et al., "In vitro characterization of a simian immunodeficiency virus human immunodeficiency virus (HIV) chimera expressing HIV type 1 reverse transcriptase to study antiviral resistance in pigtail macaques," J. Virol. 78:13553-13561 (2004).
Anello et al., "Adenovirus Mediated Cytosine Deaminase Gene Transduction and 5-fluorocytosine Therapy Sensitizes Mouse Prostate Cancer to Irradiation," The Journal of Urology 164(6):2173-2177 (2005).
Arrigo et al., "Regulation of Rous sarcoma virus RNA splicing and stability," Mol. Cell Biol. 8:4858-4867 (1988).
Bachrach et al., "Efficient Gene Transfer into Spleen Cells of Newborn Mice by a Replication-Competent Retroviral Vector," 293(2):328-334 (2002).
Bachrach et al., "In Vivo Infection of Mice by Replication-Competent MLV-Based Retrovirus Vectors," Methods in Molecular Medicine 76:343-352 (2003).
Baranick et al., "Splicing mediates the activity of four putative cellular internal ribosome entry sites," PNAS 105 (12):4733-4738 (2008).
Barsov et al., "Adaptation of chimeric retroviruses in vitro and in vivo: isolation of avian retroviral vectors with extended host range," J. Virol. 75:4973-4983 (2001).

Beijer, Gijsbertus. International Preliminary Report on Patentability. International Application No. PCT/US2009/058510. Date of mailing: Apr. 7, 2011.
Beijer, Gijsbertus. International Preliminary Report on Patentability. International Application No. PCT/US2009/058512. Date of Mailing: Apr. 7, 2011.
Blackburn et al., "Adenovrial transduction of a cytosine deaminase/thymidine kinase fusion gene into prostate carcinoma cells enhances prodrug and radiation sensitivity," International Journal of Cancer 82(2):293-297 (1999).
Bourbeau et al., "Suicide gene therapy with an adenovirus expressing the fusion gene CD::UPRT in human glioblastomas: different sensitivities correlate with p53 status," The Journal of Gene Medicine 6:1320-1332 (2004).
Bourbeau et al., "Improvement of antitumor activity by gene amplification with a replicating but nondisseminating adenovirus," 67(7):3387-95 (2007).
Bunnell et al., "Transplantation of transduced nonhuman primate CD34+ cells using a gibbon ape leukemia virus vector: restricted expression of the gibbon ape leukemia virus receptor to a subset of CD34+ cells," Gene Ther. 6:4856 (1999).
Chang et al., "A Replication-Competent Feline Leukemia Virus, Subgroup A (FELV-A), Tagged with Green Fluorescent Protein Reporter Exhibits in Vitro Biological Properties Similar to Those of the Parental FelV-A," Journal of Virology 75(18):8837-8841 (2001).
Cherry et al., "Retroviral Expression in Embryonic Stem Cells and Hematopoietic Stem Cells," Molecular and Cellular Biology 20(20):7419-7426 (2000).
Chio, Jun Ho. International Search Report and Written Opinion. International Application No. PCT/US2009/058510. Date of mailing of the International Search Report Jul. 6, 2010.
Cho, Jeong Han. International Search Report and Written Opinion. International Application No. PCT/US2009/058512. Date of mailing of the Report: May 11, 2011.
Coulombe et al., "A replication-competent promoter-trap retrovirus," J. Virol. 70:6810-6815 (1996).
Cupelli et al., "Transcriptional initiation and postinitiation effects of murine leukemia virus long terminal repeat R-region sequences," J. Virol. 65:6961-6968 (1991).
Cupelli et al., "The secondary structure of the R region of a murine leukemia virus is important for stimulation of long terminal repeat-driven gene expression," J. Virol. 72:7807-7814 (1998).
Delassus et al., "Genetic organization of gibbon ape leukemia virus," Virology 173:205-213 (1989).
Delviks, Krista Anda., "Development of murine leukemia virus-based vectors for more effective gene therapy: genetic analysis of direct repeat deletions," Dissertation, West Virginia (1999).
Dias et al., "Targeted chemotherapy for head and neck cancer with a chimeric oncolytic adenovirus coding for bifunctional suicide protein FCU1," Clin. Cancer Res. 16(9):2540-9; Epub Apr. 13, 2010.
Diaz et al., "Exchange of viral promoter/enhancer elements with heterologous regulatory sequences generates targeted hybrid long terminal repeat vectors for gene therapy of melanoma," J. Virol. 72:789-795 (1998).
Dillon et al., "Construction of a replication competent murine retrovirus vector expressing the human immunodeficiency virus type 1 Tat transactivator protein," J. Virol. 65:4490-4493 (1991).
Donahue et al., "Helper virus induced T cell lymphoma in nonhuman primates after retroviral mediated gene transfer," J. Expt. Med. 176:1125-1135 (1992).
Duch et al., "Transgene stability for three replication-competent murine leukemia virus vectors," Gene 329:61-69 (2004).
Edelstein et al., "Gene therapy clinical trials worldwide 1989-2004—an overview," J. Gene Med. 6:597-602 (2004).
Erbs et al., "In Vivo Cancer Gene Therapy by Adenovirus-mediated Transfer of a Bifunctional Yeast Cystosine Deaminase/Uracil Phosphoribosyltransferase Fusion Gene," Cancer Research 60(14):3813-3822 (2000).
Erbs et al. "Modified vaccinia virus Ankara as a vector for suicide gene therapy," Cancer Gene Ther. 15(1):18-28 (2008); Epub Nov. 9, 2007.

(56) References Cited

OTHER PUBLICATIONS

Erlwein et al., "The proline-rich region of the ecotropic Moloney murine leukaemia virus envelope protein tolerates the insertion of the green fluorescent protein and allows the generation of replication-competent virus," J. Gen. Virol. 84:369-373 (2003).
Ernst et al., "A structured retroviral RNA element that mediates nucleocytoplasmic export of intron containing RNA," Mol. Cell Biol. 17:135-144. (1997).
Evans et al., "A neutralizable epitope common to the envelope glycoproteins of ecotropic, polytropic, xenotropic, and amphotropic murine leukemia viruses," J. Virol. 64: 6176-6183 (1990).
Finger et al., "Replicating retroviral vectors mediating continuous production and secretion of therapeutic gene products from cancer cells," Cancer Gene Ther. 12:464-474 (2005).
Fischer et al., "Mechanisms of thymidine kinase/ganciclovir and cytosine deaminase/5-fluorocytosine suicide gene therapy-induced cell death in glioma cells," Oncogene 24:1231-1243 (2005).
Foloppe et al., "Targeted delivery of a suicide gene to human colorectal tumors by a conditionally replicating vaccinia virus," Gene Ther. 15(20):1361-71 (2008); Epub May 15, 2008.
Freytag et al., "Phase I Study of Replication-competent Adenovirus-mediated Double Suicide Gene Therapy for the Treatment of Locally Recurrent Prostate Cancer," Cancer Res. 62:4968 (2002).
Garton et al., "Efficient Expression of Exogenous Genes in Primary Vascular Cells Using IRES-Based Retroviral Vectors," Biotechniques 32:830-843 (2002).
Giffo-Schmitt, Beate. International Preliminary Report on Patentability. International Application No. PCT/US2009/049322. Date of Issuance of Report: Jan. 5, 2011.
Guffey et al., "Engineered herpes simplex virus expressing bacterial cytosine deaminase for experimental therapy for brain tumors," Cancer Gene Therapy 14(1):45-56 (2007); Epub Sep. 22, 2006.
Hacein-Bey-Abina et al., "LMO2-associated clonal T cell proliferation intwo patients after gene therapy for SCID-X1," Science 302:415-419 (2003).
Hiavaty et al., "Effects of sequences of prokaryotic origin on titer and transgene expression in retroviral vectors," Virology 330:351-360 (2004).
Hiraoka et al., "Tumor-Selective Gene Expression in a Hepatic Metastasis Model after Locoregional Delivery of a Replication-Competent Retrovirus Vector," Clin. Cancer Res. 12(23):7108-7116 (2006).
Hiraoka et al., "Therapeutic Efficacy of Replication-Competent Retrovirus Vector-Mediated Suicide Gene Therapy in a Multifocal Colorectal Cancer Metastasis Model," Cancer Research 67(11):5345-5353 (2007).
Hirschowitz et al., "In vivo adenovirus-mediated gene transfer of the *Escherichia coli* cytosine deaminase gene to human colon carcinoma-derived tumors induces chemosensitivity to 5-fluorocytosine," Hum. Gene Ther. 6(8):1055-63 (1995).
Horn et al., "Highly efficient gene transfer into baboon marrow repopulating cells using GALV-pseudotype oncoretroviral vectors produced by human packaging cells," Blood 100:3960-3967 (2002).
Heo, Joo Hyung, International Search Report and Written Opinion, PCT/US2013/066709, Korean Intellectual Property Office, Date of Mailing: Jan. 28, 2014.
Huber et al., "Metabolism of 5-fluorocytosine to 5-fluorouracil in human colorectal tumor cells transduced with the cytosine deaminase gene: significant antitumor effects when only a small percentage of tumor cells express cytosine deaminase," PNAS 91(17):8302-8306 (1994).
Hughes, Stephen H., "The RCAS Vector System," Folia Biologica (Praha) 50(3-4):107019 (2004).
Jespersen et al., "Epression of hterologous genes from an IRES translational cassette in replication competent murine leukemia virus vectors," Gene 239(2):227-235 (1999).
Johann et al., "Definition of a domain of GLVR1 which is necessary for infection by gibbon ape leukemia virus and which is highly polymorphic between species," J. Virol. 67:6733-6736 (1993).

Kaliberov et al., "Mutation of *Escherichia coli* cytosine deaminase significantly enhances molecular chemotherapy of human glioma," Gene Ther. 14(14):1111-9; Epub May 10,2007.
Kaliberova et al., "Molecular chemotherapy of pancreatic cancer using novel mutant bacterial cytosine deaminase gene," 7(9):2845-54 (2008).
Kawasaki et al., "Replication-competent retrovirus vector-mediated prodrug activator gene therapy in experimental models of human malignant mesothelioma," Cancer Gene Therapy 18:571-578 (2011).
Kikuchi et al., "Highly Efficient Gene Delivery for Bladder Cancers by Intravesically Administered Replication-Competent Retroviral Vectors," Clin. Cancer Res. 13:4511-4518 (2007).
Klein et al., "Rapid identification of viable retrovirus-transduced cells using the green fluorescent protein as a marker," Gene Ther. 4:1256-1260 (1997).
Kornblihtt et al., "Multiple links between transcription and splicing," RNA 10:1489-1498 (2004).
Kurozumi et al., "Apotosis Induction With 5-Fluorocytosine/Cytosine Deaminase gene therapy for Human Malignant Glioma Cells Mediated by Adenovirus," Journal of Neuro-Oncology 66(1-2):117-127 (2004).
Lazo et al., "Splice acceptor site for the env message of Moloney murine leukemia virus," J. Virol. 61:2038-2041 (1987).
Lipinski et al., "Optimization of a synthetic beta-catenin-dependent promoter for tumor-specific cancer gene therapy," Mol. Ther. 10:150-161 (2004).
Liu et al., "Tumor-specific therapeutic effect induced by an oncolytic adenoviral vector containing heat shock protein 70 and prodrug activation genes," 13(16):1235-43; Epub Apr. 13, 2006.
Liu et al. "Engineering conditionally replication-competent adenoviral vectors carrying the cytosine deaminase gene increase the infectivity and therapeutic effect for breast cancer gene therapy," 13(4):346-56 (2006).
Liu et al., "The receptors for gibbon ape leukemia virus and amphotropic murine leukemia virus are not downregulated in productively infected cells," Retrovirology 8:53 (2011).
Logg et al., "A Uniquely Stable Replication-Competent Retrovirus Vector Achieves Efficient Gene Delivery in Vitro and in Solid Tumors," Human Gene Therapy 12:921-932 (2001).
Logg et al., "Genomic Stability of Murine Leukemia Viruses Containing Insertions at the Env-3' Untranslated Region Boundary," Journal of Virology 75(15):6989-6998 (2001).
Logg et al., "Tissue-Specific Transcriptional Targeting of a Replication-Competent Retroviral Vector," Journal of Virology 76(24):12783-12791 (2002).
Logg et al., "Retrovirus-Mediated Gene Transfer to Tumors," Methods in Molecular Biology 246:499-525 (2004).
Lu et al., "Highly efficient gene transfer to solid tumors in vivo by tumor-selective replicating retrovirus vectors," Int. J. Mol. Med. 25(5):769-75 (2010).
Maguire, Simon. Examination Report. New Zealand Application No. 592070. Date of Report: May 24, 2011.
Malim et al., "The HIV-1 rev trans-activator acts through a structured target sequence to activate nuclear export of unspliced viral mRNA," Nature 338:254-257 (1989).
Marzio et al., "In vitro evolution of a highly replicating, doxycycline-dependent HIV for applications in vaccine studies," Proc. Natl Acad. Sci. USA 98:6342-6347 (2001).
Metzl et al., "Tissue- and Tumor-Specific Targeting of Murine Leukemia Virus-Based Replication-Competent Retroviral Vectors," Journal of Virology 80(14):7070-7078 (2006).
Mild et al., "Frequent intrapatient recombination between human immunodeficiency virus type 1 R5 and X4 envelopes: implications for coreceptor switch," J. Virol. 81:3369-3376 (2007).
Miller et al., "Gene transfer by retrovirus vectors occurs only in cells that are actively replicating at the time of infection," Mol. Cell. Biol. 10:4239-4242 (1990).
Miller et al., "Construction and properties of retrovirus packaging cells based on gibbon ape leukemia virus," J. Virol. 65:2220-2224 (1991).

(56) References Cited

OTHER PUBLICATIONS

Miller et al., "Intratumurol 5-Fluorouracil Produced by Cytosine Deaminase/5-Fluorocytosine Gene Therapy Is Effective for Experimental Human Glioblastomas," Cancer Res. 62:773 (2002).

Morgan et al., "Retroviral vectors containing putative internal ribosome entry sites: development of a polycistronic gene transfer system and applications to human gene therapy," Nucleic Acids Research 20(6):1293-1299 (1992).

Mullen et al., "Transfer of the bacterial gene for cytosine deaminase to mammalian cells confers lethal sensitivity to 5-fluorocytosine: a negative selection system," PNAS 89(1):33-37 (1992).

Mukesh et al., "High and Selective Expression of Yeast Cytosine Deaminase Under a Carcinoembryonic Antigen Promoter-Enhancer," Cancer Res. 62:2337-2342 (2002).

Murakami et al., "High-level expression of exogenous genes by replication-competent retrovirus vectors with an internal ribosomal entry site," Gene 202:23-29 (1997).

Nack et al., "Replacement of the murine leukemia virus (MLV) envelope gene with a truncated HIV envelope gene in MLV generates a virus with impaired replication capacity," Virology 315:209-216 (2003).

Nakamura et al., "Multimodality Therapy with a Replication-conditional Herpes Simplex Virus 1 Mutant that Expresses Yeast Cytosine Deaminase for intratumoral Conversion of 5-Fluorocytosine to 5-Fluorouracil," Cancer Res. 61:5447-5452 (2001); Epub Jul. 1, 2001.

Naldini et al., "Efficient transfer, integration, and sustained long-term expression of the transgene in adult rat brains injected with a lentiviral vector," Proc. Natl. Acad. Sci. USA 93:11382-11388 (1996).

Negroni et al., "Treatment of colon cancer cells using the cytosine deaminase/5-fluorocytosine suicide system induces apotosis, modulation of the proteome, and Hsp90B phsophorylation," Molecular Cancer Therapeutics 6:2747-2756 (2007).

Nogues et al., "Transcriptional activators differ in their abilities to control alternative splicing," J. Biol. Chem. 277:43110-43114 (2002).

O'Reilly et al., "Second-site changes affect viability of amphotropic/ecotropic chimeric enveloped murine leukemia viruses," J. Virol. 74:899-913 (2000).

Overbaugh et al., "Receptors and entry cofactors for retroviruses include single and multiple transmembrane-spanning proteins as well as newly described glycophosphatidylinositol-anchored and secreted proteins," Microbiol. Mol. Biol. Rev. 65:371-389 (2001).

Owens et al., "Human and simian immunodeficiency virus capsid proteins are major viral determinants of early, postentry replication blocks in simian cells," J. Virol. 77:726-731 (2003).

Paar et al., "Effects of Viral Strain, Transgene Position, and Target Cell Type on Replication Kinetics, Genomic Stability and Transgene Expression of Replication-Competent Murine Leukemia Virus-Based Vectors," Journal of Virology 81(13):6973-6983 (2007).

Paar et al., "Influence of vector design and host cell on the mechanism of recombination and emergence of mutant subpopulations of replicating retroviral vectors," BMC Molecular Biology 10(8) (2009).

Paola et al., "Suicide Gene Therapy With the Yeast Fusion Gene Cytosine Deaminase/Uracil Phosphoribosyltransferase is Not Enough for Pancreatic Cancer," Pancreas 35(3):224-231 (2007).

Poon et al. "Nucleocapsid and matrix protein contributions to selective human immunodeficiency virus type 1 genomic RNA packaging," J. Virol. 72:1983-1993 (1998).

Qiao et al. "VSV-G pseudotyped, MuLV-based, semi-replication-competent retrovirus for cancer treatment. Gene Ther," 13:1457-1470 (2006).

Rainov et al., "Clinical trials with retrovirus mediated gene therapy—what have we learned?," J. Neurooncol. 65:227—236 (2003).

Reik et al., Replication-competent Moloney murine leukemia virus carrying a bacterial suppressor tRNA gene: selective cloning of proviral and flanking host sequences. Proc. Natl. Acad. Sci. USA 82:1141-1145 (1985).

Robson et al., "Selection of optimal polypurine tract region sequences during Moloney murine leukemia virus replication," J. Virol. 74:10293-10303 (2000).

Ferrick et al., "Vector for screening for modulators of IgE synthesis, secretion and switch rearrangement", Score Result to Ferrick, Oct. 11, 2005.

Kasahara et al., "Viral Vectors", Three different score results to Kasahara et al. (2008).

Marvich, Maria, Notice of Allowance issued in U.S. Appl. No. 13/072,705, United States Patent and Trademark Office, Feb. 18, 2014.

Klee, Barbara, Office Action, Application No. 11837255.6, European Patent Office, Feb. 8, 2017.

Lun, Xuequing et al., "Myxoma Virus Virotherapy for Glioma in Immunocompetent Animal Models: Optimizing Administration Routes and Synergy with Rapamycin", Cancer Research, vol. 70, No. 2, Jan. 2010, pp. 598-608.

Otsuki Akihiro et al., "Histone deacetylase inhibitors augment antitumor efficacy of herpes-based oncolytic viruses", Molecular Therapy: The Journal of the American Society of Gene Therapy, vol. 16, No. 9, Sep. 2008, pp. 1546-1555.

Solly, Sounkary K. et al., "Replicative retrovial vectors for cancer gene therapy", Cancer Gene Therapy, vol. 10, No. 1, Jan. 1, 2003, pp. 30-39.

Touchefeu Y et al., "Review article: gene therapy, recent developments and future prospects in gastrointestinal oncology", Alimentary Pharmacology & Therapeutics, vol. 32, No. 8, Aug. 15, 2010, pp. 953-968.

* cited by examiner

COMPOSITIONS COMPRISING GAMMA RETROVIRUS VECTORS AND METHODS OF TREATING PROLIFERATIVE DISORDERS

CROSS REFERENCE TO RELATED APPLICATIONS

This application is a U.S. National Phase Application filed under 35 U.S.C. §371 and claims priority to International Application No. PCT/US2011/058595, filed Oct. 31, 2011, which application claims priority to U.S. Provisional Application Ser. No. 61/408,623, filed Oct. 31, 2010; 61/408,625, filed Oct. 31, 2010; 61/408,875, filed Nov. 1, 2010; and 61/415,532, filed Nov. 19, 2010, the disclosures of which are incorporated herein by reference.

TECHNICAL FIELD

This disclosure relates to replication competent viral vectors for treating cell proliferative disorders. The disclosure further relates to the use of such replication competent viral vectors for delivery and expression of a heterologous nucleic acid in normal and diseased tissues and methods and compositions that facilitate such delivery and expression to tissues in vivo and in vitro. The disclosure further relates to replication competent retroviral vectors for these uses and in conjunction with methods and compositions that facilitate in vivo therapeutics.

BACKGROUND

Non-replicating viruses and viral vectors were originally proposed 20 years ago as anticancer agents using modalities that are ablative (e.g. prodrug activation such as thymidine kinase plus gancyclovir), restorative of normal cellular function (e.g., p53), immune activating (e.g., IL-2) or some combination of these (see, for example, Crofts and Krimsky Hum Gene Ther. 16:169-177, 2005). However, it has become apparent that non-replicative vectors are very inefficient in delivering genes to whole animals or patients as injection into tissues does not allow transduction past areas close to the needle track (see, e.g., Lang et al., J Clin Oncol 21:2508-2518, 2003) and injection into the vasculature or other body fluids makes the individual particles very susceptible to various arms of the immune system such as complement and pre-existing adaptive immunity (see, e.g., Liu et al., Hum Gene Ther. 20:621-629, 2009).

Therefore in the past few years there has been a revival of interest in the use of replicative viruses and replicative viral vectors as disease fighting agents in general, and anti-cancer agents in particular. With the advent of chemotherapy, radiation treatment and modern surgical techniques, enthusiasm for this approach lagged and for several decades these three approaches, along with the more recent addition of active immunotherapy with monoclonal antibodies, have been the major modes of treatment. However, the limitations of these four approaches on overall cancer mortality have become more and more apparent, and led first to the attempts at therapy with non-replicative viral vectors, and more recently, replicative vectors with and without additional genes. The hope has been that the viruses would replicate through tumors and destroy them directly or by expression of a transgene. Currently replicative viruses or viral vectors based on adenovirus, herpes virus, vesicular stomatitis virus, reovirus, vaccinia virus, measles virus, alpha virus and others are being investigated (Stanford et al., Cytokine Growth Factor Rev., 21:177-83, 2010).

However, even after the advances over the last half century in the understanding of viruses and their interaction with their target cells, this effort has been largely frustrated by some of the same factors as before. In particular it has become apparent that most viruses that infect and lyse target cells as they replicate tend to engender rapid adaptive and inflammatory immune responses that lead to: rapid clearance of the hopefully therapeutic agent; continued tumor growth; and an inability to effectively re-administer (Choicca, Curr. Opin. Mol. Ther., 10:38-45, 2008). In addition there is often infection of non-diseased tissue. In reaction to these issues attempts have been made to selectively attenuate the viruses, use non-virulent strains (such as vaccine strains) and implant some tissue specificity in the viruses, such as by putting genes with key replicative functions in the virus under the control of tissue specific promoters or responsive to the tumor environment. Such attempts have had, at best, limited success in large part because of limited understanding of the host viral interactions.

SUMMARY

The disclosure provides methods and compositions for treating a cell proliferative disorder comprising administering a replication competent virus preparation to a subject, in combination with an agent that inhibits one or more of the pattern recognition receptors (PARPS) or their signaling pathways; a steroid; an anti-progestin agent; and/or radiation.

The disclosure provides a method of treating a cell proliferative disease or disorder comprising administering or contacting a subject in need of such treatment with (i) an inhibitor of a PRR or a IFN signaling pathway; (ii) a steroid, (iii) radiation, (iv) an anti-progestin agent (or any combination of (i)-(iv)) prior to, concurrently with or subsequent to administration of a recombinant replicative virus or viral vector. In one embodiment, the recombinant replicative virus or viral vector is a recombinant replicative gamma-retrovirus or recombinant replicative gamma-retrovirus vector. In another embodiment, the inhibitor of PRR or IFN signaling is administered at the same time as administration of the recombinant replicative virus or viral vector. In yet another embodiment, the inhibitor of PRR or IFN signaling is administered within a period of one day before to 2 days after administration of the recombinant replicative virus or viral vector. In any of the foregoing embodiments, the inhibitor of IFN signaling is an anti-IFN antibody or anti-IFN receptor antibody. In another embodiment, the recombinant replicative virus comprises a polynucleotide that expressed a polypeptide having cytosine deaminase activity. In yet another embodiment, when the vector comprises a polynucleotide that expresses a polypeptide having cytosine deaminase activity, the method further comprises administering 5-fluorocytosine to the subject wherein the 5-FC is converted to 5-FU and irradiating the subject. In another embodiment, the steroid is selected from the group consisting of prednisone, prednisolone, fluticasone, dexamethasone, budesonide, or a salt thereof. In yet another embodiment, the anti-progestin agent mifepristone. In one embodiment, the steroid is administered prior to, simultaneously with, following or throughout administration of a recombinant replication competent retrovirus. In another embodiment, the method further comprising measuring FBAL levels in a sample from the subject to determine therapeutic expression of cytosine deaminase activity. In a further embodiment, the sample is plasma or urine. In yet a further embodiment, the method further comprising adjusting a therapeutic dose of 5-FC or the recombinant replication competent retrovirus in response to FBAL levels. In any of the foregoing embodiments, the recombinant retroviral vector is administered intravenously.

The disclosure also provides a method of treating a cell proliferative disease or disorder comprising administering a recombinant replication competent retrovirus to a subject with the cell proliferative disease or disorder, wherein the replicative virus is not native to the subject species, and co-administering an inhibitor of PRR or IFN signaling pathways. In any of the foregoing embodiments of the disclosure, the PRR or IFN pathway inhibitor is selected from the group of agents set forth in Table 3. In yet a further embodiment, further comprising administering a steroid. In another embodiment, the recombinant replication competent retrovirus comprises a polynucleotide encoding a polypeptide having cytosine deaminase activity. In yet a further embodiment, the subject is administered 5-FC. In yet a further embodiment, following administration of 5-FC the subject undergoes radiation therapy while FBAL levels are at a therapeutic level that causes increased radiosensitization at a site of tumors that converts 5-FC to 5-FU.

The disclosure also provides a composition comprising an inhibitor of a PRR or an IFN signaling pathway and a recombinant replication competent retrovirus or viral vector.

The disclosure also provides a composition comprising a steroid and a recombinant replication competent retrovirus.

In any of the embodiments of the disclosure the recombinant replication competent retrovirus or viral vector can comprise: a retroviral GAG protein; a retroviral POL protein; a retroviral envelope; a retroviral polynucleotide comprising Long-Terminal Repeat (LTR) sequences at the 3' end of the retroviral polynucleotide sequence, a promoter sequence at the 5' end of the retroviral polynucleotide, said promoter being suitable for expression in a mammalian cell, a gag nucleic acid domain, a pol nucleic acid domain and an env nucleic acid domain; a cassette comprising an internal ribosome entry site (IRES) operably linked to a heterologous polynucleotide, wherein the cassette is positioned 5' to the 3' LTR and 3' to the env nucleic acid domain encoding the retroviral envelope; and cis-acting sequences necessary for reverse transcription, packaging and integration in a target cell, wherein the RCR maintains higher replication competency after 6 passages compared to a vector comprising SEQ ID NO: 4 (pACE). In further embodiments, the retroviral polynucleotide sequence is derived from murine leukemia virus (MLV), Moloney murine leukemia virus (MoMLV), Feline leukemia virus (FeLV) or Gibbon ape leukemia virus (GALV). In yet a further embodiment, the MLV is an amphotropic MLV. In any of the foregoing embodiments, the cell proliferative disease or disorder is a neoplastic disease or disorder. In a further embodiment, the cell proliferative disorder is selected from the group consisting of lung cancer, colon-rectum cancer, breast cancer, prostate cancer, urinary tract cancer, uterine cancer, brain cancer, head and neck cancer, pancreatic cancer, melanoma, stomach cancer and ovarian cancer, rheumatoid arthritis or other autoimmune disease. In specific embodiment, a recombinant retroviral vector of the disclosure comprises a sequence as set forth in SEQ ID NO:1, 2 or 3.

The disclosure also provide use of a composition comprising (i) an inhibitor of a PRR or a IFN signaling pathway; (ii) a steroid, (iii) radiation, or (iv) an anti-progestin agent in combination a recombinant replicative virus or viral vector comprising a heterologous polynucleotide for treating a cell proliferative disorder or disease.

The disclosure also provides a composition comprising a member selected from the group consisting of (i) an inhibitor of a PRR or a IFN signaling pathway; (ii) a steroid, (iii) radiation, (iv) an anti-progestin agent or any combination of (i)-(iv) in combination a recombinant replicative virus or viral vector comprising a heterologous polynucleotide for treating a cell proliferative disorder or disease.

Also disclosed are methods and compositions for treating a cell proliferative disorder comprising administering a replication competent virus preparation to a subject, in combination with an agent that inhibits one or more of the Toll-like receptors and their signaling pathway. Also provided are methods and compositions for treating a cell proliferative disorder comprising administering a replication competent virus preparation to a subject in combination with an agent that inhibits one or more component of the alpha and beta IFN cytokines, their receptors or their signaling pathways. In a one embodiment, the replication competent virus is a replication competent gamma retrovirus encoding a therapeutic gene. In a further embodiment, the virus is a replication competent MLV and the therapeutic gene is cytosine deaminase used in conjunction with 5-FC. Also provided are methods and compositions for treating a cell proliferative disorder, comprising first administering interferon to a subject with a tumor and subsequently administering a replication competent virus preparation to a subject. In a one embodiment, the replication competent virus is a replication competent gamma retrovirus encoding a therapeutic gene (sometimes referred to as a retroviral replicating vector, RRV, or replication competent retrovirus (RCR). In a further embodiment the virus is a replication competent MLV and the therapeutic gene is cytosine deaminase used in conjunction with 5-FC. In one embodiment the tumor is a brain tumor. Also provided are agents that specifically inhibit these signaling pathways.

The disclosure provides methods and compositions for the treatment of cancer. Treatment of cancer cells with radiation in combination with a RRV comprising a cytosine deaminase resulted in increased sensitivity of 5-FC mediated-killing of cancer cells compared to isolated treatment with radiation or the RRV containing the CD gene alone. Further, treatment of MLV-transduced cancer cells with radiation does not impair the functionality or spread of the vector over time. Accordingly, the disclosure provides a method of treating a cancer comprising administering a replication competent retrovirus comprising a polynucleotide encoding a cytosine deaminase to a cancer location, allowing sufficient time for the spread and transduction of tumor cells with the retrovirus, contacting the subject with 5-FC and radiation, wherein the 5-FC is metabolized to the cytotoxic compound 5-FU.

The disclosure also provides methods and compositions for treating cancer comprising administering a recombinant replication competent retrovirus (RCR) intravenously. In one embodiment, the disclosure comprises treating a brain cancer such as glioblastoma multiforme comprising administering an RRV intravenously, wherein the RCR crosses the blood brain barrier and transduces/infects cancer cells. In one embodiment, the intravenous administration comprises delivery of about $10^5$ to $10^{11}$ transforming units (TU) (e.g., about $9 \times 10^7$ TU). For example, the disclosure demonstrates that approximately 100 µl administered in a mouse model (which can be scaled by blood volume for larger animals or humans) is effective in treating cancer. In another embodiment, approximately 100 microliter doses (or scaled appropriately) are given at least once per day. In other embodiments, the dose is given over the course of several days at least once per day. The disclosure provides a pharmaceutical composition comprising a RRV particle in a pharmaceutically acceptable carrier for delivery intravenously. In one embodiment the pharmaceutical can comprise additional agents, in addition to the RRV, including, for example, IFN inhibitors. The RVR is further described herein below.

BRIEF DESCRIPTION OF THE DRAWINGS

FIG. 2B): A. Intraperitoneally (IP); B. mixed with vector (IT); C. without and with IP delivery of anti-IFN antibody (lower pictures show the visible GFP transduction in excised subcutaneous tumors).

DETAILED DESCRIPTION

Figure 1:
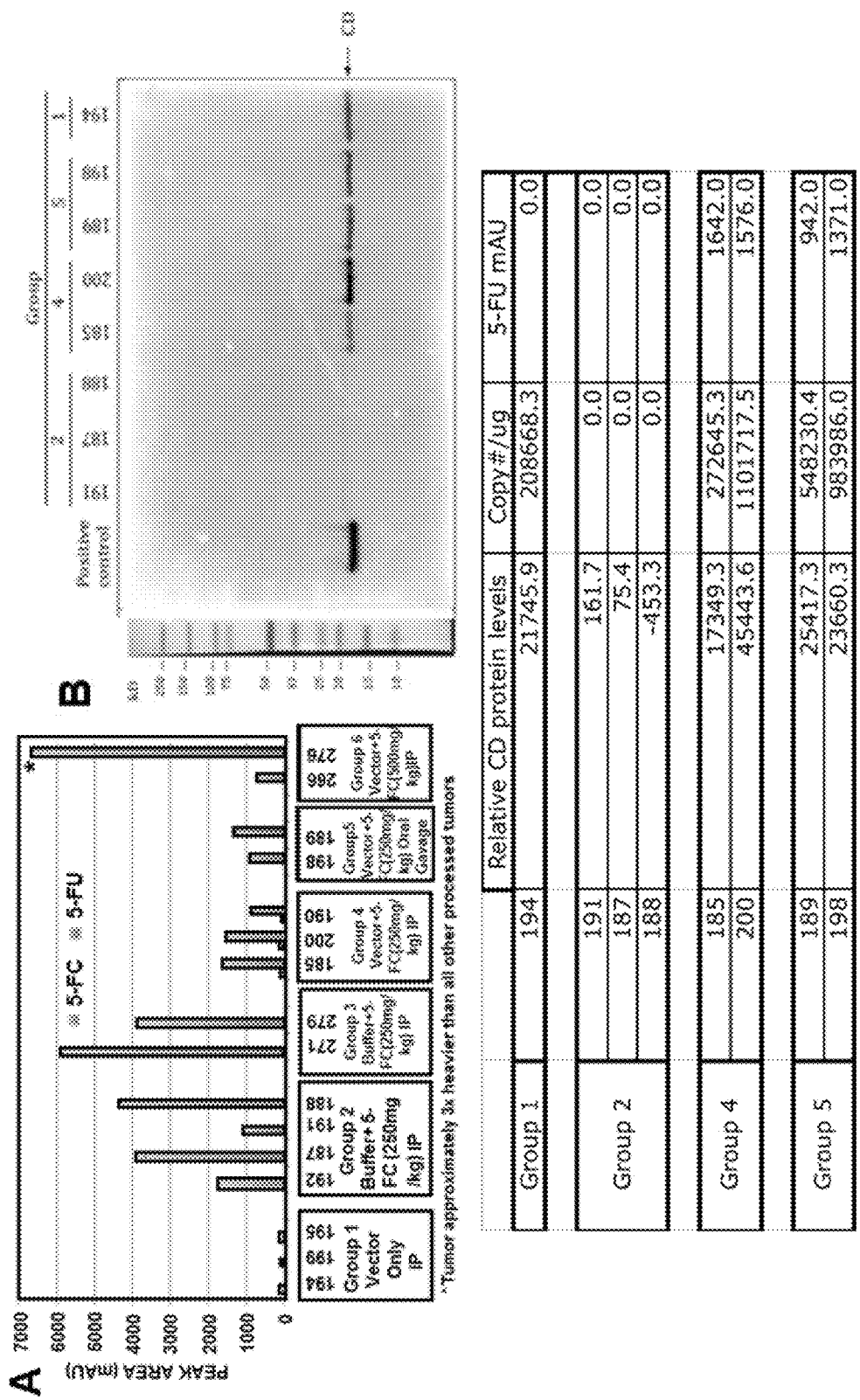
FIG. 1A-C shows the extent of therapeutic retroviral spread in intracranial Tu2449 tumors treated with Toca 511, an RRV encoding cytosine deaminase. Six groups of female B6C3F1 mice (16 mice, 8 weeks of age) were implanted IC with Tu-2449 glioma tumor cells then injected IC with vehicle (Group 2) or IC with Toca511 (Groups 1 and 3-6). When mice started losing weight (day 20), they were treated intraperitoneally (IP) or by oral gavage (OG) twice a day (BID) for 2 consecutive days with either PBS (Group 1) or 5-FC (500 mg/kg, Groups 3 and 6 or 250 mg/kg, Groups 2, 4, and 5). After two days of 5-FC dosing the mice were given one final 5-FC dose 1 hour before sacrifice. Tu-2449 tumors were surgically isolated from the brains for HPLC processing (A). Select tumors (B) were further trimmed for western blot analysis (tumors greater than 0.05 g). RIPA lysis supernatants were processed for HPLC analysis and when available RIPA lysis pellets were analyzed by PCR after DNA extraction (C). Extracted DNA was obtained from 1, 3, 2, and 2 mice in groups 1, 2, 4 and 5.

As used herein and in the appended claims, the singular forms "a," "and," and "the" include plural referents unless the context clearly dictates otherwise. Thus, for example, reference to "an agent" includes a plurality of such agents and reference to "the cancer cell" includes reference to one or more cancer cells, and so forth.

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of:"

Any publications discussed above and throughout the text are provided solely for their disclosure prior to the filing date of the present application. Nothing herein is to be construed as an admission that the inventors are not entitled to antedate such disclosure by virtue of prior disclosure.

Pathogen-associated molecular patterns (PAMPs) are molecules associated with groups of pathogens, including MLV, that alert cells and induce antiviral responses. Upon exposure to PAMPs, the cellular innate immune response and the inflammatory reaction that follows rely on evolutionarily conserved receptors termed pattern-recognition receptors (PRRs). Some of these receptors are located at the plasma membrane and include molecules such as the Toll-like receptors (TLR 1, 2, 4, 5, and 6) and scavenger receptors (CD36 and SR-A). Others occur in acidic endosomes (TLR 3, 7, 8, and 9). Still others can be found in the cytoplasm (PKR, the RIG-1-like helicases (RLHs)-RIGi, MDA5 and LGP2), the DNA-dependent activator of interferon (IFN) regulatory factors (IRFs)—DAI, and the nucleotide-binding oligomerization domain (NOD) receptors (Barral et al., Pharmacology & Therapeutics 124:219-234, 2009; Tamura et al., Annu Rev Immunol 26:535-584, 2008; Lee and Kim, Annu Rev Biochem 76:447-480, 2007; Yoneyama and Fujita, Med. Virol. 20:4-22, 2010). Table 1 and 2 summarize these interactions. A major consequence of stimulation of the PRR pathways can be production of Type 1 Interferons and activation of the interferon signaling pathways that lead to the expression of downstream antiviral genes such as retroviral "restriction" factors (Wolf and Goff, Annu Rev Gen 42:143-63, 2008).

TABLE 1

Human Toll-Like Receptors (TLR's) and known ligands

| Receptor | TLR1 | TLR2 | TLR3 | TLR4 | TLR5 | TLR6 | TLR7 | TLR8 | TLR9 |
|---|---|---|---|---|---|---|---|---|---|
| Ligand | Pam3* | Pam2#, Pam3*, PGN^ | dsRNA | LPS, virus fusion units | Flagellin | Pam2# | ssRNA | ssRNA | CpG DNA |

*Triacetylated lipopeptide
Diacetylated lipopeptide;
^peptidoglycan

TABLE 2

Examples of viral entities that have been shown to stimulate specific PRR's

| Virus | Ligand | PRRs |
|---|---|---|
| Measles | Hemagglutinin | |
| Herpes Simplex Virus | Unknown | TLR2 |
| Cytomegalovirus | Envelope protein | |
| Hepatitis C Virus | Core, NS3 proteins | |
| West Nile Virus | | |
| Respiratory Syncytial Virus | dsRNA | TLR3 |
| Influenza A | | |
| Respiratory Syncytial Virus | F protein | |
| Herpes Simplex Virus | Unknown | TLR4 |
| Mouse Mammary Tumor Virus | Envelope protein | |
| Dengue | ssRNA | TLR 7, 8 |
| Influenza | | |

TABLE 2-continued

Examples of viral entities that have been shown to stimulate specific PRR's

| Virus | Ligand | PRRs |
|---|---|---|
| Herpes Simplex Virus From Boo et al. 2010 | CpG | TLR9 |

Until now it had been assumed when treating tumors with viral vectors that such tumors would be at least partially incapacitated by genetic alterations in the genomes of tumors and that these alterations helped them escape the attention of the immune system. However, it has been discovered that this is not always true especially for replicative gamma-retroviruses and this discovery has now been used to develop effective therapeutic interventions. What has been demonstrated is that differences in the responses to PAMPs in tumors are usually due to epigenetic changes (rather than actual genetic deletions or mutations).

Replicative viral vectors are able to infect intracranial tumors in several mouse models, and achieve a therapeutic effect (see examples 1 and International Application Publ. No. WO2010/036986, incorporated herein by reference). However, surprisingly, the same tumors are resistant to infection with the same vector when implanted subcutaneously (see example 1). The disclosure provides methods and compositions wherein this block can be overcome using various adjuvant and co-therapeutic. For example, by limiting the inflammatory and immune cascade and/or by blocking the action of Interferon, for example, by co-administration of anti-IFN alpha antibodies prior to, concurrently with or subsequence to (or a combination thereof) with the retroviral therapy. For example, the co-therapeutic can be administered at the same time either mixed with the vector or administered systemically (e.g., intraperitoneally, see example 2).

The administration of the anti-IFN agent is useful at or about the time of initial vector administration and can be simply mixed into the injection formulation, or administered separately for 1, 2 or 3 days or longer up to about 14 days, following administration of the replicative viral vector, and more specifically the replicative gamma-retrovirus. Based on these surprising results the disclosure provides methods that allow viral vector replication in tumors in vivo that are otherwise resistant to viral vector infection and methods that lead to a therapeutic effect.

Therefore, in one embodiment of the disclosure, a method to interrupt and modulate such pathways to allow effective therapeutic replication of replicative viral vectors is provided. In another embodiment, the method is used to interrupt and modulate such pathways to allow effective therapeutic replication of replicative retroviruses and associated vectors. In one embodiment, these methods comprise the administration of inhibitors of pattern recognition receptors and their signaling pathways. In another embodiment, these inhibitors are chemical entities that have been shown to interact with individual proteins or protein complexes in the TLR receptor signaling pathway including without limitation TRIF, TRAF3, TRAF6, RIP-1, TRAF-1, NAP1, RIO1, TAK1, IRAK4, MyD88, TRAF, osteopontin, IRF-3, IRF-5, IRF-7, IRF-9. In yet another embodiment, these methods comprise administration of inhibitors of the cytokines interferon alpha and beta, their receptors and signaling pathways that lead to expression of antiviral genes in target cells. In a further embodiment, these inhibitors are chemical entities that have been shown to interact with individual proteins or protein complexes in the Interferon signaling pathways including without limitation IFNR1, IFNR2, TRAIL-R1, TRAIL-R2, ISGF-3, JAK1, JAK2, TYK2, STAT1, STAT2, IRF-9. In one embodiment, the inhibitors of both pathways are administered prior to, simultaneously with or following administration of a replicative retroviral vector.

Several examples of chemical entities that can be used to inhibit the signaling pathway members and allow more vigorous viral vector replication are given in Table 3. However, for gamma-retroviruses, that require replicating target cells for productive infection, the use of such agents is not easy to predict as any compound that inhibits cellular replication, will cause a corresponding inhibition of viral infection. Many agents that have been identified as having activity as inhibitors of pattern recognition or TLR action also inhibit cellular replication. In fact many of these agents are primarily anti-tumor agents and so, almost by definition, inhibit cellular replication machinery. Therefore it is not possible to easily predict which compounds with reputed anti-pattern recognition/anti-IFN signaling or other targeted action on a single viral component (e.g steroids) will be beneficial for RRV treatment without direct testing of the specific compound.

TABLE 3

Available TLR/type 1 Interferon pathway inhibitors

| Inhibitor | Target/MOA | In vitro data | In vivo data | Dosage/IC50 | Reference | Vendor |
|---|---|---|---|---|---|---|
| Cetrorelix (Cetrotide) | Blocks the action of GnRH on the pituitary | ✓ | ✓(0.625-12.5 mg/kg) | 3 mg single dose or .25 mg/day (human) | Rick et al., Prostate. 2010 Oct. 13 | Merck |
| Morphine | Binds to and activates the μ-opioid receptors in the central nervous system | ✓($10^{-14}$M to $10^{-8}$M) | ✓ | Human dose varies widely; oral: 8-20 mg; 5-35 mg/hr; 15-200 mg cont. rls. | Wan et al., J Neuroimmunol. 2008 Aug. 13; Wang et al., Am J Pathol. 2005 November | Elkins-Sinn, Inc. |
| Vorinostat (Zolina) (HDACi SAHA) | Class 1 and 2 histone deacetylases | ✓ | ✓ | 100-300 mg/day dose | Vlasakova et al. Blood. 2010 Oct. 19 | Patheon Inc. for Merck |
| Valproic acid (Convulex) | Inhibits the transamination of GABA; blocks the voltage-gated sodium channels and T-type calcium channels; class 1 histone deacetylases | ✓ | ✓ | Max human dose of 60 mg/kg | Vlasakova et al. Blood. 2010 Oct. 19 | Pfizer (Depakene under Abbott) |
| Tacrolimus (FK-506 or Advagraf) | Reduces peptidyl-prolyl isomerase activity by binding to the immunophilin FKBP12 creating a new complex that inhibits calceneruin (IL2 txn) | ✓ (6-20 nM or 5-15 ng/ml) | ✓ (0.1 mg/kg in dog) | 0.5, 1, 3 and 5 mg capsules sustained release once a day (0.15-0.20 mg/kg) | Morteau et al. (2010) Renal Transplant Immunosuppression Impairs Natural Killer Cell Function In vitro and In vivo. PLoS ONE 5(10) | Astellas Pharma Inc. |
| Pimecrolimus (Elidel) | Like tacrolimus, but no effect on dendritic cells | ✓ | ✓(max: 1.4 ng/mL) | 1% cream | Gisondi et al. Int J Clin Pract. 2005 August; 59(8) | Novartis |
| Bortezomib (Bortezomib) | Proteosome inhibitor: The boron atom in bortezomib binds the catalytic site of the 26S proteasome. | ✓ | ✓(0.7-1.3 mg/m$^2$/dose IV) | (0.7-1.3 mg/m$^2$/dose IV) | Hirai et al. Blood. 2010 Oct. 18 | Millennium Pharmaceuticals |
| Sirolimus (rapamycin; Rapamune) | Rapamycin binds to FKBP12, the FKBP12-rapamycin complex, to inhibit the mTOR pathway | ✓ | ✓ | Up to 6 mg loading dose; 2 mg/day maintenance | Powell et al., Immunity. 2010 Sep. 24; 33(3): 301-11. Martelli et al., Oncotarget. 2010 June; 1(2): 89-103 | Wyeth |
| Ruxolitinib (INCB-018424) | Selective Jak1 and Jack2 inhibitor | ✓ (IC$_{50}$ 3-5 nM) | ✓ | 25 mg twice daily or 100 mg once daily as maximum tolerated doses, on the basis of reversible thrombocytopenia | Verstovsek et al., N Engl J Med 2010; 363: 1117-1127. Mesa, IDrugs. 2010; June; 13(6) | Incyte |

TABLE 3-continued

Available TLR/type 1 Interferon pathway inhibitors

| Inhibitor | Target/MOA | In vitro data | In vivo data | Dosage/IC50 | Reference | Vendor |
|---|---|---|---|---|---|---|
| INCB-028050 | Selective Jak1 and Jack2 inhibitor | ✓($IC_{50}$ = 5 nM) | ✓ | Clinical evaluation in RA is ongoing | Fridman et al., J Immunol. 2010. May 1; 184(9) | Incyte |
| ISA-247 | Calcineurin inhibitor (cyclosporine analog) that binds to with cyclophilin to calcineurin, inhibiting the transcription of interleukin 2 | ✓ | ✓ (high dose of 40 mg/kg: 2x/day rats and) | In phase III for Psoriasis | Birsan et al., Transpl Int. 2005 May; 17(12) | Isotechnika and Roche |
| Cyt387 | Jak1/Jak2 inhibitor | ✓ IC50 = 11 and 18 nM, resp. Between 0.5 and 1.5 μM apoptosis in JAK2-dependent hematopoietic cell lines | ✓ | Phase I/II for Primary Myelofibrosis or Post-Polycythemia Vera or Post-Essential Thrombocythemia Myelofibrosis | Tyner et al., Blood. 2010 Jun. 24; 115(25) Pardanani et al. Leukemia (2009) 23, 1441-1445 | Cytopia and Novartis |
| Low MW Dextran (DXS 5000) | Blocks complement activation | ✓ | ✓ | 43 +/− 18 ug/ml | Fiorante et al., Xenotransplantation. 2001 February; 8(1). Millard et al., Mol Immunol. 2010 August; 47(14). | ?? |
| LF2 of EBV | Inhibits the dimerization of IRF7 | ✓ | x | | Wu et al., J Virol. 2009 January; 83(2) | Recomb |
| B18 of vaccinia | Acts as a soluble receptor to bind type 1 IFN | ✓ | x | | Waibler et al., J Virol. 2009 February; 83(4) | Recomb |
| Y136 of yatapox | Acts as a soluble receptor to bind type 1 and 3 IFN | ✓ | x | | Huang et al., Proc Natl Acad Sci USA. 2007 Jun. 5; 104(23): | Recomb |
| NS1 of influenza | Binds to RIG-I/ IPS-1 complexes and blocks downstream signaling, resulting in attenuation of type I IFN | ✓ | x | | Haye et al., J Virol. 2009 July; 83(13) | Recomb |
| Sugar-modified cationic liposome/NF-κB decoy | Reduces vector-induced NF-κB activation | ✓ | x | ?? | Huang et al., J Control Release. 2009 Jan. 19; 133(2) | ?? |
| 2-aminopurine | PKR | ✓ | ✓ | 5-10 mM | Pernod et al., 2004; Rowland et al., 2001; Hu et al., 1993 | Sigma |
| Imidazolo-oxindole | PKR | ✓ | x | 1 microM | Uller et al., 2010 | Sigma; EMD/Merck |
| Chloroquine (ARALEN) | TLR3, 7, 8, 9 | ✓ | x | 20 microM (10 ug/mL) Oral dosing 50 mg/kg 5 mg/kg | Uller et al., 2010; Yasuda et al., 2008; Matsukura et al., 2007; Kumar et al., 2006; | Sigma Sanofi-Aventis |
| MPI-485520 | IKKε; TBK1 | ✓ | ✓ | 500 pM Oral dosing 30-100 mg/kg | Richards et al., FASEB 2010 Annual Meeting abstract | Myrexis Inc |
| Histone deacetylase inhibitor (MS-275) | Histone deacetylase | ✓ | ✓ | 3.7 microM i.p. 7 mg/kg per 12 h X 10 | Nguyen et al., 2008; Eyupoglu et al., 2006 | Calbiochem |
| rapamycin | mTORC1/4E-BP/S6K1/2 | ✓ | ✓ | 5 mg/kg i.p. 5X/wk X 2 | Alain et al., 2010; Hinkkanen et al., 2010 ESGCT abstract | Sigma |
| Sertraline | PI3K/Akt | ✓ | x | 15 microM Oral dosing 50-200 mg/day | Zhu et al., 2010 | Sigma Pfizer |

Several viruses encode proteins or peptides that are necessary for replication in normal target tissue, but not necessarily in immortalized tissue culture cells. Some of these factors appear to have such anti-TLR signaling or anti-IFN-signaling pathway properties. However, gamma-retroviruses in general and MLV in particular lacks any such protein or peptide, which implies that this is not a necessary feature of MLV nor that MLV needs such function to replicate or persist in its host. This is thought to be because of the non-lytic, non-inflammatory nature of gamma retroviral infection and spread, including the ability of the viral genome to integrate in the host genome and behave like an endogenous gene or genes. However, unexpectedly these properties have now been discovered here to be insufficient for viral vector spread in subcutaneous tumors and to limit therapeutic infection of tumors of non-homologous species such as dog (see example 4) and man. In a further embodiment, the signaling pathway inhibitors are heterologous viral proteins that have been shown to inhibit these pathways including, without limitation: LF2 from EBV (Table 3); B18 from Vaccinia virus (Table 3); y136 of yatapox (Table 3); NS1 of Influenza (Table 3); vaccinia E3 protein from vaccinia (Valentine and Smith, Journal of General Virology, 91:2221-2229, 2010); peptides from Japanese encephalitis virus (JEV) (Lin et al., J. Virol., 9285-9294, 2004); non-structural protein 2 from Chikungunya virus (Fros et al., J. Virol., 2010 doi:10.1128/JVI.00949-10); and ICP27 from Herpes virus (Johnson and Knipe, Virology, 396:21-29, 2010). In a further embodiment, the inhibitors are siRNA, shRNA or other miRNA derivatives (Kim and Rossi, BioTechniques, 44:613-616, 2008) to genes encoding members of the signaling pathways. The design of active siRNA and shRNA molecules against specific genes is well known to those skilled in the art (see, e.g., Horn. and Boutros, Nucl. Acids Res. 38(suppl 2):W332-W339, 2010; Li et al., RNA, 13:1765-1774, 2007). In one embodiment, genes for signaling pathway inhibitory proteins or siRNA can be delivered by non-viral (DeFougerolles Hum Gen Ther., 19:125-132, 2008) or non-replicative viral vectors such as lentiviral vectors (N. Manjunath, Advanced Drug Deliv Rev., 732-745, 2009), AAV vectors and Adenoviral vectors, so that limited local expression occurs, but does not spread with the replicative viral vector. In one embodiment, these agents are mixed with the replicative vector at administration. In another embodiment the agent is administered systemically or locally and is active at or around the site of administration of the replicative viral vector over a period of over an hour, a day, a week, or a month, but is not part of the replicative viral vector genome.

In a separate embodiment, methods are provided for treating a tumor with interferon that is initially either therapeutic or, minimally, not tumor-promoting, so that the tumor regresses, stabilizes or grows less quickly than before treatment, then when treatment has been completed or is no longer effective the tumor is treated with a replicative vector such as a recombinant replicative retroviral vector. The tumor cells that have become resistant to interferon are now more susceptible to infection by a replicating viral vector, and replicative retroviral vector, and the spread of the virus is more efficient (see examples 6 through 10). In this embodiment, FDA approved preparations and formulation can be used such as Interferon alpha (Roferon A and Intron A) is approved for human use in the USA for several cancers: Hairy cell Leukemia (IM or SQ), Melanoma (IV), aggressive Non-Hogkins Lymphoma, warts, Kaposi's sarcoma and early Philadelphia+ Chronic Myelogenous Leukemia (CML) (http:(//www.)fda.gov/Drugs/InformationOnDrugs/). Beta-IFN 1a and 1b are approved for human use (Betaseron®—Bayer; Avonex®—Biogen-Idec; Rebif®—Merck-Serono; Feron®—Daichi-Sankyo) and are used extensively in Japan for treatment of Malignant Glioma (Motomura et al., Cancer, 2010) and can be effective against multiple other cancers (Chawla-Sarkar et al., Apoptosis, 8:237-249, 2008). Thus, a tumor that was previously partially refractory to retroviral infection and replication becomes highly susceptible with consequent increase in therapeutic effect. Interferon variants and interferon receptor agonists can also be used in the methods and compositions of the disclosure alone or in combination with naturally occurring interferons.

As described above and in the Examples herein, the disclosure provides methods and compositions useful for rendering a tissue comprising a cell proliferative disorder susceptible for infection and spread of a viral vector. The methods comprise contacting the tissue simultaneously or sequentially with a PPR or IFN inhibitory agent and a replication competent viral vector. The PPR or IFN inhibitory agent renders the tissue susceptible for spread an increase of the viral load in the tissue by reducing or inhibiting viral immune responses. Various viral vectors and their constructs useful in the methods of the disclosure are provided below.

In addition, the disclosure demonstrates that administration of glucocorticoids are useful in modifying the immune response during therapy with a retroviral vector. Glucocorticoids are involved in regulation of many physiological systems. They are potent immunosuppressors, especially for the innate immune response and the subsequent inflammatory reaction, due to their functions in providing negative feedback on proinflammatory signaling and gene expression (McKay et al., 1999). The role of glucocorticoids plays in protecting the brain during innate immune response in the brain has been reported (Nadeau et al., 2003).

The glucocorticoid receptor is a ligand-induced transcription factor. When bound by glucocorticoids, the activated receptor modulates gene expression by binding to glucocorticoid response elements (GRE) or by interacting with other transcription factors (1 ng et al., 1995; Picard et al., 1987). GRE present in the LTR region of retroviruses has been described to play role in enhancing promoter activity in response to glucocorticoids and thereby increasing viral production (Solodushko et al., 2009; Malone et al., 1994; Duch et al., 1993).

By "glucocorticoid" is meant a synthetic or naturally occurring corticosteroid drug or hormone that is a functional or structural analog of an endogenous glucocorticoid produced by the adrenal gland. Exemplary glucocorticoids include prednisolone, methylprednisolone, hydrocortisone, betamethasone and dexamethasone. Dexamethasone is a potent synthetic member of the glucocorticoid class of steroid drugs currently used for various disease and disorders. It acts as an anti-inflammatory and immunosuppressant. In patients with brain tumor, dexamethasone is used to reduce edema and during radiation to improve neurological symptoms. The disclosure provides an adjuvant treatment for enhancing replicating retroviral vector (RRV) spread especially in glioma cells which supports slow viral spread comprising co-administering a glucocorticoid before, during or after retroviral therapy treatment. Further, the disclosure demonstrates that administration of antiprogestins such as mifepristone (RU-486) are useful in modifying the efficiency of infection during therapy with a retroviral vector. RU486 is clinically used as an abortifacient in the first months of pregnancy, and in smaller doses as an emergency contraceptive. Studies conducted in vitro and in animals shows no genotoxic potential for Mifepristone. In addition, Mifepristone has been used to treat Cushing's syndrome with treatment durations being as long as 10 years with no adverse effect observed. As with glucocorticoids, although there is some evidence for enhancement of some parts of the retroviral life cycle, it is completely unclear how that translates into a viral infection therapy with replicating retroviral vectors, in particular when the therapy involves the use of a prodrug. It is well known that gamma retroviruses such as MLV cannot productively infect non-replicating cells. Therefore for any agent that may modify viral transcription or integration, but that also inhibits cell replication (such as some steroids and almost all anti-cancer drugs) the overall effect of that agent, either in vitro or in vivo is impossible to predict.

The disclosure provides an adjuvant with mifepristone or analogues for improving treatment with retroviral replicating vector (RRV). The methods are especially useful in glioma cells that support slow viral spread.

The disclosure also demonstrates that retroviral treatment with a recombinant polynucleotide encoding a polypeptide with cytosine deaminase activity followed by 5-FC therapy improves radiation sensitization of the infected cancer cells. A radiation sensitizer is an agent used to enhance the effect of radiation therapy. In delivering potentially curative doses of radiation, it is necessary to balance the need for local tumor control with the potential for damage to surrounding normal tissues by the delivered dose of radiation (Bush et al., 1978). It is therefore desirable to use the lowest radiation dose consistent with local control. One way to achieve this would be to utilize a radiation sensitizing agent to enhance cytotoxicity of delivered radiation to the tumor.

Radiation causes cell death by damaging critical targets within the cell, most commonly chromosomal DNA (Hendrickson and Withers, 1991). Radiation therapy relies on two types of ionizing radiation: (1) directly ionizing subatomic particle radiation, such as alpha particles and beta particles (electrons), neutrons, protons, mesons, heavy charged ions, etc., and (2) indirectly ionizing electromagnetic radiation, which exists as a family of waves of varying frequency including high frequency x-rays or gamma rays. However, of the two, electromagnetic radiation is more commonly used in radiation therapy today. In tissue, electromagnetic radiation in the form of x-rays or gamma rays can interact with molecules (especially water) causing the ejection of high-energy electrons. The electrons can break the sugar phosphate bonds in DNA directly (direct action) or the process of electron ejection can ultimately produce free (uncharged) radicals that can also break the chemical (sugar-phosphate) bonds in DNA (indirect action). The damage caused through the indirect mechanism is more significant (Hendrickson and Withers, 1991; Mulcahy et al., 1993; Rubin and Siemann, 1993; Chapman et al., 1974).

Radiation damage is produced primarily by hydroxyl radicals. This radical is extremely reactive and short lived. It causes damage primarily in the vicinity in which it is generated (~4 nm). If it comes into contact with a hydrated electron it is deactivated by conversion to a hydroxide ion. Hydrated electrons are strong reducing species and highly energetic. They are very mobile by comparison to the hydroxyl radical, can travel distances quickly, and through direct action can damage DNA. However, as mentioned above, they also deactivate hydroxyl radicals readily. Agents with strong electron affinity, by virtue of "soaking up" solvated electrons, prevent them from neutralizing hydroxyl radicals and thereby allow hydroxyl radicals to exert their effect (Adams and Dewey, 1963). Oxygen and other compounds with strong electron affinity would thus be expected to act as radiation sensitizers.

5-Fluorouracil (5-FU) is one of the most commonly used chemotherapeutic agents for certain cancers and has been used extensively with radiation. There are a number of mechanisms by which 5-FU could increase radiation sensitivity at the cellular level. One mechanism is thought to be through the killing of S phase cells, which are relatively radioresistant. Radiosensitization under non-cytotoxic conditions occurs only when cells are incubated with the drug before and during radiation. Thus, several studies have suggested that 5-FU should be given continuously during a course of fractionated radiation to achieve radiosensitization of most fractions. Indeed, the use of protracted venous infusion of 5-FU has become a standard therapy for rectal cancer (Rich et al., Oncology 13: 131-134, 1999). However, protracted venous infusion over a 5- to 6-week period is relatively complex, requiring specialized pumps and long-term venous access which makes the patients susceptible to infection.

A cytosine deaminase (EC 3.5.4.1) is an enzyme that catalyzes the chemical reaction

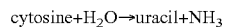

cytosine+$H_2O$→uracil+$NH_3$

Thus, the two substrates of this enzyme are cytosine and $H_2O$, whereas its two products are uracil and $NH_3$. This enzyme belongs to the family of hydrolases, those acting on carbon-nitrogen bonds other than peptide bonds, specifically in cyclic amidines. The systematic name of this enzyme class is cytosine aminohydrolase. This enzyme is also called isocytosine deaminase. This enzyme participates in pyrimidine metabolism.

More particularly, cytosine deaminase is an enzyme involved in the metabolic pathway for pyrimidines, through which exogenous cytosine is transformed, via hydrolytic deamination, into uracil. Cytosine deaminase (CDase or CD) activities have been demonstrated in prokaryotes and lower eukaryotes, but they are absent in mammals (Koechlin et al., 1966, Biochem. Pharmacol. 15, 435-446; Polak et al., 1976, Chemotherapy 22, 137-153). The FCY1 gene of *Saccharomyces cerevisiae* (*S. cerevisiae*) and the coda gene of *E. coli*, which encode, respectively, the CDase of these two organisms, are known and their sequences are published (EP 402 108; Erbs et al., 1997, Curr. Genet. 31, 1-6; WO 93/01281). CDase also deaminates a cytosine analogue, 5-fluorocytosine (5-FC) to 5-fluorouracil (5-FU), which is a highly cytotoxic compound, in particular when it is converted to 5-fluoro-UMP (5-FUMP). Cells which lack CDase activity, due either to an inactivating mutation of the gene encoding the enzyme or to their natural deficiency for this enzyme (for example mammalian cells) are resistant to 5-FC (Jund and Lacroute, 1970, J. Bacteriol. 102, 607-615; Kilstrup et al., 1989, J. Bacteriol., 171, 2124-2127). On the other hand, it has been demonstrated that it is possible to transmit 5-FC sensitivity to mammalian cells into which the sequence encoding a CDase activity has been transferred (Huber et al., 1993, Cancer Res. 53, 4619-4626; Mullen et al., 1992, Proc. Natl. Acad. Sci. USA 89, 33-37; WO 93/01281). Accordingly, the use of CD is advantageous in the context of gene therapy, in particular anticancer gene therapy.

The disclosure overcomes many of the foregoing difficulties by provided radio-sensitized cancer cells using local 5-FU sensitizing. The disclosure also provides methods of improving radiations therapy in a subject having cancer. The method includes adjuvant therapy with a radiation following delivery of a retroviral vector of the disclosure expressing a cytosine deaminase that converts the inactive prodrug 5-fluorocytosine (5-FC) to the cytotoxic drug 5-fluorouracil (5-FU).

In this method the vector expressing cytosine deaminase is administered and allowed to spread in a tumor. The subject is then administered 5-FC in an amount sufficient to produce 5-FU in the infected cancer tissue. Thus, the disclosure also provides therapeutic improvement in cancer treatment by radiosensitizing a tumor using replication competent viral vector of the disclosure.

The disclosure also provides methods of monitoring the effect viral spread and cytosine deaminase activity. This is important in determining dosing, redosing and the like of gene therapy subjects and 5-FC conversion to 5-FU. For example, 5-FC sensitivity varies a great deal depending on the cell lines. Low sensitivity is observed, for example, in PANC-1 (carcinoma of the pancreas) and SK-BR-3 (breast adenocarcinoma) human tumour lines transduced with a retrovirus expressing the coda gene of *E. coli* (Harris et al., 1994, Gene Therapy 1, 170-175). This phenomenon is explained by the absence or poor endogenous conversion of the 5-FU formed by the enzymatic action of the CDase, to cytotoxic 5-FUMP. This step, which is normally carried out in mammalian cells by orotate phosphoribosyltransferase (OPRTase), may be absent in certain tumours and thus make gene therapy based on CDase ineffective. In prokaryotes and lower eukaryotes, uracil is transformed into UMP through the action of uracil phosphoribosyltransferase (UPRTase activity). This enzyme also converts 5-FU to 5-FUMP. Importantly, bacterial uracil phosphoribosyltransferase (UPRT) is functionally equivalent to orotate phosphoribosyltransferase (OPRT) or uridine-5'-monophosphate synthase of mammalian cells. These enzymes mediate the conversion of 5-fluorouracil (5-FU) (a fluorinated analog of uracil) to 5-fluorouridine 5' monophosphate (5-FUMP). 5-fluorouridine 5' monophosphate is subsequently converted to 5-FdUDP and FdUTP via the mammalian de novo pyrimidine pathway. Each 5-FdUTP is an irreversible inhibitor of thymidylate synthase (Thy-A) and results in dTTP starvation. It is widely accepted that this conversion is one of the requisite pathways to achieve cytotoxic effects of 5-fluorouracil and that bacterially uracil phosphoribosyltransferase of bacterial origin is able to convert 5-fluorouracil to the same active metabolite as does mammalian orotate phosphoribosyltransferase. In the absence of UPRTase activity or OPRTase activity, the 5-FU, originating from the deamination of the 5-FC by the CDase, is not transformed into cytotoxic 5-FUMP (Jund and Lacroute, 1970, J. Bacteriol. 102, 607-615).

An unexpected, but useful measure of activity of CD in subjects undergoing gene therapy comprises the measure of α-fluoro-β-alanine (FBAL). In most normal tissues and especially in the liver, detoxification of 5-FU proceeds via dihydropyrimidine dehydrogenase (DPD) to give DHFU, which is converted to FUPA and FBAL via subsequent reactions. These catabolites can be readily detected in the plasma and urine of patients or animals undergoing fluoropyrimidine therapy.

Detection of FBAL in the plasma (or other biological sources) of a subject treated with a vector comprising a polypeptide having cytosine deaminase activity includes (1) delivery of the vector (e.g., a replication competent retrovirus comprising a CD such as Toca 511) to a brain tumor or other neoplastic tissue and sufficient spread of virus within the tumor or neoplastic tissue, (2) expression of CD after the integration of virus into the host (e.g., tumor) cell genome, (3) conversion of orally administered 5-FC to 5-FU by the expressed CD enzyme in the tissue, and (4) metabolism of the 5-FC to produce 5-FU and export of the 5-FU in sufficient quantities to enter the systemic circulation and be metabolized to detectable amounts of FBAL. The unexpected ability of the vector and CD of the disclosure to produce sufficient quantities of FBAL provides a useful biomarker for determine target dosage of 5-FC, target delivery and spread of a vector comprising CD to enable a physician to monitor and adjust a patient's treatment.

Thus, the disclosure provides a diagnostic method of monitoring gene delivery of a polynucleotide comprising cytosine deaminase activity, the genes expression and the activity of the expressed gene. In one embodiment, the disclosure provides a method comprising measuring FBAL in a sample from a subject receiving 5-FC therapy, wherein the subject received gene delivery of a vector that expresses a cytosine deaminase. The sample can be plasma, urine or other available biological fluids such as saliva. The sample can be analyzed by HPLC. For example, FBAL can be detected by isocratic, reverse phase HPLC methods. The HPLC can be used in conjunction with mass spectrometer detection of FBAL in the eluate.

Embodiments of the disclosure utilize as a therapy replication competent viral vectors that contain a heterologous polynucleotide encoding, for example, a cytosine deaminase or mutant thereof, an miRNA or siRNA, a cytokine, an antibody binding domain or the like or combinations thereof, that can be delivered to a cell or subject. The viral vector can be an adenoviral vector, a measles vector, a herpes vector, a retroviral vector (including a lentiviral vector), a rhabdoviral vector such as a Vesicular Stomatitis viral vector, a reovirus vector, a Seneca Valley Virus vector, a poxvirus vector (including animal pox or vaccinia derived vectors), a parvovirus vector (including an AAV vector), an alphavirus vector or other viral vector known to one skilled in the art (see also, e.g., *Concepts in Genetic Medicine*, ed. Boro Dropulic and Barrie Carter, Wiley, 2008, Hoboken, N.J.; *The Development of Human Gene Therapy*, ed. Theodore Friedmann, Cold Springs Harbor Laboratory Press, Cold springs Harbor, N.Y., 1999; *Gene and Cell Therapy*, ed. Nancy Smyth Templeton, Marcel Dekker Inc., New York, N.Y., 2000 and *Gene Therapy: Therapeutic Mechanism and Strategies*, ed. Nancy Smyth Templetone and Danilo D Lasic, Marcel Dekker, Inc., New York, N.Y., 2000; the disclosures of which are incorporated herein by reference).

In certain embodiments, the viral vector is a replication competent retroviral vector (RRV) capable of infecting only replicating mammalian cells. In another embodiment, a replication competent retroviral vector used in the compositions and methods of the disclosure comprises an internal ribosomal entry site (IRES) 5' to the heterologous polynucleotide encoding, e.g., a cytosine deaminase, miRNA, siRNA, cytokine, receptor, antibody or the like. When the heterologous polynucleotide encodes a non-translated RNA such as siRNA, miRNA or RNAi then no IRES is necessary, but may be included where another heterologous polynucleotide may be desirably expressed. In one embodiment, the siRNA, miRNA, RNAi polynucleotide is 3' to a ENV polynucleotide of a retroviral vector. In another embodiment the siRNA, miRNA, RNAi polynucleotide is expressed from a pol III promoter such as the H1 promoter. In yet another embodiment, an IRES cassette comprising an internal ribosome entry site operably linked to a heterologous polynucleotide is 3' to the ENV polynucleotide and 5' to the 3' LTR.

The disclosure provides modified retroviral vectors. The modified retroviral vectors can be derived from members of the retroviridiae family. The Retroviridae family consists of three groups: the spumaviruses- (or foamy viruses) such as the human foamy virus (HFV); the lentiviruses, as well as visna virus of sheep; and the oncoviruses (although not all viruses within this group are oncogenic). The term "lentivirus" is used in its conventional sense to describe a genus of viruses containing reverse transcriptase. The lentiviruses include the "immunodeficiency viruses" which include human immunodeficiency virus (HIV) type 1 and type 2 (HIV-1 and HIV-2) and simian immunodeficiency virus (SIV). The oncoviruses have historically been further subdivided into groups A, B, C and D on the basis of particle morphology, as seen under the electron microscope during viral maturation. A-type particles represent the immature particles of the B- and D-type viruses seen in the cytoplasm of infected cells. These particles are not infectious. B-type particles bud as mature virion from the plasma membrane by the enveloping of intracytoplasmic A-type particles. At the membrane they possess a toroidal core of 75 nm, from which long glycoprotein spikes project. After budding, B-type particles contain an eccentrically located, electron-dense core. The prototype B-type virus is mouse mammary tumor virus (MMTV). No intracytoplasmic particles can be observed in cells infected by C-type viruses. Instead, mature particles bud directly from the cell surface via a crescent 'C'-shaped condensation which then closes on itself and is enclosed by the plasma membrane. Envelope glycoprotein spikes may be visible, along with a uniformly electron-dense core. Budding may occur from the surface plasma membrane or directly into intracellular vacuoles. The C-type viruses are the most commonly studied and include many of the avian and murine leukemia viruses (MLV). Bovine leukemia virus (BLV), and the human T-cell leukemia viruses types I and II (HTLV-I/II) are similarly classified as C-type particles because of the morphology of their budding from the cell surface. However, they also have a regular hexagonal morphology and more complex genome structures than the prototypic C-type viruses such as the murine leukemia viruses (MLV). D-type particles resemble B-type particles in that they show as ring-like structures in the infected cell cytoplasm, which bud from the cell surface, but the virion incorporate short surface glycoprotein spikes. The electron-dense cores are also eccentrically located within the particles. Mason Pfizer monkey virus (MPMV) is the prototype D-type virus.

Retroviruses have been classified in various ways but the nomenclature has been standardized in the last decade (see ICTVdB—The Universal Virus Database, v4 on the World Wide Web (www) at ncbi.nlm.nih.gov/ICTVdb/ICTVdB/ and the text book "Retroviruses" Eds Coffin, Hughs and Varmus, Cold Spring Harbor Press 1997; the disclosures of which are incorporated herein by reference). In one embodiment, the replication competent retroviral vector can comprise an Orthoretrovirus or more typically a gamma retrovirus vector.

The retrovirus particle is composed of two identical RNA molecules. Each wild-type genome has a positive sense, single-stranded RNA molecule, which is capped at the 5' end and polyadenylated at the 3' tail. The diploid virus particle contains the two RNA strands complexed with gag proteins, viral enzymes (pol gene products) and host tRNA molecules within a 'core' structure of gag proteins. Surrounding and protecting this capsid is a lipid bilayer, derived from host cell membranes and containing viral envelope (env) proteins. The env proteins bind to a cellular receptor for the virus and the particle typically enters the host cell via receptor-mediated endocytosis and/or membrane fusion.

After the outer envelope is shed, the viral RNA is copied into DNA by reverse transcription. This is catalyzed by the reverse transcriptase enzyme encoded by the pol region and uses the host cell tRNA packaged into the virion as a primer for DNA synthesis. In this way the RNA genome is converted into the more complex DNA genome.

The double-stranded linear DNA produced by reverse transcription may, or may not, have to be circularized in the nucleus. The provirus now has two identical repeats at either end, known as the long terminal repeats (LTR). The termini of the two LTR sequences produces the site recognized by a pol product—the integrase protein—which catalyzes integration, such that the provirus is always joined to host DNA two base pairs (bp) from the ends of the LTRs. A duplication of cellular sequences is seen at the ends of both LTRs, reminiscent of the integration pattern of transposable genetic elements. Integration is thought to occur essentially at random within the target cell genome. However, by modifying the long-terminal repeats it is possible to control the integration of a retroviral genome.

Transcription, RNA splicing and translation of the integrated viral DNA is mediated by host cell proteins. Variously spliced transcripts are generated. In the case of the human retroviruses HIV-1/2 and HTLV-I/II viral proteins are also used to regulate gene expression. The interplay between cellular and viral factors is a factor in the control of virus latency and the temporal sequence in which viral genes are expressed.

Retroviruses can be transmitted horizontally and vertically. Efficient infectious transmission of retroviruses requires the expression on the target cell of receptors which specifically recognize the viral envelope proteins, although viruses may use receptor-independent, nonspecific routes of entry at low efficiency. In addition, the target cell type must be able to support all stages of the replication cycle after virus has bound and penetrated. Vertical transmission occurs when the viral genome becomes integrated in the germ line of the host. The provirus will then be passed from generation to generation as though it were a cellular gene. Hence endogenous proviruses become established which frequently lie latent, but which can become activated when the host is exposed to appropriate agents.

As mentioned above, the integrated DNA intermediate is referred to as a provirus. Prior gene therapy or gene delivery systems use methods and retroviruses that require transcription of the provirus and assembly into infectious virus while in the presence of an appropriate helper virus or in a cell line containing appropriate sequences enabling encapsidation without coincident production of a contaminating helper virus. As described below, a helper virus is not required for the production of the recombinant retrovirus of the disclosure, since the sequences for encapsidation are provided in the genome thus providing a replication competent retroviral vector for gene delivery or therapy.

Existing replication competent retroviral vectors also tend to lose inserted heterologous sequences from an infected cell or host cell during horizontal or vertical transmission and during replication. This may be due in-part from the presence of extra nucleotide sequences that include repeats or which reduce the efficiency of a polymerase.

The retroviral genome and the proviral DNA of the disclosure have at least three genes: the gag, the pol, and the env, these genes may be flanked by one or two long terminal (LTR) repeat, or in the provirus are flanked by two long terminal repeat (LTR) and sequences containing cis-acting sequences such as psi. The gag gene encodes the internal structural (matrix, capsid, and nucleocapsid) proteins; the pol gene encodes the RNA-directed DNA polymerase (reverse transcriptase), protease and integrase; and the env gene encodes viral envelope glycoproteins. The 5' and/or 3' LTRs serve to promote transcription and polyadenylation of the virion RNAs. The LTR contains all other cis-acting sequences necessary for viral replication. Lentiviruses have additional genes including vif, vpr, tat, rev, vpu, nef, and vpx (in HIV-1, HIV-2 and/or SIV).

Adjacent to the 5' LTR are sequences necessary for reverse transcription of the genome (the tRNA primer binding site) and for efficient encapsidation of viral RNA into particles (the Psi site). If the sequences necessary for encapsidation (or packaging of retroviral RNA into infectious virion) are missing from the viral genome, the result is a cis defect which prevents encapsidation of genomic viral RNA. This type of modified vector is what has typically been used in prior gene delivery systems (i.e., systems lacking elements which are required for encapsidation of the virion).

In a first embodiment, the disclosure provides a recombinant retrovirus capable of infecting a non-dividing cell, a dividing cell, or a cell having a cell proliferative disorder. The recombinant replication competent retrovirus of the disclosure comprises a polynucleotide sequence encoding a viral GAG, a viral POL, a viral ENV, a heterologous polynucleotide preceded by an internal ribosome entry site (IRES) encapsulated within a virion.

The phrase "non-dividing" cell refers to a cell that does not go through mitosis. Non-dividing cells may be blocked at any point in the cell cycle, (e.g., $G_0/G_1$, $G_{1/S}$, $G_{2/M}$), as long as the cell is not actively dividing. For ex vivo infection, a dividing cell can be treated to block cell division by standard techniques used by those of skill in the art, including, irradiation, aphidocolin treatment, serum starvation, and contact inhibition. However, it should be understood that ex vivo infection is often performed without blocking the cells since many cells are already arrested (e.g., stem cells). For example, a recombinant lentivirus vector is capable of infecting any non-dividing cell, regardless of the mechanism used to block cell division or the point in the cell cycle at which the cell is blocked. Examples of pre-existing non-dividing cells in the body include neuronal, muscle, liver, skin, heart, lung, and bone marrow cells, and their derivatives. For dividing cells onco-retroviral or gamma retroviral vectors can be used.

By "dividing" cell is meant a cell that undergoes active mitosis, or meiosis. Such dividing cells include stem cells, skin cells (e.g., fibroblasts and keratinocytes), gametes, and other dividing cells known in the art. Of particular interest and encompassed by the term dividing cell are cells having cell proliferative disorders, such as neoplastic cells. The term "cell proliferative disorder" refers to a condition characterized by an abnormal number of cells. The condition can include both hypertrophic (the continual multiplication of cells resulting in an overgrowth of a cell population within a tissue) and hypotrophic (a lack or deficiency of cells within a tissue) cell growth or an excessive influx or migration of cells into an area of a body. The cell populations are not necessarily transformed, tumorigenic or malignant cells, but can include normal cells as well. Cell proliferative disorders include disorders associated with an overgrowth of connective tissues, such as various fibrotic conditions, including scleroderma, arthritis and liver cirrhosis. Cell proliferative disorders include neoplastic disorders such as head and neck carcinomas. Head and neck carcinomas would include, for example, carcinoma of the mouth, esophagus, throat, larynx, thyroid gland, tongue, lips, salivary glands, nose, paranasal sinuses, nasopharynx, superior nasal vault and sinus tumors, esthesioneuroblastoma, squamous call cancer, malignant melanoma, sinonasal undifferentiated carcinoma (SNUC), brain (including glioblastomas) or blood neoplasia. Also included are carcinoma's of the regional lymph nodes including cervical lymph nodes, prelaryngeal lymph nodes, pulmonary juxtaesophageal lymph nodes and submandibular lymph nodes (Harrison's Principles of Internal Medicine (eds., Isselbacher, et al., McGraw-Hill, Inc., 13th Edition, pp 1850-1853, 1994). Other cancer types, include, but are not limited to, lung cancer, colon-rectum cancer, breast cancer, prostate cancer, urinary tract cancer, uterine cancer lymphoma, oral cancer, pancreatic cancer, leukemia, melanoma, stomach cancer, skin cancer and ovarian cancer. The cell proliferative disease also includes rheumatoid arthritis (O'Dell NEJM 350:2591 2004) and other auto-immune disorders (Mackay et al NEJM 345:340 2001) that are often characterized by inappropriate proliferation of cells of the immune system.

The heterologous nucleic acid sequence is operably linked to an IRES. As used herein, the term "heterologous" nucleic acid sequence or transgene refers to (i) a sequence that does not normally exist in a wild-type retrovirus, (ii) a sequence that originates from a foreign species, or (iii) if from the same species, it may be substantially modified from its original form. Alternatively, an unchanged nucleic acid sequence that is not normally expressed in a cell is a heterologous nucleic acid sequence.

Depending upon the intended use of the retroviral vector of the disclosure any number of heterologous polynucleotide or nucleic acid sequences may be inserted into the retroviral vector. For example, for in vitro studies commonly used marker genes or reporter genes may be used, including, antibiotic resistance and fluorescent molecules (e.g., GFP). Additional polynucleotide sequences encoding any desired polypeptide sequence may also be inserted into the vector of the disclosure. Where in vivo delivery of a heterologous nucleic acid sequence is sought both therapeutic and non-therapeutic sequences may be used. For example, the heterologous sequence can encode a therapeutic molecule including antisense molecules (miRNA, siRNA) or ribozymes directed to a particular gene associated with a cell proliferative disorder or other gene-associated disease or disorder, the heterologous sequence can be a suicide gene (e.g., HSV-tk or PNP or cytosine deaminase; either modified or unmodified), a growth factor or a therapeutic protein (e.g., Factor IX, IL2, and the like). Other therapeutic proteins applicable to the disclosure are easily identified in the art.

In one embodiment, the heterologous polynucleotide within the vector encodes a polypeptide having cytosine deaminase activity that has been optimized for expression in a human cell. In a further embodiment, the polynucleotide encoding the polypeptide having cytosine deaminase activity comprises a sequence that has been human codon optimized and comprises mutations that increase the cytosine deaminase's stability (e.g., reduced degradation or increased thermostability) compared to a wild-type cytosine deaminase. In yet another embodiment, the heterologous polynucleotide encodes a fusion construct comprising a polypeptide having cytosine deaminase activity (either human codon optimized or non-optimized, either mutated or non-mutated) operably linked to a polynucleotide encoding a polypeptide having UPRT or OPRT activity. In another embodiment, the heterologous polynucleotide comprises a CD polynucleotide.

In another embodiment, replication competent retroviral vector can comprise a heterologous polynucleotide encoding a polypeptide comprising a cytosine deaminase (as described herein) and may further comprise a polynucleotide comprising a miRNA or siRNA molecule either as part of the primary transcript from the viral promoter or linked to a promoter, which can be cell-type or tissue specific, or a pol III promoter.

MicroRNAs (miRNA) are small, non-coding RNAs. They are located within introns of coding or non-coding gene, exons of non-coding genes or in inter-genic regions. miRNA genes are transcribed by RNA polymerase II that generate precursor polynucleotides called primary precursor miRNA (pri-miRNA). The pri-miRNA in the nucleus is processed by the ribonuclease Drosha to produce the miRNA precursor (pre-miRNA) that forms a short hairpin structure. Subsequently, pre-miRNA is transported to the cytoplasma via Exportin 5 and further processed by another ribonuclease called Dicer to generate an active, mature miRNA.

A mature miRNA is approximately 21 nucleotides in length. It exerts in function by binding to the 3' untranslated region of mRNA of targeted genes and suppressing protein expression either by repression of protein translation or degradation of mRNA. miRNA are involved in biological processes including development, cell proliferation, differentiation and cancer progression. Studies of miRNA profiling indicate that some miRNA expressions are tissue specific or enriched in certain tissues. For example, miR-142-3p, miR-181 and miR-223 expressions have demonstrated to be enriched in hematopoietic tissues in human and mouse (Baskerville et al., 2005 *RNA* 11, 241-247; Chen et al., 2004 *Science* 303, 83-86).

Some miRNAs have been observed to be up-regulated (oncogenic miRNA) or down-regulated (repressor) in several tumors (Spizzo et al., *Cell* 137, 586e1, 2009). For example, miR-21 is overexpressed in glioblastoma, breast, lung, prostate, colon, stomach, esophageal, and cervical cancer, uterine leiomyosarcoma, DLBCL, head and neck cancer. In contrast, members of let-7 have reported to be down-regulated in glioblastoma, lung, breast, gastric, ovary, prostate and colon cancers. Re-establishment of homeostasis of miRNA expression in cancer is an important mechanism to inhibit or reverse cancer progression.

As a consequence of the vital functions modulated by miRNAs in cancers, focus in developing potential therapeutic approaches has been directed toward antisense-mediated inhibition (antigomers) of oncogenic miRNAs. However, miRNA replacement might represent an equally efficacious strategy. In this approach, the most therapeutically useful miRNAs are the ones expressed at low levels in tumors but at high level, and therefore tolerated, in normal tissues.

miRNAs that are down-regulated in cancers can be useful as anticancer agents. Examples include mir-128-1, let-7, miR-26, miR-124, and miR-137 (Esquela-Kerscher et al., 2008 *Cell Cycle* 7, 759-764; Kumar et al., 2008 *Proc Natl Acad Sci USA* 105, 3903-3908; Kota et al., 2009 *Cell* 137, 1005-1017; Silber et al., 2008 BMC Medicine 6:14 1-17). miR-128 expression has reported to be enriched in the central nervous system and has been observed to be down-regulated in glioblastomas (Sempere et al., 2004 *Genome Biology* 5:R13.5-11; Godlewski et al., 2008 *Cancer Res* 68: (22) 9125-9130). miR-128 is encoded by two distinct genes, miR-128-1 and miR-128-2. Both are processed into identical mature sequence. Bmi-1 and E2F3a have been reported to be the direct targets of miR-128 (Godlewski et al., 2008 *Cancer Res* 68: (22) 9125-9130; Zhang et al., 2009 *J. Mol. Med* 87:43-51). In addition, Bmi-1 expression has been observed to be up-regulated in a variety of human cancers, including gliomas, mantle cell lymphomas, non-small cell lung cancer B-cell non-Hodgkin's lymphoma, breast, colorectal and prostate cancer. Furthermore, Bmi-1 has been demonstrated to be required for the self-renewal of stem cells from diverse tissues, including neuronal stem cells as well as "stem-like" cell population in gliomas.

In one embodiment, the disclosure provides a recombinant replication competent retroviral vector that contains a heterologous polynucleotide sequence of a primary precursor miRNA. In a further embodiment the primary precursor miRNA is of human origin. In another embodiment the primary precursor RNA sequence is downstream of the env gene.

In another embodiment, the disclosure provides a recombinant replication competent retroviral vector that contains a heterologous polynucleotide sequence of the human primary precursor miR-128-2 downstream of the env gene. miRNAs that are down-regulated in cancers can be incorporated into the vector for therapeutic gene delivery. For example, let-7, miR-26, miR-124, and miR-137 (Esquela-Kerscher et al., 2008 *Cell Cycle* 7, 759-764; Kumar et al., 2008 *Proc Natl Acad Sci USA* 105, 3903-3908; Kota et al., 2009 *Cell* 137, 1005-1017; Silber et al., 2008 *BMC Medicine* 6:14 1-17).

In yet another embodiment, the disclosure provides a recombinant replication competent retroviral vector that contains a heterologous polynucleotide sequence of the short hairpin structured human pre-miR-128 linked to a human H1 promoter downstream (i.e., 3') of the env gene. miRNAs that are down-regulated in cancers can be incorporated into the vector for therapeutic gene delivery. For example, let-7, miR-26, miR-124, and miR-137 (Esquela-Kerscher et al., 2008 *Cell Cycle* 7, 759-764; Kumar et al., 2008 *Proc Natl Acad Sci USA* 105, 3903-3908; Kota et al., 2009 *Cell* 137, 1005-1017; Silber et al., 2008 *BMC Medicine* 6:14 1-17).

Antisense nucleic acids are DNA or RNA molecules that are complementary to at least a portion of a specific mRNA molecule (Weintraub, Scientific American, 262:40, 1990). In the cell, the antisense nucleic acids hybridize to the corresponding mRNA, forming a double-stranded molecule. The antisense nucleic acids interfere with the translation of the mRNA, since the cell will not translate a mRNA that is double-stranded. Antisense oligomers of about 15 nucleotides are preferred, since they are easily synthesized and are less likely to cause problems than larger molecules when introduced into the target cell. The use of antisense methods to inhibit the in vitro translation of genes is well known in the art (Marcus-Sakura, Anal. Biochem., 172:289, 1988).

The antisense nucleic acid can be used to block expression of a mutant protein or a dominantly active gene product, such as amyloid precursor protein that accumulates in Alzheimer's disease. Such methods are also useful for the treatment of Huntington's disease, hereditary Parkinsonism, and other diseases. Of particular interest is the blocking of genes associated with cell-proliferative disorders. Antisense nucleic acids are also useful for the inhibition of expression of proteins associated with toxicity.

Use of an oligonucleotide to stall transcription is known as the triplex strategy since the oligomer winds around double-helical DNA, forming a three-strand helix. Therefore, these triplex compounds can be designed to recognize a unique site on a chosen gene (Maher, et al., Antisense Res. and Dev., 1(3):227, 1991; Helene, C., Anticancer Drug Design, 6(6):569, 1991).

Ribozymes are RNA molecules possessing the ability to specifically cleave other single-stranded RNA in a manner analogous to DNA restriction endonucleases. Through the modification of nucleotide sequences which encode these RNAs, it is possible to engineer molecules that recognize specific nucleotide sequences in an RNA molecule and cleave it (Cech, J. Amer. Med. Assn., 260:3030, 1988). A major advantage of this approach is that, because they are sequence-specific, only mRNAs with particular sequences are inactivated.

As used herein, the term "RNA interference" (RNAi) refers to the process of sequence-specific post-transcriptional gene silencing mediated by short interfering nucleic acids (siRNAs or microRNAs (miRNA)). The term "agent capable of mediating RNA interference" refers to siRNAs as well as DNA and RNA vectors that encode siRNAs when transcribed within a cell. The term siRNA or miRNA is meant to encompass any nucleic acid molecule that is capable of mediating sequence specific RNA interference, for example short interfering RNA (siRNA), double-stranded RNA (dsRNA), micro-RNA (miRNA), short hairpin RNA (siRNA), short interfering oligonucleotide, short interfering nucleic acid, short interfering modified oligonucleotide, chemically-modified siRNA, post-transcriptional gene silencing RNA (ptgsRNA), and others.

Suitable range for designing stem lengths of a hairpin duplex, includes stem lengths of 20-30 nucleotides, 30-50 nucleotides, 50-100 nucleotides, 100-150 nucleotides, 150-200 nucleotides, 200-300 nucleotides, 300-400 nucleotides, 400-500 nucleotides, 500-600 nucleotides, and 600-700 nucleotides. Suitable range for designing loop lengths of a hairpin duplex, includes loop lengths of 4-25 nucleotides, 25-50 nucleotides, or longer if the stem length of the hair duplex is substantial. In certain context, hairpin structures with duplexed regions that are longer than 21 nucleotides may promote effective siRNA-directed silencing, regardless of the loop sequence and length.

The replicating retroviral vectors of the disclosure can be used to treat disease by expressing engineered siRNA or miRNA (Dennis, Nature, 418:122, 2002) that switches off or lowers expression of key genes that govern the proliferation or survival of diseased cells including tumor cells. Such targets include genes like Rad 51 a central enzyme in DNA repair, and without which cell growth is drastically restricted. For example inhibition of DNA repair by siRNA or other mechanisms provides more potent and/or durable therapy than the radiation alone after treatment of a neoplasm with radiation therapy. Other targets include many of the signaling pathway molecules that control cell growth (Marquez & McCaffrey Hum Gene Ther. 19:27 2008). The siRNA or miRNA may be combined with expression of a cytotoxic gene from the same or different retroviral vector of the disclosure. An example of a suitable cytotoxic gene comprise a cytosine deaminase or modified cytosine deaminase of the disclosure.

In use, the retroviral vector(s) will replicate through the tumor or other target tissue and before growth inhibition occurs the virus first integrates into the host genome and continues to make virus after growth of that cell is inhibited. Methods for selecting functional miRNA or siRNA sequences are known in the art. Key feature in general in designing effective siRNA or miRNA sequences is usually avoiding "off-target" effects. However for the use of replicating vectors that are highly specific to tumor cells such as those of the disclosure, these side effects are not very important, as the cells are expected to eventually die. A retroviral vector of this disclosure can be made using cells from other species for which the corresponding protein is not significantly targeted. Such cells include dog cell lines or chicken cell line. Alternatively the virus is made by transient transfection on human 293 derived cells or other cell line that allows efficient transient transfection. For this use the virus does not need to utilize an IRES, and the siRNA or miRNA sequence can simply be inserted at a convenient site on the viral genome. This site includes the region downstream of the envelope and upstream of the 3'LTR of the replicating retrovirus. Alternatively polIII transcription units can be inserted in the viral genome with the appropriate siRNA or miRNA's, typically downstream of the 3' envelope gene. Several different siRNA or miRNA sequences can be inserted to ensure efficient down regulation of the target gene or down regulation of more than one gene. Suitable sequences and targets can be obtained from sources known to those skilled in the art. For example:

The MIT/ICBP siRNA Database http:(//)web.mit.edu/sirna/—"The MIT [Massachusetts Institute of Technology]/ICBP [Integrative Cancer Biology Program] siRNA Database is a university-wide effort to catalog these experimentally validated reagents and make that information available to other researchers, both within and outside the MIT community. (Massachusetts Institute of Technology).

RNAi Central—http:(//)katandin.cshl.org:9331/RNAi_web/scripts/main2.pl RNAi resources, including siRNA and shRNA design tools. (Hannon Lab, Cold Spring Harbor Laboratory)

The RNAi Web—http:(//)www.rnaiweb.com/ General resource.

siDIRECT—http:(//)genomics.jp/sidirect/ Online target-specific siRNA design program for mammalian RNA interference. (University of Tokyo, Japan).

siRNA Database—A comprehensive siRNA database that contains siRNA targets against all known mRNA sequences throughout a variety of organisms. (Part of the Protein Lounge systems biology Web site)

siRNA Database and Resources for RNA Interference Studies http:(//)www.rnainterference.org/ siRNA Selector—http:(//)bioinfo.wistar.upenn.edu/siRNA/siRNA.htm. A set of rules was used for evaluating siRNA functionality based on thermodynamics parameters (Khvorova et al., 2003, Schwarz et al., 2003) and sequence-related determinants developed by Dharmacon (Reynolds et al., 2004). Specificity is determined using BLAST against UniGene databases. (Wistar Institute)

siRNA Target Finder http:(//)www(.)ambion.com/techlib/misc/siRNA_finder.html (Ambion).

The replicating retroviruses of the disclosure can also express targets for naturally occurring siRNA's that are restricted in expression to particular cell types so that replication of the vector is significantly inhibited in those cell types. The generation of murine leukemia virus-based recombinant replication competent retroviral vector allows high level of transduction and thus high efficiency of gene delivery in vivo. One major concern of using replication competent retroviral vector has been the uncontrolled spread of virus as reported previously (Donahue et al., *J. Exp Med.* 1992, 176:1124-1135; Calmes et al., *Blood* 2005, 106: 2530-2533; Seggewiss et al., *Blood* 2006, 107: 3865-3867). Because of the nature of the virus, the viral spread may be achieved initially within lymphatic cells and subsequently spread to peripheral tissues. For anti-tumor purposes some normal cells in the body that are naturally replicating at some level are hematopoietic cells, cells of the lining of the gut, and some endothelial cells. These are then potential sites where virus that is in the circulation could productively infect. In general this would be undesirable. Any stray infection of cells such as these can be inhibited by including a target for naturally occurring miRNA's or for a combination of miRNA's in these cell types. Some feasibility of using miRNA targets to suppress immune responses has already been shown. (Brown et al. Nat. Biotechnol. 2007 25:1457-67). These targets are small RNA sequences with a homologous match to the miRNA sequences that are naturally occurring. These sequences can be inserted in any convenient site in the vectors of the current invention without, in general significant deleterious consequence for vector viability, other than in a cell of the type desired. Vectors can be made and used as described herein.

In one embodiment, the disclosure provides a recombinant replication competent retroviral vector that contains a single copy of the miR-142-3p target sequence (142-3pT) downstream of the transgene, such as polynucleotide encoding a polypeptide having cytosine deaminase activity (e.g., yCD2) or GFP, linked to an IRES. In addition to miR181 and miR-223, the target sequence of other tissue or cell-enriched miRNA can be incorporated into the vector to restrict viral spread in specific tissue or cell type manner. For example, miR-133 and miR206 expressions are highly enriched in muscle cells (Kelly et al., 2008 Nature Medicine 14:11 1278-1283.

In another embodiment, the disclosure provides a recombinant replication competent retroviral vector that contains 4 copies of the 142-3pT downstream of the transgene, such as a cytosine deaminase or GFP, linked to the IRES. In addition to miR181 and miR-223, the target sequence of other tissue or cell-enriched miRNA can be incorporated into the vector to restrict viral spread in specific tissue or cell type manner. For example, miR-133 and miR206 expressions are highly enriched in muscle cells. The disclosure provides flexibility of single, multiple or combination of target sequence of miRNA and thereby provides restriction of uncontrolled viral spread in a tissue- and/or cell-specific fashion in vitro and in vivo (e.g. hematopoietic and/or muscle cells), (Kelly et al., 2008 Nature Medicine 14:11 1278-1283).

The miRNA target can be inserted 3' to the transgene but before the 3'LTR or upstream of the IRES but after the 3' end of the envelope. In general the target would not be inserted into protein coding sequences.

In yet further embodiments, the heterologous polynucleotide may comprise a cytokine such as an interleukin, interferon gamma or the like. Cytokines that may expressed from a retroviral vector of the disclosure include, but are not limited to, IL-1alpha, IL-1beta, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, and IL-21, anti-CD40, CD40L, IFN-gamma and TNF-alpha, soluble forms of TNF-alpha, lymphotoxin-alpha (LT-alpha, also known as TNF-beta), LT-beta (found in complex heterotrimer LT-alpha2-beta), OPGL, FasL, CD27L, CD30L, CD40L, 4-1BBL, DcR3, OX40L, TNF-gamma (International Publication No. WO 96/14328), AIM-I (International Publication No. WO 97/33899), endokine-alpha (International Publication No. WO 98/07880), OPG, and neutrokine-alpha (International Publication No. WO 98/18921, OX40, and nerve growth factor (NGF), and soluble forms of Fas, CD30, CD27, CD40 and 4-IBB, TR2 (International Publication No. WO 96/34095), DR3 (International Publication No. WO 97/33904), DR4 (International Publication No. WO 98/32856), TR5 (International Publication No. WO 98/30693), TRANK, TR9 (International Publication No. WO 98/56892), TR10 (International Publication No. WO 98/54202), 312C2 (International Publication No. WO 98/06842), and TR12, and soluble forms CD154, CD70, and CD153. Angiogenic proteins may be useful in some embodiments, particularly for protein production from cell lines. Such angiogenic factors include, but are not limited to, Glioma Derived Growth Factor (GDGF), Platelet Derived Growth Factor-A (PDGF-A), Platelet Derived Growth Factor-B (PDGF-B), Placental Growth Factor (PIGF), Placental Growth Factor-2 (PIGF-2), Vascular Endothelial Growth Factor (VEGF), Vascular Endothelial Growth Factor-A (VEGF-A), Vascular Endothelial Growth Factor-2 (VEGF-2), Vascular Endothelial Growth Factor B (VEGF-3), Vascular Endothelial Growth Factor B-1 86 (VEGF-B186), Vascular Endothelial Growth Factor-D (VEGF-D), Vascular Endothelial Growth Factor-D (VEGF-D), and Vascular Endothelial Growth Factor-E (VEGF-E). Fibroblast Growth Factors may be delivered by a vector of the disclosure and include, but are not limited to, FGF-1, FGF-2, FGF-3, FGF-4, FGF-5, FGF-6, FGF-7, FGF-8, FGF-9, FGF-10, FGF-11, FGF-12, FGF-13, FGF-14, and FGF-15. Hematopoietic growth factors may be delivered using vectors of the disclosure, such growth factors include, but are not limited to, granulocyte macrophage colony stimulating factor (GM-CSF) (sargramostim), granulocyte colony stimulating factor (G-CSF) (filgrastim), macrophage colony stimulating factor (M-CSF, CSF-1) erythropoietin (epoetin alfa), stem cell factor (SCF, c-kit ligand, steel factor), megakaryocyte colony stimulating factor, PIXY321 (a GMCSF/IL-3) fusion protein and the like.

The term "regulatory nucleic acid sequence" refers collectively to promoter sequences, polyadenylation signals, transcription termination sequences, upstream regulatory domains, origins of replication, enhancers and the like, which collectively provide for the replication, transcription and translation of a coding sequence in a recipient cell. Not all of these control sequences need always be present so long as the selected coding sequence is capable of being replicated, transcribed and translated in an appropriate host cell. One skilled in the art can readily identify regulatory nucleic acid sequence from public databases and materials. Furthermore, one skilled in the art can identify a regulatory sequence that is applicable for the intended use, for example, in vivo, ex vivo, or in vitro.

An internal ribosome entry sites ("IRES") refers to a segment of nucleic acid that promotes the entry or retention of a ribosome during translation of a coding sequence usually 3' to the IRES. In some embodiments the IRES may comprise a splice acceptor/donor site, however, preferred IRESs lack a splice acceptor/donor site. Normally, the entry of ribosomes into messenger RNA takes place via the cap located at the 5' end of all eukaryotic mRNAs. However, there are exceptions to this universal rule. The absence of a cap in some viral mRNAs suggests the existence of alternative structures permitting the entry of ribosomes at an internal site of these RNAs. To date, a number of these structures, designated IRES on account of their function, have been identified in the 5' noncoding region of uncapped viral mRNAs, such as that, in particular, of picornaviruses such as the poliomyelitis virus (Pelletier et al., 1988, Mol. Cell. Biol., 8, 1103-1112) and the EMCV virus (encephalomyocarditis virus (Jang et al., J. Virol., 1988, 62, 2636-2643). The disclosure provides the use of an IRES in the context of a replication-competent retroviral vector.

The term "promoter region" is used herein in its ordinary sense to refer to a nucleotide region comprising a DNA regulatory sequence, wherein the regulatory sequence is derived from a gene which is capable of binding RNA polymerase and initiating transcription of a downstream (3'-direction) coding sequence. The regulatory sequence may be homologous or heterologous to the desired gene sequence. For example, a wide range of promoters may be utilized, including viral or mammalian promoter as described above.

The heterologous nucleic acid sequence is typically under control of either the viral LTR promoter-enhancer signals or an internal promoter, and retained signals within the retroviral LTR can still bring about efficient integration of the vector into the host cell genome. Accordingly, the recombinant retroviral vectors of the disclosure, the desired sequences, genes and/or gene fragments can be inserted at several sites and under different regulatory sequences. For example, a site for insertion can be the viral enhancer/promoter proximal site (i.e., 5' LTR-driven gene locus). Alternatively, the desired sequences can be inserted into a regulatory sequence distal site (e.g., the IRES sequence 3' to the env gene) or where two or more heterologous sequences are present one heterologous sequence may be under the control of a first regulatory region and a second heterologous sequence under the control of a second regulatory region. Other distal sites include viral promoter sequences, where the expression of the desired sequence or sequences is through splicing of the promoter proximal cistron, an internal heterologous promoter as SV40 or CMV, or an internal ribosome entry site (IRES) can be used.

In another embodiment, a targeting polynucleotide sequence is included as part of the recombinant retroviral vector of the disclosure. The targeting polynucleotide sequence is a targeting ligand (e.g., peptide hormones such as heregulin, a single-chain antibodies, a receptor or a ligand for a receptor), a tissue-specific or cell-type specific regulatory element (e.g., a tissue-specific or cell-type specific promoter or enhancer), or a combination of a targeting ligand and a tissue-specific/cell-type specific regulatory element. Preferably, the targeting ligand is operably linked to the env protein of the retrovirus, creating a chimeric retroviral env protein. The viral GAG, viral POL and viral ENV proteins can be derived from any suitable retrovirus (e.g., MLV or lentivirus-derived). In another embodiment, the viral ENV protein is non-retrovirus-derived (e.g., CMV or VSV).

In one embodiment, the recombinant retrovirus of the disclosure is genetically modified in such a way that the virus is targeted to a particular cell type (e.g., smooth muscle cells, hepatic cells, renal cells, fibroblasts, keratinocytes, mesenchymal stem cells, bone marrow cells, chondrocyte, epithelial cells, intestinal cells, mammary cells, neoplastic cells, glioma cells, neuronal cells and others known in the art) such that the recombinant genome of the retroviral vector is delivered to a target non-dividing, a target dividing cell, or a target cell having a cell proliferative disorder.

In one embodiment, the retroviral vector is targeted to the cell by binding to cells having a molecule on the external surface of the cell. This method of targeting the retrovirus utilizes expression of a targeting ligand on the coat of the retrovirus to assist in targeting the virus to cells or tissues that have a receptor or binding molecule which interacts with the targeting ligand on the surface of the retrovirus. After infection of a cell by the virus, the virus injects its nucleic acid into the cell and the retrovirus genetic material can integrate into the host cell genome.

In another embodiment, targeting uses cell- or tissue-specific regulatory elements to promote expression and transcription of the viral genome in a targeted cell which actively utilizes the regulatory elements, as described more fully below. The transferred retrovirus genetic material is then transcribed and translated into proteins within the host cell. The targeting regulatory element is typically linked to the 5' and/or 3' LTR, creating a chimeric LTR.

By inserting a heterologous polynucleotide of interest into the viral vector of the disclosure, along with another gene which encodes, for example, the ligand for a receptor on a specific target cell, the vector is now target specific. Viral vectors can be made target specific by attaching, for example, a sugar, a glycolipid, or a protein. Targeting can be accomplished by using an antibody to target the viral vector. Those of skill in the art will know of, or can readily ascertain, specific polynucleotide sequences which can be inserted into the viral genome or proteins which can be attached to a viral envelope to allow target specific delivery of the viral vector containing the nucleic acid sequence of interest.

Thus, the disclosure includes in one embodiment, a chimeric env protein comprising a retroviral ENV protein operably linked to a targeting polypeptide. The targeting polypeptide can be a cell specific receptor molecule, a ligand for a cell specific receptor, an antibody or antibody fragment to a cell specific antigenic epitope or any other ligand easily identified in the art which is capable of binding or interacting with a target cell. Examples of targeting polypeptides or molecules include bivalent antibodies using biotin-streptavidin as linkers (Etienne-Julan et al., J. Of General Virol., 73, 3251-3255 (1992); Roux et al., Proc. Natl. Acad. Sci. USA 86, 9079-9083 (1989)), recombinant virus containing in its envelope a sequence encoding a single-chain antibody variable region against a hapten (Russell et al., Nucleic Acids Research, 21, 1081-1085 (1993)), cloning of peptide hormone ligands into the retrovirus envelope (Kasahara et al., Science, 266, 1373-1376 (1994)), chimeric EPO/env constructs (Kasahara et al., 1994), single-chain antibody against the low density lipoprotein (LDL) receptor in the ecotropic MLV envelope, resulting in specific infection of HeLa cells expressing LDL receptor (Somia et al., Proc. Natl. Acad. Sci. USA, 92, 7570-7574 (1995)), similarly the host range of ALV can be altered by incorporation of an integrin ligand, enabling the virus to now cross species to specifically infect rat glioblastoma cells (Valsesia-Wittmann et al., J. Virol. 68, 4609-4619 (1994)), and Dornberg and co-workers (Chu and Dornburg, J. Virol 69, 2659-2663 (1995)) have reported tissue-specific targeting of spleen necrosis virus (SNV), an avian retrovirus, using envelopes containing single-chain antibodies directed against tumor markers.

The disclosure provides a method of producing a recombinant retrovirus capable of infecting a target cell comprising transfecting a suitable host cell with the following: a vector comprising a polynucleotide sequence encoding a viral gag, a viral pol and a viral env, and a heterologous polynucleotide, operably linked to a regulatory nucleic acid sequence, and recovering the recombinant virus.

The retrovirus and methods of the disclosure provide a replication competent retrovirus that does not require helper virus or additional nucleic acid sequence or proteins in order to propagate and produce virion. For example, the nucleic acid sequences of the retrovirus of the disclosure encode, for example, a group specific antigen and reverse transcriptase, (and integrase and protease-enzymes necessary for maturation and reverse transcription), respectively, as discussed above. The viral gag and pol can be derived from a lentivirus, such as HIV or an oncovirus or gammaretrovirus such as MoMLV. In addition, the nucleic acid genome of the retrovirus of the disclosure includes a sequence encoding a viral envelope (ENV) protein. The env gene can be derived from any retroviruses. The env may be an amphotropic envelope protein which allows transduction of cells of human and other species, or may be an ecotropic envelope protein, which is able to transduce only mouse and rat cells. Further, it may be desirable to target the recombinant virus by linkage of the envelope protein with an antibody or a particular ligand for targeting to a receptor of a particular cell-type. As mentioned above, retroviral vectors can be made target specific by inserting, for example, a glycolipid, or a protein. Targeting is often accomplished by using an antibody to target the retroviral vector to an antigen on a particular cell-type (e.g., a cell type found in a certain tissue, or a cancer cell type). Those of skill in the art will know of, or can readily ascertain without undue experimentation, specific methods to achieve delivery of a retroviral vector to a specific target. In one embodiment, the env gene is derived from a non-retrovirus (e.g., CMV or VSV). Examples of retroviral-derived env genes include, but are not limited to: Moloney murine leukemia virus (MoMuLV), Harvey murine sarcoma virus (HaMuSV), murine mammary tumor virus (MuMTV), gibbon ape leukemia virus (GaLV), human immunodeficiency virus (HIV) and Rous Sarcoma Virus (RSV). Other env genes such as Vesicular stomatitis virus (VSV) (Protein G), cytomegalovirus envelope (CMV), or influenza virus hemagglutinin (HA) can also be used.

In one embodiment, the retroviral genome is derived from an onco-retrovirus or gamma-retrovirus, and more particularly a mammalian onco-retrovirus or gamma-retrovirus. By "derived" is meant that the parent polynucleotide sequence is an wild-type oncovirus which has been modified by insertion or removal of naturally occurring sequences (e.g., insertion of an IRES, insertion of a heterologous polynucleotide encoding a polypeptide or inhibitory nucleic acid of interest, swapping of a more effective promoter from a different retrovirus or virus in place of the wild-type promoter and the like).

Unlike recombinant retroviruses produced by standard methods in the art that are defective and require assistance in order to produce infectious vector particles, the disclosure provides a retrovirus that is replication-competent.

In another embodiment, the disclosure provides retroviral vectors that are targeted using regulatory sequences. Cell- or tissue-specific regulatory sequences (e.g., promoters) can be utilized to target expression of gene sequences in specific cell populations. Suitable mammalian and viral promoters for the disclosure are described elsewhere herein. Accordingly, in one embodiment, the disclosure provides a retrovirus having tissue-specific promoter elements at the 5' end of the retroviral genome. Typically, the tissue-specific regulatory elements/sequences are in the U3 region of the LTR of the retroviral genome, including for example cell- or tissue-specific promoters and enhancers to neoplastic cells (e.g., tumor cell-specific enhancers and promoters), and inducible promoters (e.g., tetracycline).

Transcription control sequences of the disclosure can also include naturally occurring transcription control sequences naturally associated with a gene encoding a superantigen, a cytokine or a chemokine.

In some circumstances, it may be desirable to regulate expression. For example, different viral promoters with varying strengths of activity may be utilized depending on the level of expression desired. In mammalian cells, the CMV immediate early promoter if often used to provide strong transcriptional activation. Modified versions of the CMV promoter that are less potent have also been used when reduced levels of expression of the transgene are desired. When expression of a transgene in hematopoietic cells is desired, retroviral promoters such as the LTRs from MLV or MMTV can be used. Other viral promoters that can be used include SV40, RSV LTR, HIV-1 and HIV-2 LTR, adenovirus promoters such as from the E1A, E2A, or MLP region, AAV LTR, cauliflower mosaic virus, HSV-TK, and avian sarcoma virus.

Similarly tissue specific or selective promoters may be used to effect transcription in specific tissues or cells so as to reduce potential toxicity or undesirable effects to non-targeted tissues. For example, promoters such as the PSA, probasin, prostatic acid phosphatase or prostate-specific glandular kallikrein (hK2) may be used to target gene expression in the prostate. The Whey accessory protein (WAP) may be used for breast tissue expression (Andres et al., PNAS 84:1299-1303, 1987). Other promoters/regulatory domains that can be used are set forth in Table 4.

"Tissue-specific regulatory elements" are regulatory elements (e.g., promoters) that are capable of driving transcription of a gene in one tissue while remaining largely "silent" in other tissue types. It will be understood, however, that tissue-specific promoters may have a detectable amount of "background" or "base" activity in those tissues where they are silent. The degree to which a promoter is selectively activated in a target tissue can be expressed as a selectivity ratio (activity in a target tissue/activity in a control tissue). In this regard, a tissue specific promoter useful in the practice of the disclosure typically has a selectivity ratio of greater than about 5. Preferably, the selectivity ratio is greater than about 15.

In certain indications, it may be desirable to activate transcription at specific times after administration of the recombinant replication competent retrovirus of the disclosure (RRCR). This may be done with promoters that are hormone or cytokine regulatable. For example in therapeutic applications where the indication is a gonadal tissue where specific steroids are produced or routed to, use of androgen or estrogen regulated promoters may be advantageous. Such promoters that are hormone regulatable include MMTV, MT-1, ecdysone and RuBisco. Other hormone regulated promoters such as those responsive to thyroid, pituitary and adrenal hormones may be used. Cytokine and inflammatory protein responsive promoters that could be used include K and T Kininogen (Kageyama et al., 1987), c-fos, TNF-alpha, C-reactive protein (Arcone et al., 1988), haptoglobin (Oliviero et al., 1987), serum amyloid A2, C/EBP alpha, IL-1, IL-6 (Poli and Cortese, 1989), Complement C3 (Wilson et al., 1990), IL-8, alpha-1 acid glycoprotein (Prowse and Baumann, 1988), alpha-1 antitrypsin, lipoprotein lipase (Zechner et al., 1988), angiotensinogen (Ron et al., 1990), fibrinogen, c-jun (inducible by phorbol esters, TNF-alpha, UV radiation, retinoic acid, and hydrogen peroxide), collagenase (induced by phorbol esters and retinoic acid), metallothionein (heavy metal and glucocorticoid inducible), Stromelysin (inducible by phorbol ester, interleukin-1 and EGF), alpha-2 macroglobulin and alpha-1 antichymotrypsin. Tumor specific promoters such as osteocalcin, hypoxia-responsive element (HRE), MAGE-4, CEA, alpha-fetoprotein, GRP78/BiP and tyrosinase may also be used to regulate gene expression in tumor cells.

In addition, this list of promoters should not be construed to be exhaustive or limiting, those of skill in the art will know of other promoters that may be used in conjunction with the promoters and methods disclosed herein.

TABLE 4

TISSUE SPECIFIC PROMOTERS

| Tissue | Promoter |
| --- | --- |
| Pancreas | Insulin Elastin Amylase pdr-1 pdx-1 glucokinase |
| Liver | Albumin PEPCK HBV enhancer α fetoprotein apolipoprotein C α-1 antitrypsin vitellogenin, NF-AB Transthyretin |
| Skeletal muscle | Myosin H chain Muscle creatine kinase Dystrophin Calpain p94 Skeletal alpha-actin fast troponin 1 |
| Skin | Keratin K6 Keratin K1 |
| Lung | CFTR Human cytokeratin 18 (K18) Pulmonary surfactant proteins A, B and C CC-10 P1 |
| Smooth muscle | sm22 α SM-alpha-actin |
| Endothelium | Endothelin-1 E-selectin von Willebrand factor TIE (Korhonen et al., 1995) KDR/flk-1 Melanocytes Tyrosinase |
| Adipose tissue | Lipoprotein lipase (Zechner et al., 1988) Adipsin (Spiegelman et al., 1989) acetyl-CoA carboxylase (Pape and Kim, 1989) glycerophosphate dehydrogenase (Dani et al., 1989) adipocyte P2 (Hunt et al., 1986) |
| Breast | Whey Acidic Protien (WAP)(Andres et al. PNAS 84: 1299-1303 1987 |
| Blood | β-globin |

It will be further understood that certain promoters, while not restricted in activity to a single tissue type, may nevertheless show selectivity in that they may be active in one group of tissues, and less active or silent in another group. Such promoters are also termed "tissue specific", and are contemplated for use with the disclosure. For example, promoters that are active in a variety of central nervous system (CNS) neurons may be therapeutically useful in protecting against damage due to stroke, which may effect any of a number of different regions of the brain. Accordingly, the tissue-specific regulatory elements used in the disclosure, have applicability to regulation of the heterologous proteins as well as a applicability as a targeting polynucleotide sequence in the present retroviral vectors.

In yet another embodiment, the disclosure provides plasmids comprising a recombinant retroviral derived construct. The plasmid can be directly introduced into a target cell or a cell culture such as NIH 3T3 or other tissue culture cells. The resulting cells release the retroviral vector into the culture medium.

The disclosure provides a polynucleotide construct comprising from 5' to 3': a promoter or regulatory region useful for initiating transcription; a psi packaging signal; a gag encoding nucleic acid sequence, a pol encoding nucleic acid sequence; an env encoding nucleic acid sequence; an internal ribosome entry site nucleic acid sequence; a heterologous polynucleotide encoding a marker, therapeutic or diagnostic polypeptide; and a LTR nucleic acid sequence. As described elsewhere herein and as follows the various segment of the polynucleotide construct of the disclosure (e.g., a recombinant replication competent retroviral polynucleotide) are engineered depending in part upon the desired host cell, expression timing or amount, and the heterologous polynucleotide. A replication competent retroviral construct of the disclosure can be divided up into a number of domains that may be individually modified by those of skill in the art.

For example, the promoter can comprise a CMV promoter having a sequence as set forth in SEQ ID NO:1, 2 or 3 from nucleotide 1 to about nucleotide 582 and may include modification to one or more (e.g., 2-5, 5-10, 10-20, 20-30, 30-50, 50-100 or more nucleic acid bases) so long as the modified promoter is capable of directing and initiating transcription. In one embodiment, the promoter or regulatory region comprises a CMV-R-U5 domain polynucleotide. The CMV-R-U5 domain comprises the immediately early promoter from human cytomegalovirus to the MLV R-U5 region. In one embodiment, the CMV-R-U5 domain polynucleotide comprises a sequence as set forth in SEQ ID NO:1, 2, or 3 from about nucleotide 1 to about nucleotide 1202 or sequences that are at least 95% identical to a sequence as set forth in SEQ ID NO:1, 2, or 3 wherein the polynucleotide promotes transcription of a nucleic acid molecule operably linked thereto. The gag domain of the polynucleotide may be derived from any number of retroviruses, but will typically be derived from an oncoretrovirus and more particularly from a mammalian oncoretrovirus. In one embodiment the gag domain comprises a sequence from about nucleotide number 1203 to about nucleotide 2819 or a sequence having at least 95%, 98%, 99% or 99.8% (rounded to the nearest $10^{th}$) identity thereto. The pol domain of the polynucleotide may be derived from any number of retroviruses, but will typically be derived from an oncoretrovirus and more particularly from a mammalian oncoretrovirus. In one embodiment the pol domain comprises a sequence from about nucleotide number 2820 to about nucleotide 6358 or a sequence having at least 95%, 98%, 99% or 99.9% (roundest to the nearest $10^{th}$) identity thereto. The env domain of the polynucleotide may be derived from any number of retroviruses, but will typically be derived from an oncoretrovirus or gamma-retrovirus and more particularly from a mammalian oncoretrovirus or gamma-retrovirus. In some embodiments the env coding domain comprises an amphotropic env domain. In one embodiment the env domain comprises a sequence from about nucleotide number 6359 to about nucleotide 8323 or a sequence having at least 95%, 98%, 99% or 99.8% (roundest to the nearest $10^{th}$) identity thereto. The IRES domain of the polynucleotide may be obtained from any number of internal ribosome entry sites. In one embodiment, IRES is derived from an encephalomyocarditis virus. In one embodiment the IRES domain comprises a sequence from about nucleotide number 8327 to about nucleotide 8876 or a sequence having at least 95%, 98%, or 99% (roundest to the nearest $10^{th}$) identity thereto so long as the domain allows for entry of a ribosome. The heterologous domain can comprise a cytosine deaminase of the disclosure. In one embodiment, the CD polynucleotide comprises a human codon optimized sequence. In yet another embodiment, the CD polynucleotide encodes a mutant polypeptide having cytosine deaminase, wherein the mutations confer increased thermal stabilization that increase the melting temperature (Tm) by 10° C. allowing sustained kinetic activity over a broader temperature range and increased accumulated levels of protein. In one embodiment, the cytosine deaminase comprises a sequence as set forth in SEQ ID NO:1 or 3 from about nucleotide number 8877 to about 9353. The heterologous domain may be followed by a polypurine rich domain. The 3' LTR can be derived from any number of retroviruses, typically an oncoretrovirus and preferably a mammalian oncoretrovirus. In one embodiment, the 3' LTR comprises a U3-R-U5 domain. In yet another embodiment the LTR comprises a sequence as set forth in SEQ ID NO:1 or 3 from about nucleotide 9405 to about 9998 or a sequence that is at least 95%, 98% or 99.5% (rounded to the nearest $10^{th}$) identical thereto.

Figure 3:
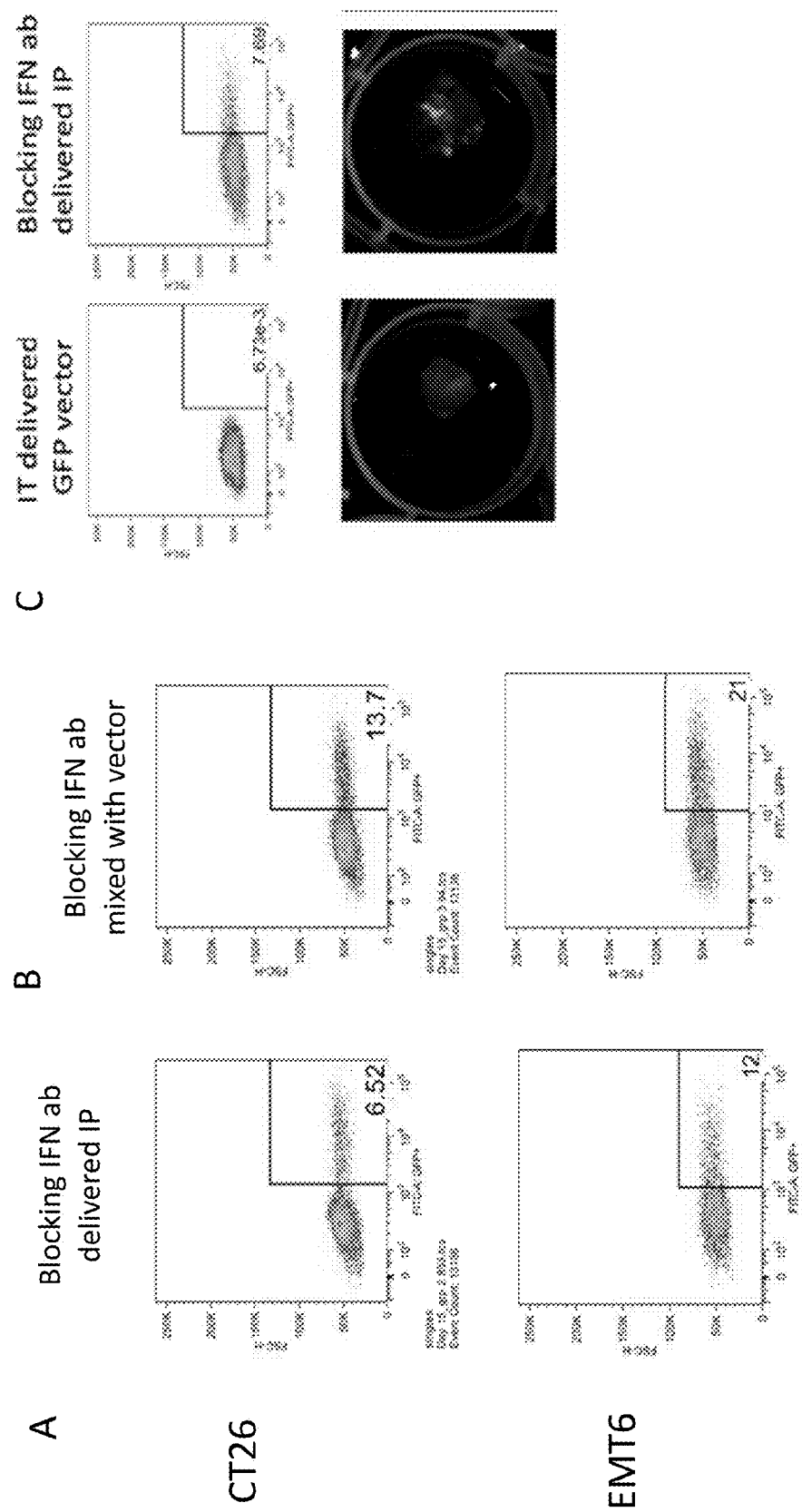
FIG. 3A-C shows improved RRV spread after delivery directly to CT26 and EMT6 subcutaneous tumors with IFN antibody administered (cf.

The disclosure also provides a recombinant retroviral vector comprising from 5' to 3' a CMV-R-U5, fusion of the immediate early promoter from human cytomegalovirus to the MLV R-U5 region; a PBS, primer binding site for reverse transcriptase; a 5' splice site; a ψ packaging signal; a gag, ORF for MLV group specific antigen; a pol, ORF for MLV polymerase polyprotein; a 3' splice site; a 4070A env, ORF for envelope protein of MLV strain 4070A; an IRES, internal ribosome entry site of encephalomyocarditis virus; a modified cytosine deaminase (thermostablized and codon optimized); a PPT, polypurine tract; and a U3-R-U5, MLV long terminal repeat. This structure is further depicted in FIG. 3.

The disclosure also provides a retroviral vector comprising a sequence as set forth in SEQ ID NO:1, 2 or 3.

The retroviral vectors can be used to treat a wide range of disease and disorders including a number of cell proliferative diseases and disorders (see, e.g., U.S. Pat. Nos. 4,405,712 and 4,650,764; Friedmann, 1989, Science, 244:1275-1281; Mulligan, 1993, Science, 260:926-932, R. Crystal, 1995, Science 270:404-410, each of which are incorporated herein by reference in their entirety, see also, The Development of Human Gene Therapy, Theodore Friedmann, Ed., Cold Spring Harbor Laboratory Press, Cold Spring Harbor, N.Y., 1999. ISBN 0-87969-528-5, which is incorporated herein by reference in its entirety).

The disclosure also provides gene therapy for the treatment of cell proliferative disorders. Such therapy would achieve its therapeutic effect by introduction of an appropriate therapeutic polynucleotide (e.g., antisense, ribozymes, suicide genes, siRNA), into cells of subject having the proliferative disorder. Delivery of polynucleotide constructs can be achieved using the recombinant retroviral vector of the disclosure, particularly if it is based on MLV, which will is capable of infecting dividing cells.

In addition, the therapeutic methods (e.g., the gene therapy or gene delivery methods) as described herein can be performed in vivo or ex vivo. It may be preferable to remove the majority of a tumor prior to gene therapy, for example, surgically or by radiation. In some aspects, the retroviral therapy may be preceded or followed by surgery, chemotherapy or radiation therapy.

Thus, the disclosure provides a recombinant retrovirus capable of infecting a non-dividing cell, a dividing cell or a neoplastic cell, therein the recombinant retrovirus comprises a viral GAG; a viral POL; a viral ENV; a heterologous nucleic acid operably linked to an IRES; and cis-acting nucleic acid sequences necessary for packaging, reverse transcription and integration. The recombinant retrovirus can be a lentivirus, such as HIV, or can be an oncovirus. As described above for the method of producing a recombinant retrovirus, the recombinant retrovirus of the disclosure may further include at least one of VPR, VIF, NEF, VPX, TAT, REV, and VPU protein. While not wanting to be bound by a particular theory, it is believed that one or more of these genes/protein products are important for increasing the viral titer of the recombinant retrovirus produced (e.g., NEF) or may be necessary for infection and packaging of virion.

The disclosure also provides a method of nucleic acid transfer to a target cell to provide expression of a particular nucleic acid (e.g., a heterologous sequence). Therefore, in another embodiment, the disclosure provides a method for introduction and expression of a heterologous nucleic acid in a target cell comprising infecting the target cell with the recombinant virus of the disclosure and expressing the heterologous nucleic acid in the target cell. As mentioned above, the target cell can be any cell type including dividing, non-dividing, neoplastic, immortalized, modified and other cell types recognized by those of skill in the art, so long as they are capable of infection by a retrovirus.

It may be desirable to modulate the expression of a gene in a cell by the introduction of a nucleic acid sequence (e.g., the heterologous nucleic acid sequence) by the method of the disclosure, wherein the nucleic acid sequence give rise, for example, to an antisense or ribozyme molecule. The term "modulate" envisions the suppression of expression of a gene when it is overexpressed, or augmentation of expression when it is under-expressed. Where a cell proliferative disorder is associated with the expression of a gene, nucleic acid sequences that interfere with the gene's expression at the translational level can be used. This approach utilizes, for example, antisense nucleic acid, ribozymes, or triplex agents to block transcription or translation of a specific mRNA, either by masking that mRNA with an antisense nucleic acid or triplex agent, or by cleaving it with a ribozyme.

It may be desirable to transfer a nucleic acid encoding a biological response modifier (e.g., a cytokine) into a cell or subject. Included in this category are immunopotentiating agents including nucleic acids encoding a number of the cytokines classified as "interleukins". These include, for example, interleukins 1 through 15, as well as other response modifiers and factors described elsewhere herein. Also included in this category, although not necessarily working according to the same mechanisms, are interferons, and in particular gamma interferon, tumor necrosis factor (TNF) and granulocyte-macrophage-colony stimulating factor (GM-CSF). Other polypeptides include, for example, angiogenic factors and anti-angiogenic factors. It may be desirable to deliver such nucleic acids to bone marrow cells or macrophages to treat enzymatic deficiencies or immune defects. Nucleic acids encoding growth factors, toxic peptides, ligands, receptors, or other physiologically important proteins can also be introduced into specific target cells.

The disclosure can be used for delivery of heterologous polynucleotides that promote drug specific targeting and effects. For example, HER2, a member of the EGF receptor family, is the target for binding of the drug trastuzumab (Herceptin™, Genentech). Trastuzumab is a mediator of antibody-dependent cellular cytotoxicity (ADCC). Activity is preferentially targeted to HER2-expressing cells with 2+ and 3+ levels of overexpression by immunohistochemistry rather than 1+ and non-expressing cells (Herceptin prescribing information, Crommelin 2002). Enhancement of expression of HER2 by introduction of vector expressing HER2 or truncated HER2 (expressing only the extracellular and transmembrane domains) in HER2 low tumors may facilitate optimal triggering of ADCC and overcome the rapidly developing resistance to HER2 that is observed in clinical use.

The substitution of yCD2 (comprising SEQ ID NO:1 from about 8877 to 9353) for the intracellular domain of HER2 allows for cell surface expression of HER2 and cytosolic localization of yCD2. The HER2 extracellular domain (ECD) and transmembrane domain (TM) (approximately 2026 bp from about position 175 to 2200 of SEQ ID NO:3) can be amplified by PCR (Yamamoto et al., Nature 319: 230-234, 1986; Chen et al., Canc. Res., 58:1965-1971, 1998) or chemically synthesized (BioBasic Inc., Markham, Ontario, Canada) and inserted between the IRES and yCD2 gene in the vector pAC3-yCD2 SEQ ID NO: 1 (e.g., between about nucleotide 8876 and 8877 of SEQ ID NO:1). Alternatively, the yCD gene can be excised and replaced with a polynucleotide encoding a HER2 polypeptide or fragment thereof. A further truncated HER2 with only the Herceptin binding domain IV of the ECD and TM domains (approximately 290 bp from position 1910 to 2200) can be amplified or chemically synthesized and used as above (Landgraf 2007; Garrett et al., J. of Immunol., 178:7120-7131, 2007). A further modification of this truncated form with the native signal peptide (approximately 69 bp from position 175-237) fused to domain IV and the TM can be chemically synthesized and used as above. The resulting viruses can be used to treat a cell proliferative disorder in a subject in combination with trastuzumab or trastuzumab and 5-FC.

Alternatively, HER2 and the modifications described above can be expressed in a separate vector containing a different ENV gene or other appropriate surface protein. This vector can be replication competent (Logg et al. J. Mol. Biol. 369:1214 2007) or non replicative "first generation" retroviral vector that encodes the envelope and the gene of interest (Emi et al. J. Virol 65:1202 1991). In the latter case the pre-existing viral infection will provide complementary gag and pol to allow infective spread of the "non-replicative" vector from any previously infected cell. Alternate ENV and glycoproteins include xenotropic and polytropic ENV and glycoproteins capable of infecting human cells, for example ENV sequences from the NZB strain of MLV and glycoproteins from MCF, VSV, GALV and other viruses (Palu 2000, Baum et al., Mol. Therapy, 13(6):1050-1063, 2006). For example, a polynucleotide can comprise a sequence wherein the GAG and POL and yCD2 genes of SEQ ID NO: 1 are deleted, the ENV corresponds to a xenotropic ENV domain of NZB MLV or VSV-g, and the IRES or a promoter such as RSV is operatively linked directly to HER2, HER2 ECDTM, HER2 ECDIVTM, or HER2 SECDIVTM.

Mixed infection of cells by VSVG pseudotyped virus and amphotropic retrovirus results in the production of progeny virions bearing the genome of one virus encapsidated by the envelope proteins of the other. The same is true for other envelopes that pseudotype retroviral particles. For example, infection by retroviruses derived as above results in production of progeny virions capable of encoding yCD2 and HER2 (or variant) in infected cells. The resulting viruses can be used to treat a cell proliferative disorder in a subject in combination with trastuzumab or trastuzumab and 5-FC.

Another aspect of the development of resistance to trastuzumab relates to the interference with intracellular signaling required for the activity of trastuzumab. Resistant cells show loss of PTEN and lower expression of p27kip1 [Fujita, Brit J. Cancer, 94:247, 2006; Lu et al., Journal of the National Cancer Institute, 93(24): 1852-1857, 2001; Kute et al., Cytometry Part A 57A:86-93, 2004). For example, a polynucleotide encoding PTEN can be recombinantly generated or chemically synthesized (BioBasic Inc., Markham, Canada) and operably inserted directly after the yCD2 polynucleotide in the vector pAC3-yCD2 or with a linker sequence as previously described, or as a replacement for yCD2. In a further example, the PTEN encoding polynucleotide can be synthesized as above and inserted between the IRES and yCD2 sequences or with a linker as previously described.

Alternatively, PTEN can be expressed in a separate vector containing a different ENV gene or other appropriate surface protein. This vector can be replication competent (Logg et al. J. Mol. Biol. 369:1214 2007) or non-replicative "first generation" retroviral vector that encodes the envelope and the gene of interest (Emi et al., J. Virol 65:1202 1991). In the latter case the pre-existing viral infection will provide complementary gag and pol to allow infective spread of the "non-replicative" vector from any previously infected cell. Alternate ENV and glycoproteins include xenotropic and polytropic ENV and glycoproteins capable of infecting human cells, for example ENV sequences from the NZB strain of MLV and glycoproteins from MCF, VSV, GALV and other viruses (Palu, Rev Med. Virol. 2000, Baum, Mol. Ther. 13(6):1050-1063, 2006). For example, a polynucleotide can comprise a sequence wherein the GAG and POL and yCD2 genes of SEQ ID NO: 1 are deleted, the ENV corresponds to a xenotropic ENV domain of NZB MLV or VSV-g, and the IRES or a promoter such as RSV is operatively linked directly to PTEN.

Mixed infection of cells by VSVG pseudotyped virus and amphotropic retrovirus results in the production of progeny virions bearing the genome of one virus encapsidated by the envelope proteins of the other [Emi 1991]. The same is true for other envelopes that pseudotype retroviral particles. For example, infection by retroviruses derived as above results in production of progeny virions capable of encoding yCD2 and PTEN (or variant) or PTEN alone in infected cells. The resulting viruses can be used to treat a cell proliferative disorder in a subject in combination with trastuzumab or trastuzumab and 5-FC.

Similarly, a polynucleotide encoding p27kip1 can be chemically synthesized (BioBasic Inc., Markham, Canada) and operably inserted directly after the yCD2 gene in the vector pAC3-yCD2 SEQ ID NO: 1 or with a linker sequence. In a further example, the p27kip1 encoding polynucleotide can be synthesized as above and inserted between the IRES and yCD2 sequences or with a linker as previously described or in place of the yCD2 gene.

Alternatively, p27kip1 can be expressed in a separate vector containing a different ENV gene or other appropriate surface protein. This vector can be replication competent (C R. Logg et al. J. Mol. Biol. 369:1214 2007) or non replicative "first generation" retroviral vector that encodes the envelope and the gene of interest (Emi et al. J. Virol 65:1202 1991). In the latter case the pre-excising viral infection will provide complementary gag and pol to allow infective spread of the "non-replicative" vector from any previously infected cell. Alternate ENV and glycoproteins include xenotropic and polytropic ENV and glycoproteins capable of infecting human cells, for example ENV sequences from the NZB strain of MLV and glycoproteins from MCF, VSV, GALV and other viruses (Palu 2000, Baum 2006, supra). For example, a polynucleotide can comprise a sequence wherein the GAG and POL and yCD2 genes of SEQ ID NO: 1 are deleted, the ENV corresponds to a xenotropic ENV domain of NZB MLV or VSV-g, and the IRES or a promoter such as RSV is operatively linked directly to p27kip1.

Mixed infection of cells by VSVG pseudotyped virus and amphotropic retrovirus results in the production of progeny virions bearing the genome of one virus encapsidated by the envelope proteins of the other [Emi 1991]. The same is true for other envelopes that pseudotype retroviral particles. For example, infection by retroviruses derived as above from both SEQ ID NO: 1 and 2 results in production of progeny virions capable of encoding yCD2 and p27kip1 (or variant) in infected cells. The resulting viruses can be used to treat a cell proliferative disorder in a subject in combination with trastuzumab or trastuzumab and 5-FC.

In another example, CD20 is the target for binding of the drug rituximab (Rituxan™, Genentech). Rituximab is a mediator of complement-dependent cytotoxicity (CDC) and ADCC. Cells with higher mean fluorescence intensity by flow cytometry show enhanced sensitivity to rituximab (van Meerten et al., Clin Cancer Res 2006; 12(13):4027-4035, 2006). Enhancement of expression of CD20 by introduction of vector expressing CD20 in CD20 low B cells may facilitate optimal triggering of ADCC.

For example, a polynucleotide encoding CD20 can be chemically synthesized (BioBasic Inc., Markham, Canada) and operably inserted directly after the yCD2 gene in the vector pAC3-yCD2(-2) SEQ ID NO: 1 or 2 with a linker sequence as previously described, or as a replacement for the yCD2 gene. In a further example, the CD20 encoding polynucleotide can be synthesized as above and inserted between the IRES and yCD2 sequences or with a linker as previously described. As a further alternative the CD20 sequence can be inserted into the pAC3-yCD2 vector after excision of the CD gene by Psi1 and Not1 digestion.

In still a further example, a polynucleotide encoding CD20 can be chemically synthesized (BioBasic Inc., Markham, Canada) and inserted into a vector containing a non amphotropic ENV gene or other appropriate surface protein (Tedder et al., PNAS, 85:208-212, 1988). Alternate ENV and glycoproteins include xenotropic and polytropic ENV and glycoproteins capable of infecting human cells, for example ENV sequences from the NZB strain of MLV and glycoproteins from MCF, VSV, GALV and other viruses [Palu 2000, Baum 2006]. For example, a polynucleotide can comprise a sequence wherein the GAG and POL and yCD2 genes of SEQ ID NO: 1 are deleted, the ENV corresponds to a xenotropic ENV domain of NZB MLV or VSV-g, and the IRES or a promoter such as RSV is operatively linked directly to CD20.

Mixed infection of cells by VSVG pseudotyped virus and amphotropic retrovirus results in the production of progeny virions bearing the genome of one virus encapsidated by the envelope proteins of the other [Emi 1991]. The same is true for other envelopes that pseudotype retroviral particles. For example, infection by retroviruses derived as above from both SEQ ID NO: 1 or 3 results in production of progeny virions capable of encoding yCD2 and CD20 in infected cells. The resulting viruses can be used to treat a cell proliferative disorder in a subject in combination with Rituxan and/or 5-FC. Similarly, infection of a tumor with a vector encoding only the CD20 marker can make the tumor treatable by the use of Rituxan.

Levels of the enzymes and cofactors involved in pyrimidine anabolism can be limiting. OPRT, thymidine kinase (TK), Uridine monophosphate kinase, and pyrimidine nucleoside phosphorylase expression is low in 5-FU resistant cancer cells compared to sensitive lines (Wang et al., Cancer Res., 64:8167-8176, 2004). Large population analyses show correlation of enzyme levels with disease outcome (Fukui et al., Int'l. J. OF Mol. Med., 22:709-716, 2008). Coexpression of CD and other pyrimidine anabolism enzymes (PAE) can be exploited to increase the activity and therefore therapeutic index of fluoropyrimidine drugs.

To further increase the genetic stability of yCD2/PAE containing vectors, the enzyme encoding gene can be chemically synthesized with random mutations throughout the sequence. These mutations can be essentially random or can consist of only mutations at the wobble position for each amino acid. The library of mutated sequences is inserted downstream or in place of the yCD2 gene as was previously described foto create a library of plasmids that can then be used to generate a library of infectious particles by transient transfection of 293T cells or equivalent. Sensitive cells can be infected with retrovirus encoding the fusion polypeptide and subjected to selection with appropriate chemicals.

DNA shuffling or "molecular breeding" allows genetic information to be shuffled, leading to recombinants with desired properties. Different proteins and enzymes have been improved using DNA shuffling (Stemmer 1994 Proc Natl Acad Sci USA 91(22): 10747-51; Stemmer 1994 Nature 370 (6488):389-91). Genetic recombination is a major force driving the evolution of many viruses. In retrovirus, recombination between two co-packaged retroviral genomes may occur at rates as high as 40% per replication cycle. High rates of recombination at each replication cycle enables genetic information to be shuffled rapidly, leading to recombinants with new pattern of mutations and phenotypes within a short period of time. For example, molecular breeding of retrovirus containing a library of recombinant ecotropic envelope sequences from six murine leukemia virus resulted in a viral clone with a new tropism. Using the same method, several viral clones were selected with improved stability and processing yields (Soong et al., 2000 Nat Genet. 25(4):436-9; Powell et al., 2000 Nat Biotechnol 18(12):1279-82).

Polynucleotide sequence incorporated into the vectors of the disclosure are sometimes unstable resulting in deletion of the polynucleotide sequence from the viral genome over time. The basis for this is not well understood, but it is likely sequence dependent Molecular breeding using the disclosure to select for recombinant viral clones that have acquired optimal recombinations within the heterologous polynucleotide sequence is employed to select for viral clones that have greater vector stability.

For example, the HSV-TK coding sequence is not as stable as desired in some situations Molecular breeding of recombinant retroviral vectors encompass a pool of degenerated coding sequence of HSV-TK is performed to select recombinant vectors that have great vector stability. Randomly mutagenized Herpes Thymidine Kinase (TK) is chemically synthesized (Bio Basic Inc, Markham, Canada). The synthetic sequence is inserted 3' of the yCD2 sequence in SEQ ID NO:1, or by itself in the pAC3-yCD2 vector back bones after excision of the CD2 gene. The retroviral vector mixture is packaged as previously described. Mouse fibroblast LMTK-cells or humans 143Tk– are infected with vector and selected for TK activity in HAT media (Hiller et al., Mol. Cell. Biol. 8(8):3298-3302, 1988). Serial passage of supernatants of resistant cells to fresh LMTK–/143Tk– cells again selected in HAT media results in selection of stable vectors expressing TK. TK+ resistant cells can be isolated and TK sequences rescued by standard PCR based techniques for mutation analysis (Cowell et al., cDNA Library Protocols, Published by Humana Press, 1996). In this manner, sequences are selected for both expression of functional protein and genomic stability of retroviral vector construct. Similar strategies can be employed for UPRT, OPRT (Olah et al., Cancer Res. 40:2869-2875, 1980; and Suttle, Somatic Cell & Mol. Genet., 15(5):435-443, 1989) and other genes of interest. In addition the serial passage strategy can be used for non-selectable genes and the genomic DNA after serial passage screened for full length inserts by PCR across the IRES-insert gene (see FIG. 5). The full length inserts can be purified and cloned out back into the viral vector then retested. Several cycles of this procedure can be performed to select the most stable gene. This strategy can also be used for passage in animals with or without tumors, and even in patient tissue.

Alternatively, OPRT, UPRT, TK or other PAE can be expressed in a separate vector containing a different ENV gene or other appropriate surface glycoprotein. This vector can be replication competent (Logg et al. J. Mol. Biol.

369:1214 2007) or non-replicative "first generation" retroviral vector that encodes the envelope and the gene of interest (Emi et al. J. Virol 65:1202 1991). In the latter case the pre-existing viral infection will provide complementary gag and pol to allow infective spread of the "non-replicative" vector from any previously infected cell. Alternate ENV and glycoproteins include xenotropic and polytropic ENV and glycoproteins capable of infecting human cells, for example ENV sequences from the NZB strain of MLV and glycoproteins from MCF, VSV, GALV and other viruses [Palu 2000, Baum 2006, supra]. For example, a polynucleotide can comprise a sequence wherein the GAG and POL genes are deleted, the ENV corresponds to a xenotropic ENV domain from NZB MLV or VSV-g, and the IRES or a promoter such as RSV is operatively linked directly to OPRT, UPRT, TK, or other PAE gene.

Mixed infection of cells by VSV-g pseudotyped virus and amphotropic retrovirus results in the production of progeny virions bearing the genome of one virus encapsidated by the envelope proteins of the other (Emi et al., J. Virol. 65:1202, 1991). The same is true for other envelopes that pseudotype retroviral particles. For example, infection by retroviruses derived as above from both SEQ ID NO: 1 and 3 results in production of progeny virions capable of encoding yCD2 and OPRT in infected cells. The resulting viruses can be used to treat a cell proliferative disorder in a subject in combination with 5-FC.

The recombinant retrovirus of the disclosure can be used for the treatment of a neuronal disorder for example, may optionally contain an exogenous gene, for example, a gene which encodes a receptor or a gene which encodes a ligand. Such receptors include receptors which respond to dopamine, GABA, adrenaline, noradrenaline, serotonin, glutamate, acetylcholine and other neuropeptides, as described above. Examples of ligands which may provide a therapeutic effect in a neuronal disorder include dopamine, adrenaline, noradrenaline, acetylcholine, gamma-aminobutyric acid and serotonin. The diffusion and uptake of a required ligand after secretion by an infected donor cell would be beneficial in a disorder where the subject's neural cell is defective in the production of such a gene product. A cell genetically modified to secrete a neurotrophic factor, such as nerve growth factor, (NGF), might be used to prevent degeneration of cholinergic neurons that might otherwise die without treatment.

Alternatively, cells be grafted into a subject with a disorder of the basal ganglia, such as Parkinson's disease, can be modified to contain an exogenous gene encoding L-DOPA, the precursor to dopamine. Parkinson's disease is characterized by a loss of dopamine neurons in the substantia-nigra of the midbrain, which have the basal ganglia as their major target organ.

Other neuronal disorders that can be treated similarly by the method of the disclosure include Alzheimer's disease, Huntington's disease, neuronal damage due to stroke, and damage in the spinal cord. Alzheimer's disease is characterized by degeneration of the cholinergic neurons of the basal forebrain. The neurotransmitter for these neurons is acetylcholine, which is necessary for their survival. Engraftment of cholinergic cells infected with a recombinant retrovirus of the disclosure containing an exogenous gene for a factor which would promote survival of these neurons can be accomplished by the method of the disclosure, as described. Following a stroke, there is selective loss of cells in the CA1 of the hippocampus as well as cortical cell loss which may underlie cognitive function and memory loss in these patients. Once identified, molecules responsible for CA1 cell death can be inhibited by the methods of this disclosure. For example, antisense sequences, or a gene encoding an antagonist can be transferred to a neuronal cell and implanted into the hippocampal region of the brain.

For diseases due to deficiency of a protein product, gene transfer could introduce a normal gene into the affected tissues for replacement therapy, as well as to create animal models for the disease using antisense mutations. For example, it may be desirable to insert a Factor IX encoding nucleic acid into a retrovirus for infection of a muscle or liver cell.

The disclosure also provides gene therapy for the treatment of cell proliferative or immunologic disorders. Such therapy would achieve its therapeutic effect by introduction of an antisense or dominant negative encoding polynucleotide into cells having the proliferative disorder, wherein the polynucleotide binds to and prevents translation or expression of a gene associated with a cell-proliferative disorder. Delivery of heterologous nucleic acids useful in treating or modulating a cell proliferative disorder (e.g., antisense polynucleotides) can be achieved using a recombinant retroviral vector of the disclosure. In another embodiment, a cell proliferative disorder is treated by introducing a CD polynucleotide of the disclosure, expressing the polynucleotide to produce a polypeptide comprising cytosine deaminase activity and contacting the cell with 5-fluorocytosine in an amount and for a period of time to produce a cytotoxic amount of 5-FU.

A number of chemotherapeutic agents are currently on the market having varying degrees of success from full remission to temporary remission and prolonged life with expected recurrence. Some of the cancer therapeutic agents on the market target the vascular angiogenic properties of tumor. The composition target the angiogenesis of tumors seeking to reduces blood supply and nutrients to the tumor or cancer and thereby reduce the tumor and prolong a subject's life. VEGF is an angiogenic factor known to play a role in tumor growth. Thus, antagonists of VEGF have been developed as anti-cancer agents.

Human VEGF mediates neoangiogenesis in normal and malignant vasculature; it is overexpressed in most malignancies and high levels have correlated with a greater risk of metastases and poor prognosis in many. When VEGF interacts with its receptor in in vitro models of angiogenesis, endothelial cell proliferation and new blood vessel formation occur. In animal models, VEGF has been demonstrated to induce vascular endothelial-cell proliferation/migration, sustain survival of newly-formed blood vessels, and enhance vascular permeability.

A VEGF antagonist agent is one that targets or negatively regulates the VEGF signaling pathway. Examples include VEGF inhibitors (e.g., agents that directly inhibit VEGF (e.g., VEGF-A, -B, -C, or -D), such as by binding VEGF (e.g., anti-VEGF antibodies such as bevacizumab (AVASTIN®) or ranibizumab (LUCENTIS®), or other inhibitors such as pegaptanib, NEOVASTAT®, AE-941, VEGF Trap, and PI-88)), modulators of VEGF expression (e.g., INGN-241, oral tetrathiomolybdate, 2-methoxyestradiol, 2-methoxyestradiol nanocrystal dispersion, bevasiranib sodium, PTC-299, Veglin), inhibitors of a VEGF receptor (e.g., KDR or VEGF receptor III (Flt4), for example anti-KDR antibodies, VEGFR2 antibodies such as CDP-791, IMC-1121B, VEGFR2 blockers such as CT-322), modulators of VEGFR expression (e.g., VEGFR1 expression modulator Sirna-027) or inhibitors of VEGF receptor downstream signaling. In some aspects described herein, the VEGF antagonist agent is bevacizumab, pegaptanib, ranibizumab, sorafenib, sunitinib, AE-941, VEGF Trap, pazopanib, vandetanib, vatalanib, cediranib, fenretinide, squalamine, INGN-241, oral tetrathiomolybdate, tetrathiomolybdate, Panzem NCD, 2-methoxyestradiol, AEE-788, AG-013958, bevasiranib sodium, AMG-706, axitinib, BIBF-1120, CDP-791, CP-547632, PI-88, SU-14813, SU-6668, XL-647, XL-999, IMC-1121B, ABT-869, BAY-57-9352, BAY-73-4506, BMS-582664, CEP-7055, CHIR-265, CT-322, CX-3542, E-7080, ENMD-1198, OSI-930, PTC-299, Sirna-027, TKI-258, Veglin, XL-184, or ZK-304709.

Bevacizumab (AVASTIN®) (rhuMAb-VEGF)(Anti-VEGF monoclonal antibody) is a recombinant human/murine chimeric monoclonal antibody directed against vascular endothelial growth factor (VEGF)). It is prepared by engineering VEGF-binding residues of a murine anti-VEGF monoclonal antibody into framework regions of human immunoglobulin-1 (IgG1) (Prod Info Avastin, 2004). Only 7% of the amino acid sequence is derived from the murine antibody, with 93% from IgG1. Bevacizumab binds and neutralizes all human VEGF forms via recognition of binding sites for the two human VEGF receptor types (flt-1 and flk-1). In animal models, the antibody has been shown to stabilize established tumors or suppress tumor growth by inhibiting angiogenesis induced by VEGF.

The pharmacokinetics of bevacizumab are linear after doses of 0.3 mg/kg or greater (Anon, 2002). Following 90-minute intravenous infusions of 0.3, 1, 3, and 10 mg/kg in advanced cancer patients (n=25), peak serum concentrations of bevacizumab ranged from 5 to 9 mcg/mL, 21 to 39 mcg/mL, 52 to 92 mcg/mL, and 186 to 294 mcg/mL, respectively; slight accumulation was observed with repeat doses (weekly), but this was not significant and pharmacokinetics remained linear. Steady-state levels of bevacizumab were obtained in 100 days after 1 to 20 mg/kg weekly, every 2 weeks, or every 3 week.

The recommended dose of bevacizumab is 5 milligrams/kilogram infused intravenously over 30 minutes every 2 weeks until disease progression diminishes. Bevacizumab should follow chemotherapy. Efficacy of single-agent bevacizumab has not been established. Bevacizumab (which may be coadministered with the gemcitabine and docetaxel, or within a week before or after chemotherapy), is administered intravenously, at about 1 mg/kg to about 15 mg/kg, preferably about 5 mg/kg.

The methods and compositions of the disclosure are useful in combination therapies including therapies with bevacizumab. As described herein a replication competent retrovirus (RCR) of the disclosure comprising a therapeutic (e.g., a cytotoxic gene) is useful in treating cell proliferative disorders. An advantage of the RCR of the disclosure includes its ability to infect replicating cells cancer cells. Where the transgene of the vector comprises a cytotoxic gene (e.g., a gene that encodes a polypeptide that converts a non-cytotoxic agent to a cytotoxic agent) provides the ability to kill cancer cells.

The disclosure provides methods for treating cell proliferative disorders such as cancer and neoplasms comprising administering an RCR vector of the disclosure followed by treatment with a chemotherapeutic agent or anti-cancer agent. In one aspect, the RCR vector is administered to a subject for a period of time prior to administration of the chemotherapeutic or anti-cancer agent that allows the RCR to infect and replicate. The subject is then treated with a chemotherapeutic agent or anti-cancer agent for a period of time and dosage to reduce proliferation or kill the cancer cells. In one aspect, if the treatment with the chemotherapeutic or anti-cancer agent reduces, but does not kill the cancer/tumor (e.g., partial remission or temporary remission), the subject may then be treated with a non-toxic therapeutic agent (e.g., 5-FC) that is converted to a toxic therapeutic agent in cells expression a cytotoxic gene (e.g., cytosine deaminase) from the RCR. Using such methods the RCXR vectors of the disclosure are spread during a replication process of the tumor cells, such cells can then be killed by treatment with an anti-cancer or chemotherapeutic agent and further killing can occur using the RCR treatment process described herein.

In yet another embodiment of the disclosure, the heterologous gene can comprise a coding sequence for a target antigen (e.g., a cancer antigen). In this embodiment, cells comprising a cell proliferative disorder are infected with an RCR comprising a heterologous polynucleotide encoding the target antigen to provide expression of the target antigen (e.g., overexpression of a cancer antigen). An anticancer agent comprising a targeting cognate moiety that specifically interacts with the target antigen is then administered to the subject. The targeting cognate moiety can be operably linked to a cytotoxic agent or can itself be an anticancer agent. Thus, a cancer cell infected by the RRV comprising the targeting antigen coding sequences increases the expression of target on the cancer cell resulting in increased efficiency/efficacy of cytotoxic targeting.

Blocking of interactions between cells of the immune system have been shown to have significant immunological effects, either activating or suppressing (Waldmann Annu Rev Med. 57:65 2006). For example, blockade of the interaction of CTLA-4 (CD 152) and B7.1 (CD80) which modulates the activation of T cells has been shown to cause immune stimulation, presumably by blocking this suppressive interaction (Peggs et al. Curr. Opin. Immunol. 18:206, 2006). This blockade can potentially be achieved either by antibodies against CTLA-4 or by soluble B7.1. Systemic administration of these types of molecules can have undesirable global effects which can at a minimum lead to deleterious side-effects or even death in the case of one C28 agonist (Suntharalingam et al. NEJM 355 1018 2006). Pfizer has been developing one such anti-CTLA-4 blockading antibody (CP-675,206) as an anticancer reagent but has recently stopped development because of significant side effects. Local delivery of blockading molecules that are released into the local environment, from the tumor after infection with a replication competent vector encoding such molecules that are released into the extracellular space, provides the immune modulation locally and avoid these serious side effects. The blockading molecules are antibodies, single chain antibodies, soluble versions of the natural ligand or other peptides that bind such receptors.

In yet another embodiment, an RCR of the disclosure can comprise a coding sequence comprising a binding domain (e.g., an antibody, antibody fragment, antibody domain or receptor ligand) that specifically interacts with a cognate antigen or ligand. The RCR comprising the coding sequence for the binding domain can then be used to infect cells in a subject comprising a cell proliferative disorder such as a cancer cell or neoplastic cell. The infected cell will then express the binding domain or antibody. An antigen or cognate operably linked to a cytotoxic agent or which is cytotoxic itself can then be administered to a subject. The cytotoxic cognate will then selectively kill infected cells expressing the binding domain. Alternatively the binding domain itself can be an anti-cancer agent.

As used herein, the term "antibody" refers to a protein that includes at least one immunoglobulin variable domain or immunoglobulin variable domain sequence. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody" encompasses antigen-binding fragments of antibodies (e.g., single chain antibodies, Fab fragments, F(ab').sub.2, a Fd fragment, a Fv fragments, and dAb fragments) as well as complete antibodies.

The VH and VL regions can be further subdivided into regions of hypervariability, termed "complementarity determining regions" (CDR), interspersed with regions that are more conserved, termed "framework regions" (FR). The extent of the framework region and CDRs has been precisely defined (see, Kabat, E. A., et al. Sequences of Proteins of Immunological Interest, Fifth Edition, U.S. Department of Health and Human Services, NIH Publication No. 91-3242, and Chothia, C. et al. (1987) J. Mol. Biol. 196:901-917). Kabat definitions are used herein. Each VH and VL is typically composed of three CDRs and four FRs, arranged from amino-terminus to carboxy-terminus in the following order: FR1, CDR1, FR2, CDR2, FR3, CDR3, FR4.

An "immunoglobulin domain" refers to a domain from the variable or constant domain of immunoglobulin molecules. Immunoglobulin domains typically contain two .beta.-sheets formed of about seven .beta.-strands, and a conserved disulphide bond (see, e.g., A. F. Williams and A. N. Barclay 1988 Ann. Rev Immunol. 6:381-405). The canonical structures of hypervariable loops of an immunoglobulin variable can be inferred from its sequence, as described in Chothia et al. (1992) J. Mol. Biol. 227:799-817; Tomlinson et al. (1992) J. Mol. Biol. 227:776-798); and Tomlinson et al. (1995) EMBO J. 14(18):4628-38.

As used herein, an "immunoglobulin variable domain sequence" refers to an amino acid sequence which can form the structure of an immunoglobulin variable domain. For example, the sequence may include all or part of the amino acid sequence of a naturally-occurring variable domain. For example, the sequence may omit one, two or more N- or C-terminal amino acids, internal amino acids, may include one or more insertions or additional terminal amino acids, or may include other alterations. In one embodiment, a polypeptide that includes immunoglobulin variable domain sequence can associate with another immunoglobulin variable domain sequence to form a target binding structure (or "antigen binding site"), e.g., a structure that interacts with Tie1, e.g., binds to or inhibits Tie1.

The VH or VL chain of the antibody can further include all or part of a heavy or light chain constant region, to thereby form a heavy or light immunoglobulin chain, respectively. In one embodiment, the antibody is a tetramer of two heavy immunoglobulin chains and two light immunoglobulin chains, wherein the heavy and light immunoglobulin chains are inter-connected by, e.g., disulfide bonds. The heavy chain constant region includes three domains, CH1, CH2 and CH3. The light chain constant region includes a CL domain. The variable region of the heavy and light chains contains a binding domain that interacts with an antigen. The constant regions of the antibodies typically mediate the binding of the antibody to host tissues or factors, including various cells of the immune system (e.g., effector cells) and the first component (Clq) of the classical complement system. The term "antibody" includes intact immunoglobulins of types IgA, IgG, IgE, IgD, IgM (as well as subtypes thereof). The light chains of the immunoglobulin may be of types kappa or lambda. In one embodiment, the antibody is glycosylated. An antibody can be functional for antibody-dependent cytotoxicity and/or complement-mediated cytotoxicity.

The term "monospecific antibody" refers to an antibody that displays a single binding specificity and affinity for a particular target, e.g., epitope. This term includes a "monoclonal antibody" which refers to an antibody that is produced as a single molecular species, e.g., from a population of homogenous isolated cells. A "monoclonal antibody composition" refers to a preparation of antibodies or fragments thereof of in a composition that includes a single molecular species of antibody. In one embodiment, a monoclonal antibody is produced by a mammalian cell. One or more monoclonal antibody species may be combined.

One or more regions of an antibody can be human or effectively human. For example, one or more of the variable regions can be human or effectively human. For example, one or more of the CDRs can be human, e.g., HC CDR1, HC CDR2, HC CDR3, LC CDR1, LC CDR2, and LC CDR3. Each of the light chain CDRs can be human. HC CDR3 can be human. One or more of the framework regions can be human, e.g., FR1, FR2, FR3, and FR4 of the HC or LC. In one embodiment, all the framework regions are human, e.g., derived from a human somatic cell, e.g., a hematopoietic cell that produces immunoglobulins or a non-hematopoietic cell. In one embodiment, the human sequences are germline sequences, e.g., encoded by a germline nucleic acid. One or more of the constant regions can be human or effectively human. In another embodiment, at least 70, 75, 80, 85, 90, 92, 95, or 98% of the framework regions (e.g., FR1, FR2, and FR3, collectively, or FR1, FR2, FR3, and FR4, collectively) or the entire antibody can be human or effectively human. For example, FR1, FR2, and FR3 collectively can be at least 70, 75, 80, 85, 90, 92, 95, 98, or 99% identical to a human sequence encoded by a human germline V segment of a locus encoding a light or heavy chain sequence.

All or part of an antibody can be encoded by an immunoglobulin gene or a segment thereof. Exemplary human immunoglobulin genes include the kappa, lambda, alpha (IgA1 and Iga2), gamma (IgG1, IgG2, IgG3, IgG4), delta, epsilon and mu constant region genes, as well as the myriad immunoglobulin variable region genes. Full-length immunoglobulin light chains (about 25 Kd or 214 amino acids) are encoded by a variable region gene at the NH2-terminus (about 110 amino acids) and a kappa or lambda constant region gene at the COOH— terminus. Full-length immunoglobulin heavy chains (about 50 Kd or 446 amino acids), are similarly encoded by a variable region gene (about 116 amino acids) and one of the other aforementioned constant region genes, e.g., gamma (encoding about 330 amino acids). A light chain refers to any polypeptide that includes a light chain variable domain. A heavy chain refers to any polypeptide that a heavy chain variable domain.

The term "antigen-binding fragment" of a full-length antibody (or simply "antibody portion," or "fragment"), as used herein, refers to one or more fragments of a full-length antibody that retain the ability to specifically bind to a target of interest. Examples of binding fragments encompassed within the term "antigen-binding fragment" of a full length antibody include (i) a Fab fragment, a monovalent fragment consisting of the VL, VH, CL and CH1 domains; (ii) a F(ab').sub.2 fragment, a bivalent fragment including two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR) that retains functionality. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules known as single chain Fv (scFv). See e.g., Bird et al. (1988) Science 242:423-426; and Huston et al. (1988) Proc. Natl. Acad. Sci. USA 85:5879-5883.

Antibody fragments can be obtained using any appropriate technique including conventional techniques known to those with skill in the art. The term "monospecific antibody" refers to an antibody that displays a single binding specificity and affinity for a particular target, e.g., epitope. This term includes a "monoclonal antibody" or "monoclonal antibody composition," which as used herein refer to a preparation of antibodies or fragments thereof of single molecular composition. As used herein, "isotype" refers to the antibody class (e.g., IgM or IgG1) that is encoded by heavy chain constant region genes.

The disclosure provides a method of treating a subject having a cell proliferative disorder. The subject can be any mammal, and is preferably a human. The subject is contacted with a recombinant replication competent retroviral vector of the disclosure. The contacting can be in vivo or ex vivo. Methods of administering the retroviral vector of the disclosure are known in the art and include, for example, systemic administration, topical administration, intraperitoneal administration, intra-muscular administration, intracranial, cerebrospinal, as well as administration directly at the site of a tumor or cell-proliferative disorder. Other routes of administration known in the art.

For example, the disclosure provides methods for treating cell proliferative disorders such as cancer and neoplasms comprising administering an RRV of the disclosure followed by treatment with a chemotherapeutic agent or anti-cancer agent. In one aspect, the RRV is administered to a subject for a period of time prior to administration of the chemotherapeutic or anti-cancer agent that allows the RRV to infect and replicate. The vector may be administered locally (e.g., at the site of the tumor) or may be systemically administered (e.g., intravenously into the circulation). Advantageously the vector is capable of crossing the blood brain barrier and transduces/infects tumor cells of the brain. Doses of the vector may be given daily by single dose or multiple doses and may be give periodically during the treatment (e.g., every day for several days, every other day for several days and the like). The data demonstrate that the doses IV may be given once with sufficient transduction/infection in brain cancer cells. Typically the dose will be about $9 \times 10^6$ TU/100 µl; however, the dose may range from about $10^5$ to about $10^{12}$ TU given in one or more doses of 100 µl or scaled appropriately by blood value for larger animals and humans (roughly 2500 fold for a human compared to a mouse).

Any number of the foregoing embodiments (e.g., vector constructs, heterologous genes etc.) can be used in combination with steroid, steroid antagonists, radiation, anti-IFN, IFN, and the like. As demonstrated herein, various combination therapies comprising (i) radiation treatment following viral therapy with a vector expressing a cytosine deaminase and under going 5-FC therapy can be used, (ii) anti-IFN or other therapies to reduce innate antiviral activity can be used in combination with any of the foregoing vectors, (iii) steroids can be used in combination with any of the vectors of the disclosure to promote viral infection and spread (iv) anti-progestins such as mifepristone can be used in combination with any of the vectors of the disclosure to promote viral infection and spread. These and other embodiments are further described elsewhere herein. One of skill in the art can monitor the therapeutic activity of a polypeptide having cytosine deaminase activity in any of the foregoing combination therapies or in any of the vectors described above comprising a polynucleotide that expresses a polypeptide having cytosine deaminase activity; the method comprising measuring FBAL in a sample from the subject.

Thus, the disclosure includes various pharmaceutical compositions useful for treating a cell proliferative disorder. The pharmaceutical compositions according to the disclosure are prepared by bringing a retroviral vector containing a heterologous polynucleotide sequence useful in treating or modulating a cell proliferative disorder according to the disclosure into a form suitable for administration to a subject using carriers, excipients and additives or auxiliaries. In some embodiments, the retroviral vector is formulated in combination with a PPR or IFN pathway inhibitor. Frequently used carriers or auxiliaries include magnesium carbonate, titanium dioxide, lactose, mannitol and other sugars, talc, milk protein, gelatin, starch, vitamins, cellulose and its derivatives, animal and vegetable oils, polyethylene glycols and solvents, such as sterile water, alcohols, glycerol and polyhydric alcohols. Intravenous vehicles include fluid and nutrient replenishers. Preservatives include antimicrobial, anti-oxidants, chelating agents and inert gases. Other pharmaceutically acceptable carriers include aqueous solutions, non-toxic excipients, including salts, preservatives, buffers and the like, as described, for instance, in Remington's Pharmaceutical Sciences, 15th ed. Easton: Mack Publishing Co., 1405-1412, 1461-1487 (1975) and The National Formulary XIV., 14th ed. Washington: American Pharmaceutical Association (1975), the contents of which are hereby incorporated by reference. The pH and exact concentration of the various components of the pharmaceutical composition are adjusted according to routine skills in the art. See Goodman and Gilman's The Pharmacological Basis for Therapeutics (7th ed.).

The pharmaceutical compositions may further comprise one or more additional therapeutic agents such as a steroid, an anti-IFN or other inhibitor of innate viral immunity.

The following Examples are intended to illustrate, but not to limit the disclosure. While such Examples are typical of those that might be used, other procedures known to those skilled in the art may alternatively be utilized.

EXAMPLES

Example 1: Replication Competent Recombinant Retroviral Vectors Spread Efficiently in Intracranial Tumors but Spread Poorly in Subcutaneous Tumors with the Same Origin The replication competent recombinant retroviral vector Toca 511 (aka T5.0002, see, e.g., WO 2010/036986 and WO 2010/045002, both incorporated herein by reference) is an amphotropic MLV vector that encodes a modified yeast cytosine deaminase (CD) gene under the control of the EMCV IRES. This vector efficiently spread and delivered the therapeutic CD gene when injected into intracranial tumors in rodents. The tumor can then be ablated by administration of 5-FC wick is converted locally by CD to 5-FU.

Vector preparations and assay for strength (transforming units/ml—TU/ml) and potency have been described previously (see, e.g., International application publications WO2010036986 and WO2010148203, incorporated herein by reference). Briefly, the vector can be prepared by transient transfection for initial trials, but is preferably made from a permanent producer cell line such as one derived from the human fibrosarcoma HT1080 (ATCC CCL-121) with subsequent downstream processing to give formulated preparations with an approximate titer of $10^8$ TU/ml.

Titers of vector preparations were determined using several dilutions of vector preparation on PC-3 cells (ATCC CRL-1435) as target for infection, adding AZT 24 h after infection to stop vector replication and counting the number of integrated proviruses in the target cell population by qPCR. PC-3 cells were seeded on 12-well plates on Day 0, (12-18 hours prior to transduction) in one mL complete DMEM medium at a cell confluence targeting 60% on the day of transduction. On day 1, the PC-3 cells were transduced (triplicate transduction for each sample and dilution) with 20 μl of the diluted vector preparations (1:20 and 1:200) prepared in complete DMEM medium in the presence of 4 μg/ml polybrene. Plates were returned to the incubator for 24 hours and on Day 2, AZT was added to 40 μM from a 10 mM stock solution to arrest viral replication. Cells were harvested on day 3, and the genomic DNA was prepared from each well of cells using a Promega Maxwell 16 automated purification instrument with the associated cartridges. The concentration of DNA was determined using a Nanodrop ND-1000 (Wilmington, Del.). The integrity of the DNA was checked by gel electrophoresis on a 0.8% ethidium bromide agarose gel (Invitrogen e-gel, Carlsbad, Calif.). QPCR was carried out in triplicate using the following primers and probe (Integrated DNA Technologies, Coralville, Iowa): Forward primer in the MLV-U3-B region; Reverse primer in the MLV-Psi region and a FAM-labeled probe, and the qPCR reactions carried out on a Bio-Rad CFX96 Real Time System (Hercules, Calif.). The amplicon size is 192 bp. These primers and detection probe will detect the integrated provirus with the 3'UTR transposed to the 5' end of the provirus, and will not detect contaminating plasmid DNA used in the transient transfection step to make the infectious virus. The proviral copy number was determined using a 7 serial log dilution standard curve from a proviral containing plasmid pAZ3-GFP (aka T5.0006). DNA from cells infected with a control vector was included as a positive control for transfection and qPCR quantitation; controls without template were run to determine contamination or background.

In a first experiment, B6C3F1 mice were implanted with Tu-2449 tumors (Weissenberger et al., 1997), Toca 511 was administered at $10^5$ TU/g and 5-FC dosing IP or OG (oral gavage) was initiated 20 days after Tu-2449 implantation for 2 days BID at either 500 or 250 mg/kg per day, and then again 1 hour before tumor harvesting and processing on the third day. Brain tumors were excised and lysates (2-4/group) were analyzed by HPLC. In vivo conversion of 5-FC to 5-FU was detected in all groups dosed with Toca 511 and 5-FC (FIGS. 1A and C). The Toca 511/no 5-FC group had neither 5-FC nor 5-FU detectable signals as expected (FIG. 1A). The 5-FC only group had detectable 5-FC signals but no signal for 5-FU. Mice given Toca 511 and 5-FC (IP or OG) had comparable levels of 5-FU and very low levels of 5-FC. In all Toca 511 plus 5-FC groups detection of 5-FC was near background levels while 5-FU was readily detectable suggesting the optimized CD gene is rapidly converting almost all of the available 5-FC to 5-FU in the tumor. Isolated Tu-2449 tumors were also processed for western blot analysis of CD expression (FIGS. 1B and C). All groups treated with Toca 511 had readily observable CD expression while mice that were not given Toca 511 did not have detectable CD protein. When available, the remaining pellets, after supernatants were removed for HPLC analysis, were extracted for genomic DNA. Extracted samples were analyzed by qPCR for proviral integration using MLV-LTR primers and probe. The no vector group DNA was negative for proviral sequences as expected, and in the other groups the copy number/genome ranged from 1.4 copies/genome (208,668 copies/microgram) to 15 copies/genome (2,183,971 copies/microgram), with an average of 2.8 and a median of 3.7 copies/genome (FIG. 1C). Parallel analyses using the envelope (ENV) and CD gene primers and probes gave similar results.

Figure 2:
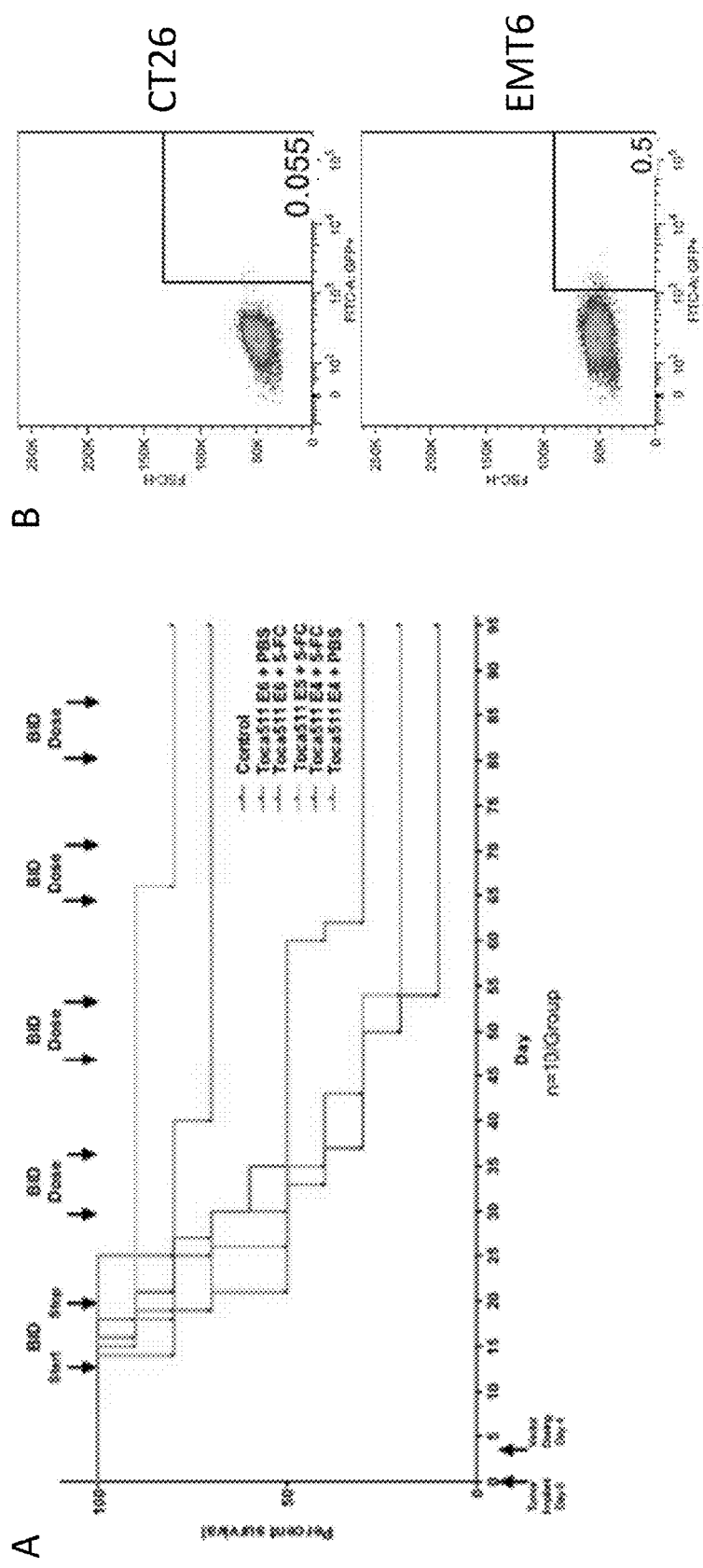
FIG. 2A-B shows: A. Kaplan-Meir survival curve of an intracranial CT26 tumor model (colon tumor metastases) with various doses of Toca 511 and 5-FC or PBS control; B. Minimal Replicative Murine Leukemia Virus (RRV)) spread in subcutaneous tumor models CT 26 (colon cancer) and EMT6 (breast cancer) with vector alone, as measured by GFP-mediated FACS sorting of excised tumors. The number at the bottom right in the FACS diagram is the percent GFP positive cells.

In FIG. 2A, intracranially cannulated BALB/c mice were implanted with $1\times10^4$ CT26 cells and various doses of Toca 511 or vehicle were injected into the tumor through the same cannula 4 days after cell injection. After allowing 9 days for vector spread, cycles of prodrug 5-FC 500 mg/kg or PBS BID dosing were initiated. Each cycle consisted of 10 days no dosing after 4 days of dosing for each cycle. Cycles were repeated until termination of the study. Efficient and productive spread of Toca 511 in the brain was measured by prolonged survival in the Toca 511 treated groups compared to the control. The mid (E5) and high (E6) dose levels in combination with 5-FC resulted in prolonged survival compared to the vector plus PBS control (p<0.0012 and <0.0113 respectively, FIG. 2A).

Intratumoral (it) delivery of replicative recombinant retroviral vectors to subcutaneous tumors was investigated as follows. BALB/c mice were injected with $5\times10^4$ CT26 or EMT6 on the right flank of BALB/c mice and were allowed to grow until they reached 50-175 $mm^3$ in size. When tumors were within the range of 50-175 $mm^3$, they were directly injected with approximately $1\times10^7$ TU of replication competent retroviral vector carrying the GFP gene. After 12 days, tumors were removed and processed for cytometric analysis to measure transduced GFP expressing cells (FIG. 2B). These data showed that, unexpectedly, there was almost no spread of the vector in the subcutaneous tumors, despite the fact that the virus does spread in intracranial tumors and in tissue culture (see example 6).

Example 2: Efficient Spread of Replication Competent Retroviral Vector in Subcutaneous Tumors after Treatment with Type I Interferon Blocking Antibody BALB/c mice were injected with $5\times10^4$ CT26 or EMT6 on the right flank of BALB/c mice and were allowed to grow until they reached 50-175 $mm^3$ in size. When tumors were within the range of 50-175 $mm^3$, they were directly injected with approximately $1\times10^7$ TU of replication competent retroviral vector carrying the GFP gene. Type I interferon blocking antibody (BioLegend, #127304; clone MAR1-5A3) was delivered either IP or mixed with the replication competent retroviral vector at time of intratumor injection. IP injected mice had three injections given over 3 days (2.5 mg/mouse/day). 20 mg of interferon blocking antibody was used when mixed with vector before injection into the tumor. 12 days after vector delivery, tumors were processed for analysis by cytometry to measure the number of transduced GFP+ tumor cells. Mice that were given type I blocking interferon antibody either by IP injection or mixed with vector at time of intratumoral delivery had markedly improved vector spread 12 days post-vector injection in CT26 and EMT6 tumors (FIG. 3A). Visualization of post-9 day MLV-GFP vector injected EMT6 tumors along with IP delivered blocking interferon antibody showed much higher percentage of GFP+ positive tumor cells compared to intra-tumoral injection of vector only (FIG. 3B). These results show that inhibition of Interferon only around the time of initial infection, is sufficient to overcome the inefficiency of infection of the subcutaneous tumors. The IP injected mice received anti-IFN for the first 3 days and the mice receiving a mixture of anti-IFN and vector received the anti-IFN only at the time of initial administration. Therefore infection of otherwise resistant tumors by replicative MLV vectors is enabled by a single administration at the time of infection of an anti-IFN agent. This is also a surprising result as the virus clearly has to spread after the initial infection. This result shows that the initial infection event is the biggest hurdle that the virus must overcome to have a productive spreading effect in vivo in the tumor.

Example 3: Extended Survival in a Patient Dog with Spontaneous Recurrent Malignant Glioma and Treated with T5.0002 Vector Plus 5-FC, but with Limited Apparent Vector Spread A male 35 kg Boxer dog, presenting with recurrent anaplastic oligodendroglioma 3 months following complete surgical resection, was treated with Toca 511 (purified and formulated in isotonic Tris/NaCl pH7.2, rendered isotonic with mannitol and sucrose, 1 mg/ml HSA, 0.1 mg/ml ascorbate) in combination with 5-FC. The tumor measured approximately 13 cm$^3$, and caused major lateral ventricle compression and significant midline shift. Due to the large size of the tumor, Toca 511 was infused through 2 separate catheters (400 μL and 480 μL), using Convection Enhanced Delivery (CED). The total Toca 511 dose administered was approximately 4.1×10$^6$ TU/g brain. ProHance® (gadoteridol) was added to Toca 511 prior to injection to allow visualization of delivery by MRI. The volume of distribution of the vector was estimated to be approximately 10-12% of the tumor volume.

Toca 511 was allowed to spread for 8 days. The dog was treated with 5-FC at a divided dose of 130 mg/kg/day, by mouth, three times daily with food for 5 days. The dose was increased to 160 mg/kg/day for 2 more days (7 days of 5-FC total). A follow-up MRI showed no change in tumor size and some possible changes to the internal area of the tumor. After 21 days of viral spread, a second cycle of 5-FC was initiated at the higher dose of 160 mg/kg/day (divided, three times a day with food). The drug was stopped after the fifth day of dosing due to the development of rash.

MRI performed at 2 weeks after the first course of 5-FC and 2 weeks after the second course of 5-FC (7 weeks after treatment began) has shown that the tumor volume has plateaued while the rate of tumor growth declined. The subject became more alert, active and remained clinically stable 13 weeks after injection of vector. The subject succumbed to a gastro-intestinal bleed at 15+ weeks, related to the extended administration of high dose steroids, and unrelated to the tumor. The estimated lifespan of the dog was no more than 3-4 weeks at the time of initial injection of the vector. Efficacy of the Toca 511/5-FC combination in this subject dog is shown by survival 3 to 4 times longer than that originally estimated by his attending veterinarian. At autopsy, PCR of tissue and blood showed no detectable vector in any tissue except in the tumor where one of three tissue samples was positive at 29 vector copies/ug genomic DNA. Thus this subject dog showed a marked clinical response, but the extent of vector spread after the second course of 5-FC appeared to be somewhat limited, suggesting that enhancement of spread could lead to further efficacy in dog and possibly other patients with glioma.

Example 4: Inhibition of JAK1/2 Signaling Blocks Interferon Antiviral Action to Enhance Replication Competent Recombinant Retroviral Vector Spread in Subcutaneous Tumors The objective of this study is to determine whether cellular JAK1/2 inhibition by Ruxolitinib (INCB-019424) results in increased replication competent recombinant retroviral vector spread in CT26 subcutaneous tumors. Jak1 and Jak 2 are downstream components of the type I interferon receptor complex.

Female BALB/c mice (age ~8 weeks) are purchased from The Jackson Laboratory (Bar Harbor Me.). Mice are acclimated for 7 days after arrival before undergoing surgical injection of cancer cells.

CT26 (ATCC) murine cancer colon cells are cultured in Dulbecco's modified Eagles medium with 10% fetal bovine serum, sodium pyruvate, and Glutamax (Hyclone, Logan Utah, and Invitrogen, San Diego Calif.). Cells are resuspended in PBS (Hyclone, Logan Utah) for implantation. CT26 cells (5×10$^4$ in 100 ul) are injected into the right flank of BALB/c mice.

Preparations of replication competent retrovirus GFP vectors encoding GFP (T5.0006 and T5.0002, see WO 2010/036986 and WO 2010/045002) were made and purified as previously described and all have titers of approximately 1×10$^6$ TU/ml. Vector is administered intra-tumorally in a volume of 100 ul or less for a minimum total dose/mouse of approximately 10$^6$ TU/mouse.

Ruxolitinib (INCB-019424) is a potent orally available inhibitor of JAK1, JAK2, and JAK3 (IC$_H$'s: 3 nM; 5 nm; and 332 nM, respectively). Ruxolitinib has been developed by Incyte Corp and Novartis AG.

Three groups of female BALB/c mice (10 mice each group, 9-10 weeks of age) are injected with 5×10$^4$ CT26 and/or 5×10$^4$ EMT6 cells in the right flank and tumors are allowed to grow until they reach 50-175 mm$^3$ in size. Tumors at 50-175 mm$^3$ are used to initiate oral gavage (OG) drug dosing (Day 0) of the mice and subsequent intratumoral vector injection. Group one receives intratumoral injection of MLV-GFP vector only. Group 2 receive OG drug at 10 mg/kg ruxolitinib suspended in 0.5% methylcellulose the day before, the day of vector injection, and for two days after injection of MLV-GFP vector, and Group 3 receives OG drug only on the day of injection of RMLV-GFP vector.

Analysis of percentage of GFP positive cells is carried out when tumor reach between 1000-2000 mm$^3$. Tumors are removed and processed for single cell analysis by cytometry. Data is analyzed and graphs are plotted by Flowjo software or equivalent. P values of <0.05 are considered statistically significant in all analyses, which are performed with Prism 5 statistical software (GraphPad Software).

Inhibition of JAK1/2 signaling results in a markedly higher percentage of GFP positive cells. This increased percentage is reflective of increased replication competent recombinant retroviral vector spread in the presence of the inhibitor, administered either on the day of initial infection only (group 3) or daily from 1 day before hand to 2 days after the vector injection (group 2) as opposed to spread in the absence of inhibitor (group 1).

Example 5: IFN Selection and Viral Replication in Parental Vs Interferon-Resistant CT26 Cells in the Presence and Absence of Exogenous IFNα

Early passage of a mouse colorectal carcinoma cell line CT26 (ATCC CRL-2638) was cultured in complete culture medium in the presence of mouse-specific IFNα for selection of IFNα-resistant cells. A mixture of recombinant mouse interferon alpha A and recombinant interferon alpha 4 (PBL Interferon Source) at 1,340 units/mL was used for selection of IFNα-resistant CT26 cells. Cells are continuously exposed to IFNα for 24 days. During the selection cells were passaged every 3-4 days. At the end of high dose exposure to IFNα, cells survived from the selection were designated as interferon-resistant cells and were subsequently expanded in the absence of IFNα.

Figure 4:
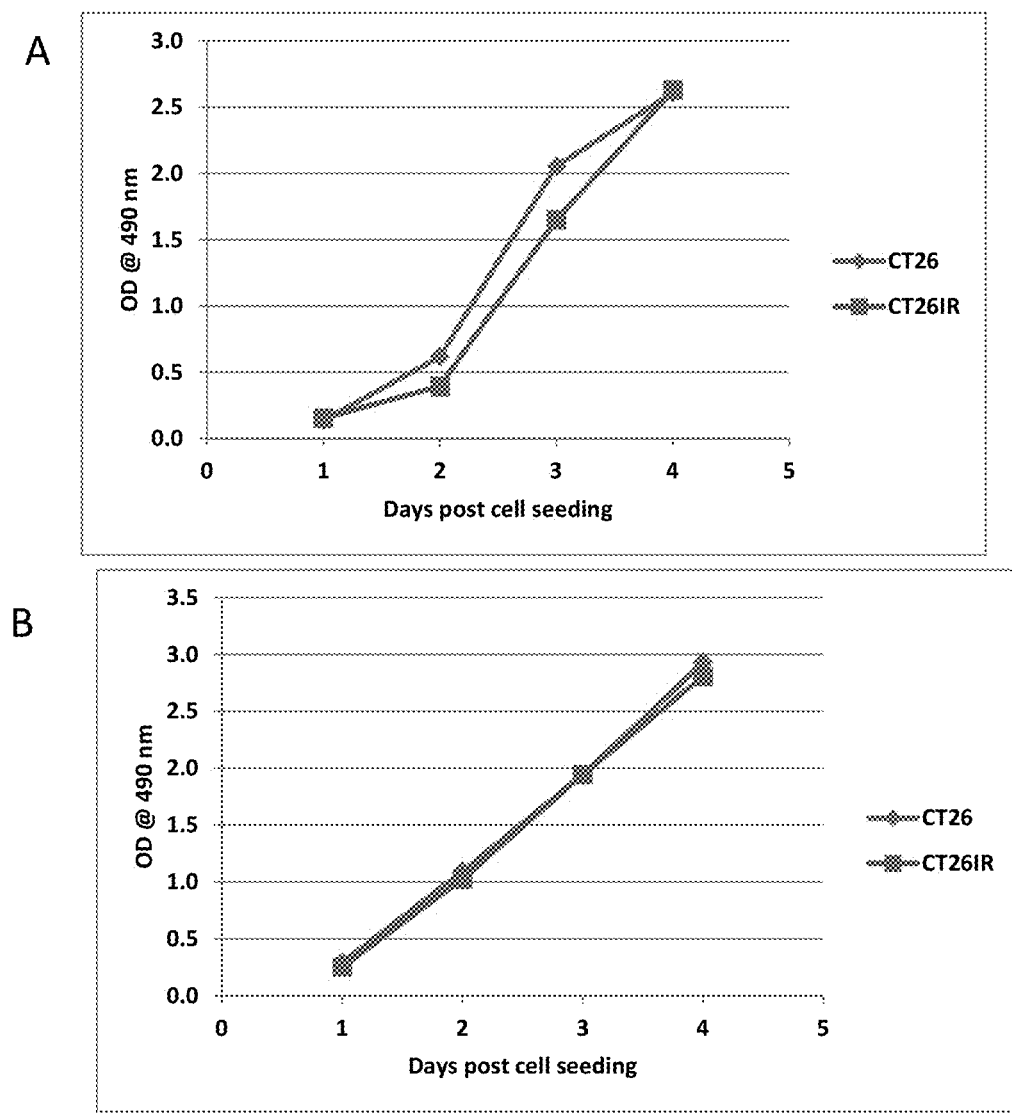
FIG. 4 shows the comparison of cell proliferation between parental and interferon-alpha-resistant CT 26 cells: A. after 3 passages (day 6-9 post interferon selection); and B. after passage 5 (day 12-15 post interferon selection).

Cell proliferation of interferon-resistant cells vs. parental cells was determined by MTS assay as cell proliferation is a central driving force for MLV-based vector replication. The result shows that the cell proliferation between the two were comparable both at cell passage 3 (day 6-9 post interferon selection) and passage 5 (day 12-15 post interferon selection) (FIG. 4). It is important to note that this is the time frame of which the viral replication kinetics of MLV-based vector expressing GFP is examined.

Figure 5:
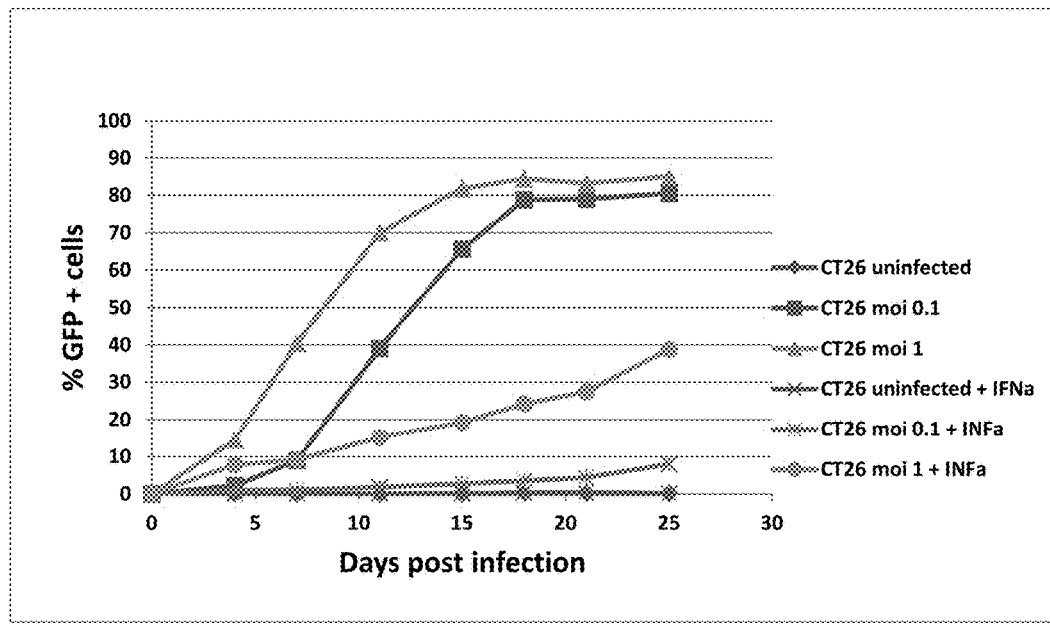
FIG. 5 shows the viral replication kinetics of a RRV expressing GFP in parental CT26 cells in the presence and absence of exogenous IFNα.

Parental and interferon-resistant cells with similar cell passage number were seeded to compare viral replication kinetics of a Toca 511 related MLV-based vector that contains a GFP marker gene in the presence and absence of IFNα. For cells treated with exogenous IFNα, a mixture of recombinant mouse interferon alpha A and recombinant interferon alpha 4 at 1,340 units/mL was added in culture daily to induce IFNα-mediated anti-viral activity. Cells were continuously exposed to IFNα until maximal infectivity is reached in cells treated without IFNα. The viral replication was assessed at MOI of 0.1 and 1 in both parental and interferon-resistant cells. The percentage of GFP positive cells at each cell passage indicates the extent of viral infectivity in a cell population. The result in FIG. 5 shows that IFNα-induced antiviral activity in parental CT26 cells attenuates viral spread at both MOIs and in a viral load-dependent manner.

Figure 6:
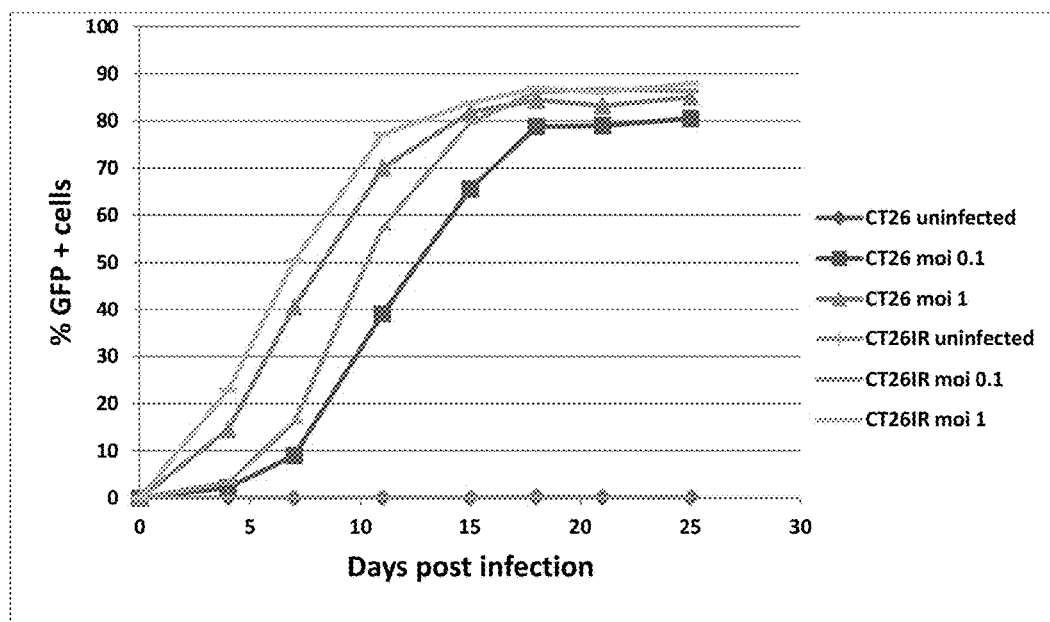
FIG. 6 shows viral replication kinetics of a RRV vector expressing GFP in parental versus interferon-alpha-resistant CT26 cells in the absence of exogenous IFNα.

Comparison of viral replication between parental and interferon-resistant CT26 cells in the absence of exogenous IFNα shows that viral spread is faster in interferon-resistant cells than in parental cells at both MOIs (FIG. 6). As the cell proliferation are comparable between the parental and IFN-resistant cells, the faster viral replication kinetics observed in interferon-resistant cells is contributed by the attenuation of basal antiviral activity.

Figure 7:
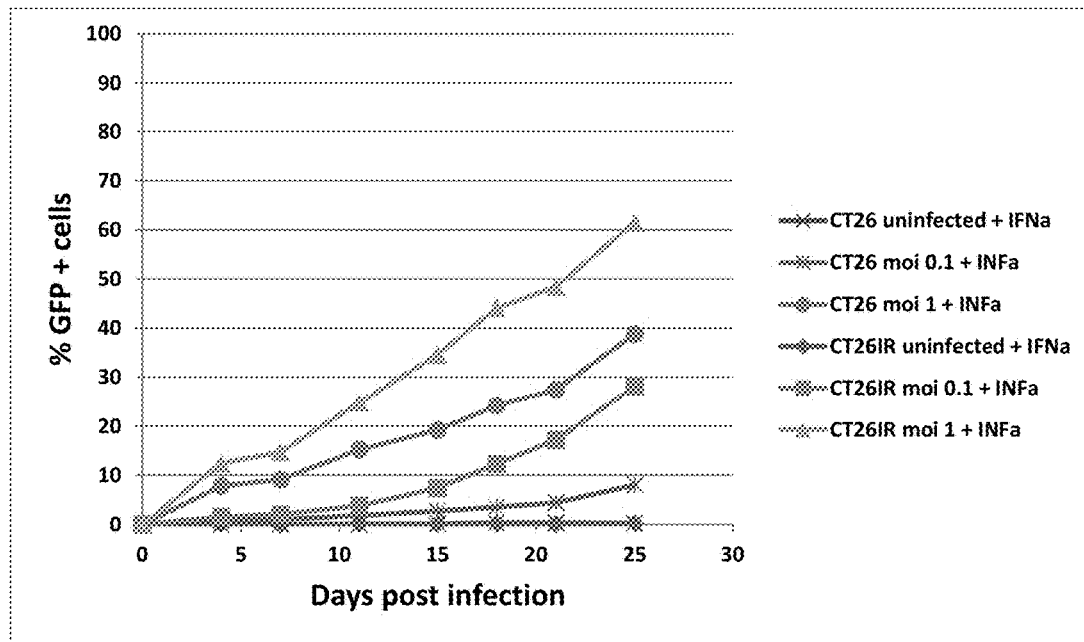
FIG. 7 shows viral replication kinetics of a RRV vector expressing GFP in parental versus interferon-alpha-resistant CT26 cells in the presence of exogenous IFNα.

Similarly, comparison of viral replication between parental and interferon-resistant CT26 cells in the presence of exogenous IFNα shows that viral spread is faster in interferon-resistant cells than in parental cells at both MOIs (FIG. 7). The faster viral replication kinetics observed in interferon-resistant cells is contributed by the partial resistance, as a result of prolonged IFNα selection, to IFNα-induced antiviral activity.

Example 6: IFN Selection and Viral Replication in Parental Vs Interferon-Resistant Tu2449 Cells in the Presence and Absence of Exogenous IFNβ

Early passage of a mouse glioma cell line Tu2449 (Weissenberger et al., 1997) was cultured in complete culture medium in the presence of mouse-specific IFNβ for selection of IFNβ-resistant cells. Recombinant mouse IFNβ (PBL Interferon Source) at 500 units/mL is used for selection of IFNβ-resistant Tu2449 cells. Cells are continuously exposed to IFNβ for 24 days. During the selection cells are passaged every 3-4 days. At the end of high dose exposure to IFNβ, cells survived from the selection were designated as interferon-resistant cells and were subsequently expanded in the absence of IFNβ.

Cell proliferation of interferon-resistant cells vs. parental cells was determined by MTS assay as cell proliferation is a central driving force for MLV-based vector replication. The result shows that the cell proliferation between the two are comparable both at cell passage 3 (day 6-9 post interferon selection) and passage 5 (day 12-15 post interferon selection). It is important to note that this is the time frame of which the viral replication kinetics of MLV-based vector expressing GFP is examined.

Parental and interferon-resistant cells with similar cell passage number are seeded to compare viral replication kinetics of a Toca 511 related MLV-based vector that contains a GFP marker gene in the presence and absence of IFNβ. For cells treated with exogenous IFNβ, recombinant IFNβ at 500 units/mL is added in culture daily to induce IFNβ-mediated anti-viral activity. Cells were continuously exposed to IFNβ until maximal infectivity is reached in cells treated without IFNβ. The viral replication is assessed at MOI of 0.1 and 1 in both parental and interferon-resistant cells. The percentage of GFP positive cells at each cell passage indicates the extent of viral infectivity in a cell population. The result shows that IFNβ-induced antiviral activity in parental Tu2449 cells attenuates viral spread at both MOIs and in a viral load-dependent manner.

Comparison of viral replication between parental and interferon-resistant Tu2449 cells in the absence of exogenous IFNβ shows that viral spread is faster in interferon-resistant cells than in parental cells at both MOIs. As the cell proliferation are comparable between the parental and IFN-resistant cells, the faster viral replication kinetics observed in interferon-resistant cells is contributed by the attenuation of basal antiviral activity.

Similarly, comparison of viral replication between parental and interferon-resistant Tu2449 cells in the presence of exogenous IFNβ shows that viral spread is faster in interferon-resistant cells than in parental cells at both MOIs. The faster viral replication kinetics observed in interferon-resistant cells is contributed by the partial resistance, as a result of prolonged IFNα selection, to IFNβ-induced antiviral activity.

Example 7: Improved Vector Spread with a Murine Colorectal Cell Line that is Resistant to IFN-Alpha (CT26IR) in a Subcutaneous Tumor Model The objective of this study is to compare the spread of an MLV based replication-competent retroviral vector carrying GFP protein, when delivered via subcutaneous injection in immune-competent (BALB/c) mice bearing a murine colorectal cell line that is either sensitive (CT26) or resistant (CT26IR) to IFN-alpha in a mouse subcutaneous tumor model. Female BALB/c mice (age ~8 weeks) are purchased from The Jackson Laboratory (Bar Harbor Me.). Mice are acclimated for 7 days after arrival before undergoing subcutaneous tumor implantation.

CT26 and CT26IR mouse colorectal carcinoma cells are cultured in Dulbecco's modified Eagles medium with 10% fetal bovine serum, sodium pyruvate, and Glutamax (Hyclone, Logan Utah, and Invitrogen, San Diego Calif.). Cells are resuspended in PBS (Hyclone, Logan Utah) for implantation. CT26 or CT26IR cells ($5\times10^4$ in 100 ul) are injected into the right flank of BALB/c mice.

Replication competent retrovirus vectors preparations are made as described above and all have titers of approximately $1 \times 10^6$ TU/ml. Vector is administered it in a volume of 100 ul for a minimum total dose/mouse of approximately $10^6$ TU/mouse.

One group of female BALB/c mice (10 mice, 9-10 weeks of age) is implanted subcutaneously with CT26 tumor cells and the other group of 10 female BALB/c mice of the same age is implanted subcutaneously with CT26IR tumor cells (day 0). Both groups are dosed IT with GFP-vector when tumors reach 50-175 mm³ in size and vector spread within tumor is monitored by Flow cytometry.

Analysis of percentage of GFP positive cells is done when tumor reach between 1000-2000 mm³. Tumors are removed and processed for single cell analysis by cytometry. Data is analyzed and graphs are plotted by Flowjo software or equivalent. P values of <0.05 are considered statistically significant in all analyses, which are performed with Prism 5 statistical software (GraphPad Software) or equivalent.

Results from the FLOW cytometry analysis show that CT26IR tumors have a significantly higher percentage of GFP positive cells compared to CT26 tumor cells, indicating increased vector spread in cell line that is resistant to IFN-alpha compared to the control cells.

Example 8

The objective of this study is to compare the survival of immune-competent (BALB/c) mice bearing a murine colorectal cell line that is either sensitive (CT26) or resistant (CT26IR) to IFN-alpha, after subcutaneous administration of the novel MLV based replication-competent retroviral vector carrying cytosine deaminase (Toca 511) followed by intraperitoneal (IP) delivery of 5-FC in a mouse subcutaneous tumor model.

Female BALB/c mice (age ~8 weeks) are purchased from The Jackson Laboratory (Bar Harbor Me.). Mice are acclimated for 7 days after arrival before undergoing subcutaneous tumor implantation.

CT26 and CT26IR mouse colorectal carcinoma cells are cultured in Dulbecco's modified Eagles medium with 10% fetal bovine serum, sodium pyruvate, and Glutamax (Hyclone, Logan Utah, and Invitrogen, San Diego Calif.). Cells are resuspended in PBS (Hyclone, Logan Utah) for implantation. CT26 or CT26IR cells ($5 \times 10^4$ in 100 ul) are injected into the right flank of BALB/c mice.

Replication competent retrovirus vectors preparations are made by transient transfection (or from a producer cell line see WO2010148203) and all have titers of approximately $1 \times 10^6$ TU/ml. Vector is administered intratumorally (IT) in a volume of 100 ul or less for a minimum total dose/mouse of approximately $10^6$ TU/mouse.

One group of female BALB/c mice (10 mice, 9-10 weeks of age) is implanted subcutaneously (right flank) with CT26 tumor cells and another group of 10 female BALB/c mice of the same age is implanted subcutaneously (right flank) with CT26IR tumor cells on day 0. Both groups are dosed IT with vector Toca 511 when tumors reach 50-175 mm³ in size. 7 days after the vector dosing, 5-FC (500 mg/kg/dose) is administered IP BID for 4 consecutive days followed by 10 days of rest. 4 Cycles of the treatment is repeated.

Survival analysis is performed on both groups and plotted as a Kaplan Meyer plot. Survival curves are compared by the log-rank test. P values of <0.05 are considered statistically significant in all analyses, which are performed with Prism 5 statistical software (GraphPad Software) or equivalent.

Results from treatment with the vectors and 5-FC show that CT26IR tumors have a statistically significantly survival advantage as compared to CT26 tumor cells in this subcutaneous tumor model.

Example 9

The objective of this study is to compare the survival of immune-competent (BALB/c) mice bearing a murine glioma cell line that is either sensitive (CT26) or resistant (CT26IR) to IFN-alpha, after intracranial (IC) administration of the novel MLV based replication-competent retroviral vector carrying cytosine deaminase (Toca 511) followed by intraperitoneal (IP) delivery of 5-FC in a mouse intracranial tumor model.

Female BALB/c mice (age ~8 weeks) are purchased from The Jackson Laboratory (Bar Harbor Me.). Mice are acclimated for 7 days after arrival before undergoing surgical placement of an indwelling guide cannula with a 3.0 mm projection implanted into the right striatum, and are fitted with a cap containing a 3.5 mm projection. The stereotaxic coordinates are AP=+0.5 mm, ML=−1.8 mm (from bregma).

CT26 and CT26IR mouse colorectal carcinoma cells are cultured in Dulbecco's modified Eagles medium with 10% fetal bovine serum, sodium pyruvate, and Glutamax (Hyclone, Logan Utah, and Invitrogen, San Diego Calif.). Cells are resuspended in PBS (Hyclone, Logan Utah) for implantation. CT26 or CT26IR cells ($1 \times 10^4$ in 1 ul) are infused at 0.2 uL per minute (5 minutes, followed by a hold of 5 minutes) intracranially (IC) through an injection cannula.

Replication competent retrovirus vectors preparations are made by transient transfection (or from a producer cell line, see, e.g., PCT/US10/38996, incorporated herein by reference in its entirety) and all have titers of approximately $1 \times 10^8$ TU/ml. Vector is administered IC in a volume of 5 ul or less for a minimum total dose/mouse of approximately $10^3$ TU/mouse.

One group of female BALB/c mice (20 mice, 9-10 weeks of age) is implanted IC with CT26 tumor cells and the other group of 20 female BALB/c mice of the same age is implanted IC with CT26IR tumor cells (day 0). 10 mice from each group receive IC injection of Toca 511 of $10^3$ on day 4, and the other 10 mice receive IC injection of Toca511 of $10^4$ on day 4. 5-FC (500 mg/kg/dose) is administered IP BID for 4 consecutive days starting at days 10, 24, 38, and 52. 4 cycles of these 4 day treatments followed by 10 days of viral spread are repeated.

Survival analysis to day 60 is performed on both groups and plotted as a Kaplan Meyer plot. Survival curves are compared by the log-rank test. P values of <0.05 are considered statistically significant in all analyses, which are performed with Prism 5 statistical software (GraphPad Software) or equivalent.

Results from treatment with the vectors and 5-FC show that CT26IR tumors have a statistically significantly survival advantage in both $10^3$ and $10^4$ doses as compared to CT26 tumor cells in this murine intracranial tumor model.

Figure 8:
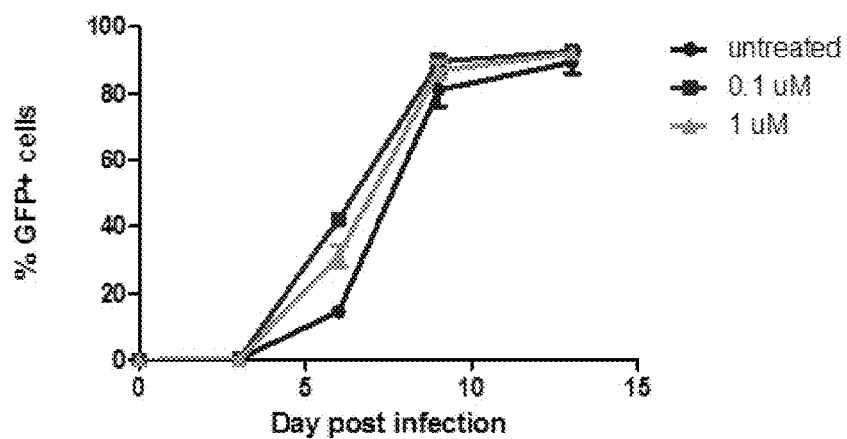
FIG. 8 shows the effect of dexamethasone on replication kinetics of T50006V at MOT of 0.01 in U87 cells.

Example 10: Dexamethasone Enhances Viral Spread of T50006 RRV in U-87MG and T98G Cell Lines Early passage of a human grade IV astrocytoma cell line U-87MG (ATCC, HTB-14) is cultured in completed culture medium in the presence or absence of dexamethasone (Sigma-Aldrich, D2915). Cells are treated with 0.1 and 1 µM concentration 6 h prior to initial viral infection and passaged every 3-4 days. Cells are continuously exposed to dexamethasone for 28 days and the drug is added to culture medium after each cell passage. No cell toxicity was observed during the course of treatment and a clear advantage in % GFP cells transduced is observed at Day 6. At later time points as the cells approach 100% infection, the difference becomes less marked (FIG. 8). These data show a clear advantage in RRV infection in the presence of dexamethasone, even in this readily infectable glioma cell line.

Figure 9:
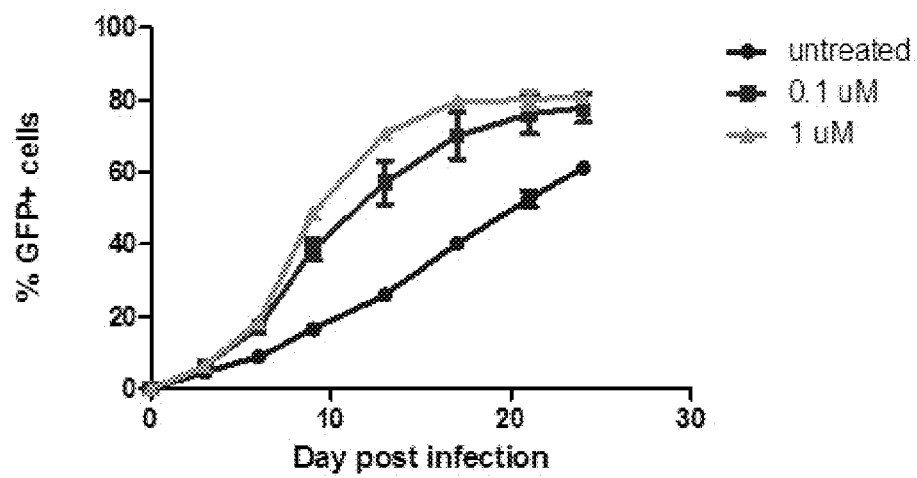
FIG. 9 shows the effect of dexamethasone on replication kinetics of T50006V at MOT of 0.1 in T98G cells.

Early passage of a human glioblastoma multiforme cell line T98G (ATCC, CRL-1690) is cultured in completed culture medium in the presence or absence of dexamethasone (Sigma-Aldrich, D2915). Cells are treated with at 0.1 and 1 µM concentration 6 h prior to initial viral infection and passaged every 3-4 days. Cells are continuously exposed to dexamethasone for 28 days and the drug is added to culture medium after each cell passage. No cell toxicity was observed during the course of treatment and a clear advantage in RRV infection and spread is observed at all time points after day 3, and for the duration of the experiment, in this human glioma cell line that infects less readily than the U87 line (FIG. 9).

In vivo testing was performed to determine correlation of the in vitro data using steroids. Female B6C3F1 mice (age ~8 weeks) underwent surgical placement of an indwelling guide cannula with a 3.0 mm projection implanted into the right striatum, and fitted with a cap containing a 3.5 mm projection. The stereotaxic coordinates are AP=+0.5 mm, ML=−1.8 mm (from bregma).

On Day 0, Tu2449 cells (1.4E4 cells in 1 µL) were implanted intracranially into all 4 groups of mice by infusion at 0.2 µL per minute (5 minutes, followed by a hold of 5 minutes) through an injection cannula with a 3.5 mm projection inserted through the guide cannula.

On Day 1, Groups 3 and 4 received steroid treatment (100 mg/kg) SC. On Day 4, Groups 1, 2 and 4 received IC (5 µL) vector of 6.3E4 TU/g of brain dose level and Group 3 received vehicle control. Starting on Day 10, Groups 2-4 began cycles of 5-FC (500 mg/kg in 800 µL, IP, BID) for 4 consecutive days, followed by 10 days off drug; Group 1 received PBS as control (800 µL, IP, BID). Survival was assessed for at least 4 cycles.

Figure 22:
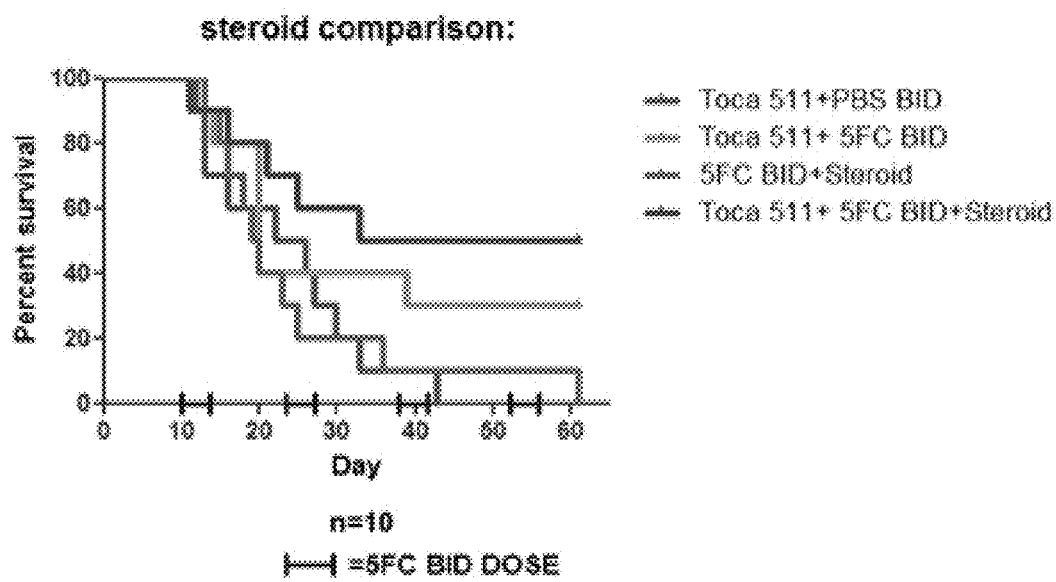
FIG. 22 shows a Kaplan-Meyer survival curve for mice receiving Toca 511 and 5-FC treatment either with or without steroid treatment.

Survival analysis to Day 60 was performed on 10 mice each from Groups 1-4 and plotted as a Kaplan-Meyer plot (FIG. 22). Survival curves are compared by the log-rank test. P values of <0.05 are considered statistically significant in all analyses, which are performed with Prism 5 statistical software (GraphPad Software) or equivalent.

Results from treatment with the combination of steroid and vector show a statistically significant survival advantage in this murine glioma model compared to treatment with vehicle, or steroid alone. However, combination of steroid and vector did not show a statistically significant survival advantage as compared to vector alone (p=0.3663).

In another experiment, male and female BALB/cJ mice (age 6-7 weeks) were purchased from Jackson Laboratories, Bar Harbor Me. Mice were acclimated for 11 days after arrival. Mice were randomized into the groups shown below.

| Group | Treatment | # males | #females | steroid | sacrifice |
|---|---|---|---|---|---|
| 1 | Vehicle | 3 | 3 | — | D10 |
| 2 | T5.0002 2.35 × 10$^6$ TU | 5 | 5 | — | D10 |
| 3 | T5.0002 2.35 × 10$^6$ TU | 5 | 5 | Start day −3 | D10 |

Dosing Procedures. For Group 3 only, methylprednisolone acetate (Depo-Medrol), 400 mg/kg, was administered subcutaneously (SC) at day −3. In a pilot study, this dose was found to suppress white blood cell count below normal range for at least 10 days.

Toca 511 or vehicle was administered by stereotaxic injection into the right frontal lobe. After anesthetizing the mice and preparing the skull, a small burr hole was drilled through the bone at coordinates AP=+0.5 mm and ML=−2.5 mm from bregma. A Hamilton syringe was lowered into the brain −2.5 mm (females) or −2.8 mm (males) DV from dura and 5 µL of Toca 511 or vehicle injected at a rate of 1 µL per minute. After a hold of 5 minutes, the syringe was withdrawn, the hole sealed with bone wax, the skin closed, and the animal recovered from surgery. To minimize discomfort, ketoprofen was administered SC.

Tissue collection. On day 10, all animals were euthanized and selected tissues and fluids collected using disposable equipment to minimize possible cross-contamination of vector negative by vector positive tissues. DNA was prepared in a dedicated isolation facility to further ensure that DNA sequence contamination did not occur, and assessed by qPCR using the MLV LTR primer and probe set described in Example 1 to measure the copies/microgram. Assays were performed in triplicate.

Figure 23:
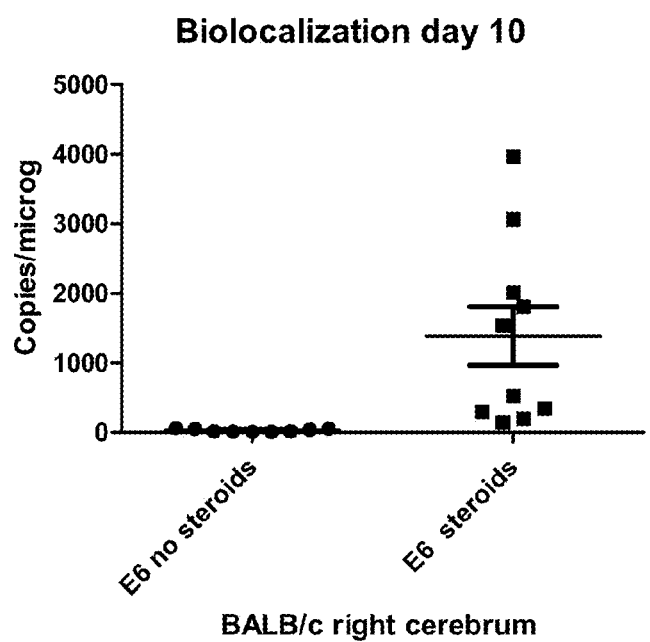
FIG. 23 shows vector copy number in the presence and absence of steroids.

No vector positivity was observed in the control group in any tissue. In both groups 2 and 3 there was no significant vector positivity except in the brain. At the site of injection (right cerebrum) group 3 (steroids) had a mean of 1387+/−421 (SE) copies/microgm more than 40 fold greater than the group 2 animals [mean of 30+/−8 (SE) copies/microgm]. This was significantly different at the level of p<0.0001 by the two sided Mann-Whitney statistical test. The data is shown in FIG. 23.

Example 11: Detection of FBAL (5-FC Catabolite, Alpha-Fluoro-Beta-Alanine) in Mouse Plasma as a Marker for 5-FC Conversion by Toca 511 in a Mouse Glioma Model The vector backbone, design, and production are previously described.

Figure 10:
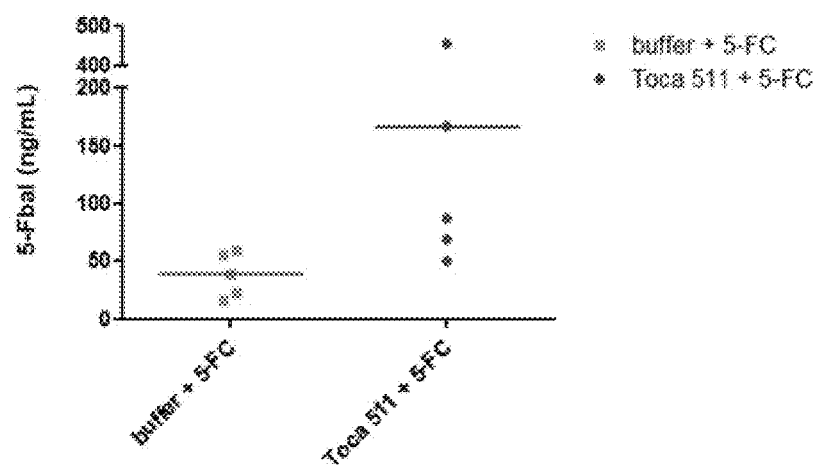
FIG. 10 shows an analysis of plasma FBAL in mice after transcranial, intratumoral administration of either buffer or Toca 511 and oral administration of 5-FC.

Syngeneic Tu-2449 glioma cells were implanted into the striatum of B6C3F1 mice. The mice were then administered either Toca 511 vector or PBS directly into the established tumors. 5-FC was given orally to both groups for 2 consecutive days (250 mg/kg, BID), then one final dose of 5-FC (250 mg/kg) was administered orally one hour before blood collection from these mice. Plasma was separated from whole blood and stored at −80° C. FBAL quantification in plasma was performed using high-performance liquid chromatography (HPLC) with mass spectrometry. Briefly, mouse plasma containing FBAL were isolated with a liquid-liquid extraction and analyzed with HPLC using a Prism RP column. The mobile phase was nebulized using heated nitrogen in a Z-spray source/interface set to electrospray negative ionization mode. The ionized compounds were detected using MS/MS. This method is applicable for measuring concentrations ranging from 10.0 to 10,000 ng/mL. FBAL could be measured in Toca 511/5-FC treated mice above the background from control mice treated with 5-FC alone (FIG. 10). Thus analysis of plasma FBAL can be used as a surrogate marker for Toca 511 activity in brain tumor.

Example 12: Anti-Tumor Efficacy Studies with the Combination of IFN-Blocking Antibody and Vector in a Mouse Glioma Model The objective of this study is to determine if IFN-blocking antibody facilitate Toca 511 vector spread by assessing survival in a murine intracranial glioma model.

Female B6C3F1 mice (age ~8 weeks) underwent surgical placement of an indwelling guide cannula with a 3.0 mm projection implanted into the right striatum, and fitted with a cap containing a 3.5 mm projection. The stereotaxic coordinates are AP=+0.5 mm, ML=−1.8 mm (from bregma).

On Day 0, Tu2449 cells (1.4E4 cells in 1 µL) were implanted intracranially into all 4 groups of mice by infusion at 0.2 µL per minute (5 minutes, followed by a hold of 5 minutes) through an injection cannula with a 3.5 mm projection inserted through the guide cannula.

On Day 4, Groups 1 and 2 received IC (5 µL) vector of 6.3E4 TU/g of brain dose level, Group 4 received IC (5 µL) vector of 6.3E4 TU/g of brain dose level and IFN-blocking antibody (4 mg/mL), and Group 3 received vehicle control. Mice in Groups 3 and 4 received two more injections of IFN-blocking antibody IC via the injection cannula (5 µL of 4 mg/mL) at Day 6 and 8. Starting on Day 10, Groups 2-4 began cycles of 5-FC (500 mg/kg in 800 µL, IP, BID) for 4 consecutive days, followed by 10 days off drug; Group 1 received PBS as control (800 µL, IP, BID). Survival was assessed for at least 4 cycles.

Figure 11:
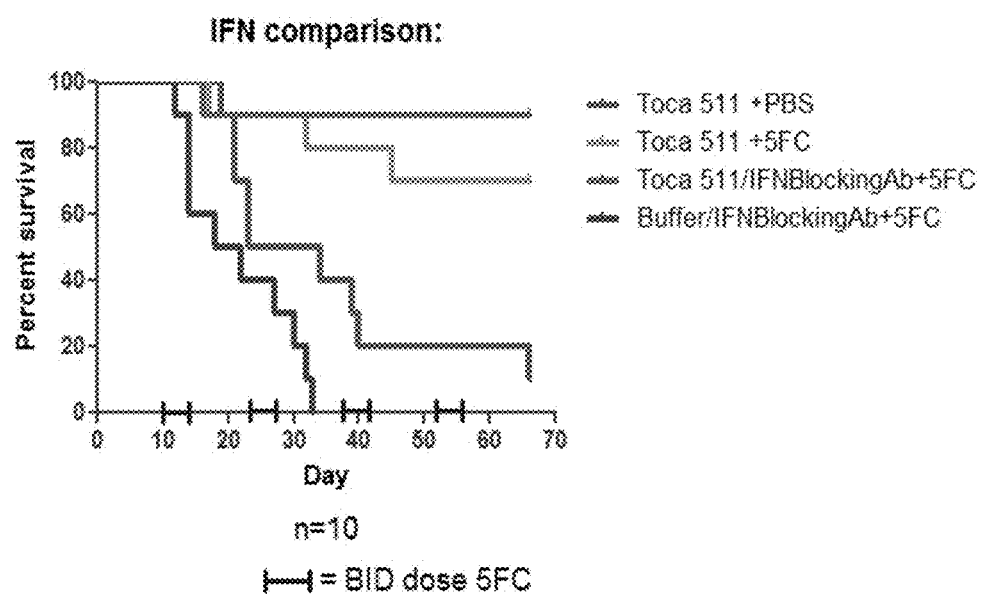
FIG. 11 shows a Kaplan Meyer survival graph for groups of 10 B6C3F1 mice with an implanted intracranial tumor, injected intracranially into the tumor with Toca 511 or PBS, and subsequently treated with 5-FC (500 mg/kg) BID for 4 days on 10 days off as shown.

Survival analysis to Day 60 was performed on 10 mice each from Groups 1-4 and plotted as a Kaplan-Meyer plot (FIG. 11). Survival curves are compared by the log-rank test. P values of <0.05 are considered statistically significant in all analyses, which are performed with Prism 5 statistical software (GraphPad Software) or equivalent.

Results from treatment with the combination of IFN-blocking antibody and vector+5-FC show a statistically significant survival advantage in this murine glioma model compared to treatment with vehicle, or IFN-blocking antibody alone. However, combination of IFN-blocking antibody and vector+5-FC did not show a statistically significant survival advantage as compared to vector+5-FC (p=0.3154).

Example 13: Anti-Tumor Efficacy Studies with Gamma Interferon Expressing Vector in a Mouse Subcutaneous Tumor Model The objective of this study is to assess the effect of a novel MLV based replication-competent retroviral vector carrying the murine gamma interferon sequence (pAC3-mIFNg) on tumor growth, when delivered via intratumoral (IT) injection in BALB/c mice bearing subcutaneous colon carcinoma (CT26.WT).

Female BALB/c mice (age ~8 weeks) are purchased from Jackson Laboratories (Bar Harbor, Me.). Mice will be acclimated for 7 days after arrival before start of studies.

CT26.WT cells (ATCC, Manassas Va.) are an N-nitroso-N-methylurethane-(NNMU) induced, undifferentiated colon carcinoma cell line. Cells are cultured in Dulbecco's modified Eagles medium with 10% fetal bovine serum, sodium pyruvate, and Glutamax (Hyclone, Logan Utah, and Invitrogen, San Diego Calif.). Cells are resuspended in PBS (Hyclone, Logan Utah) for implantation. CT26.WT cells (2E5 in 100 µL) are injected into the right flank of BALB/c mice.

Vectors preparations are made by transient transfection (or from a producer cell line after infection of a second cell line with the infectious virus from the initial transfection; U.S. application 61/218,063) with titers of approximately 3E6 TU/ml. For initial studies vector is not further purified or concentrated. For follow on experiments to determine full dose response curves, high titer purified material is prepared with a titer expected around 10E8/ml. To achieve high titer material, canine cell line CF2 are chosen for production as gamma interferon is poorly cross-species reactive and use of xenogeneic cell lines will prevent the inhibitory action of gamma interferon on the producing cells. The vector is purified and concentrated as described in the specification. Vector is administered IT in a volume of 100 µL and the total dose/mouse of approximately 3E3, 3E4 and 3E5 TU/mouse. Vector expressing gamma interferon is identified as Toca 621.

Nine groups of female BALB/c (99 mice, 9-10 weeks of age) are implanted subcutaneously with CT26.WT tumor cells (Day 0) and then dosed (day 4-7 depending on growth rate of the CT26 tumor; approximately 50-100=$^3$) with vehicle (Groups 1), with control vector [AC3-GFP(V), (Group 2), IT Toca 621 vector injection (Groups 3-5), or intravenous Toca 621 vector injection (group 6-8). Group 9 mice have no tumor implanted and are intravenously injected with vector only.

Tumor growth analysis is carried out to 2000 mm$^3$ or to 60 days based on which ever comes first. 10 mice from each group will be plotted for tumor size over time. Statistical significance will be determined using analysis of variance (ANOVA). P values of <0.05 are considered statistically significant in all analyses, which are performed with Prism 5 statistical software (GraphPad Software) or equivalent. In-life observations are also taken to assess any adverse events to Toca 621 administration.

The results of measurement of tumor size over time show a statistically significant difference in the growth of tumors treated with the vector expressing gamma IFN over the tumors in animals that received control vector or vehicle

Example 14: Intravenous Gene Delivery Using a Replicative Retroviral Vector

The objective of this study was to assess the effectiveness of intravenous delivery of a novel MLV based replication-competent retroviral vector carrying the marker green fluorescent protein (AC3-GFP(V)) to U87 gliomas implanted in the brains of nude mice.

Female athymic nude-Foxn1^nu (nude) mice (age ~8 weeks) were purchased from Harlan (Indianapolis Ind.). Mice were acclimated for 7 days after arrival. Mice underwent surgical placement of an indwelling guide cannula with a 3.0 mm projection implanted into the right striatum, and fitted with a cap containing a 3.5 mm projection. The stereotaxic coordinates are AP=+0.5 mm, ML=−1.8 mm (from bregma).

U-87 MG cells (ATCC, Manassas Va.) are derived from a malignant glioma from a 44 year old Caucasian female. Cells were cultured in Dulbecco's modified Eagles medium with 10% fetal bovine serum, sodium pyruvate, and Glutamax (Hyclone, Logan Utah, and Invitrogen, San Diego Calif.). Cells are resuspended in PBS (Hyclone, Logan Utah) for implantation. U-87 MG cells (1E5 in 1 µL) were infused at 0.2 µL per minute (5 minutes, followed by a hold of 5 minutes) intracranially (IC) through an injection cannula with a 3.5 mm projection inserted through the guide cannula.

Vector preparations were made by transient transfection and all had a titer of approximately 2.8E7 TU/ml. Vector was administered intratumorally (IT) in a volume of 5 ul or less for a minimum total dose/mouse of approximately 1.4E45 TU/mouse. Intravenous injections were done through the tail vein with 2.8E6/100 uL.

Five groups of female athymic nude-Foxn1^nu mice (16 mice, 9-10 weeks of age) were implanted IC with U-87 tumor cells (Day 0) then dosed IT or IV (day 4-7 depending on growth rate of the U87 cells) with vehicle IV (Group 1), with vector IV (Group 2), IT with a blood/brain barrier disruptor Vardenafil and vector (Group 3), IT with Vardenafil and vector (Groups 4), or IT with vector (group 5). 14 days after vector injection mice were sacrificed and tumors are isolated and analyzed for GFP expression.

Figure 12:
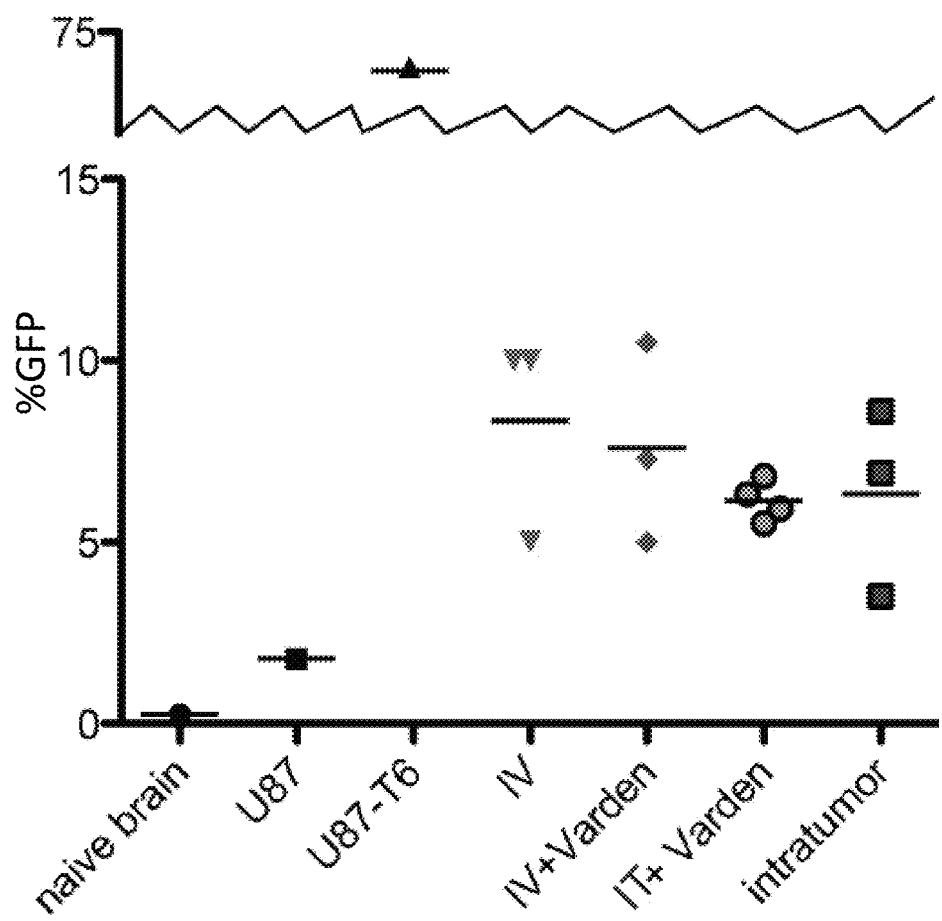
FIG. 12 shows flow cytometry analysis of GFP expression in U87 cells after intratumor or intravenous delivery of AC3-GFP vector in a nude mouse model. Cells are measured by flow cytometry for percent GFP positive. Cells isolated from naïve nude mouse brains, U87 cells from tissue culture, or U87 cells transduced at an multiplicity of infection of 1 with AC3-GFP(V) in vitro serve as controls.
Figure 13:
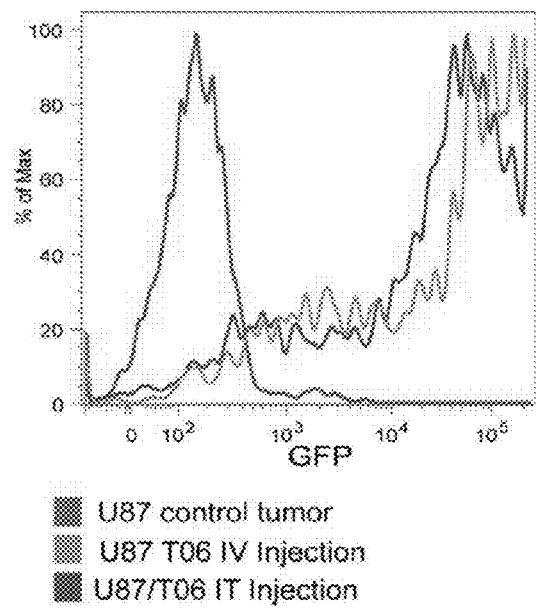
FIG. 13 shows a histogram analysis was also done on groups 1, 3 and 5 from example 27 (iv injection of GFP vector) to measure the distribution of GFP signal in isolated U87 cells. GFP expression is from U87 tumor cells isolated from mouse brains after 14 days after vector treatment.

U87 cells from disrupted tumors isolated from the mice were analyzed by flow cytometry for the percentage GFP positive from groups 2-5 (FIG. 12). Histogram analysis was also done on groups 1, 3, and 5 to measure the distribution of GFP signal in isolated U87 cells (FIG. 13).

Intravenous delivery of GFP was as equally effective as intratumor injection of U87 glioma cells intracranially implanted into nude mice.

Figure 14:
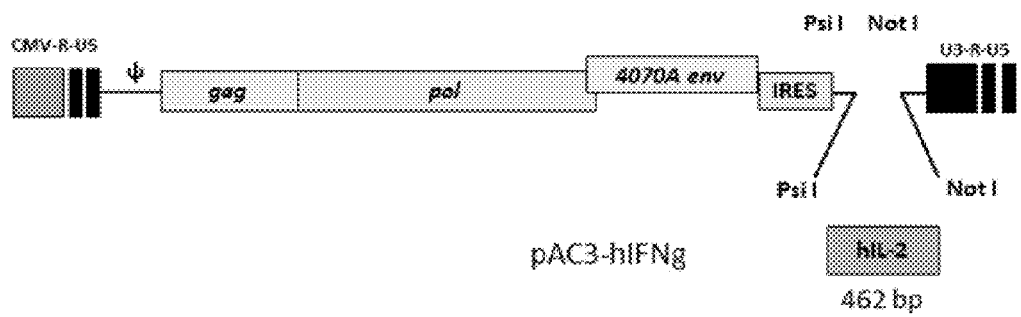
FIG. 14 is a schematic vector map of the MLV retroviral vectors encoding the human IL-2 in the pAC3 backbone.

Example 15: Construction of Replication Competent Retroviral Vector Encoding the Human IL-2 Gene The replication competent retroviral vector, pAC3-hIL2, encoding the human IL2 gene, is derived from the backbone of pAC3-yCD2 vector. The pAC3 backbone in the pAC3-hIL2 vector-encoding plasmid DNA was isolated by endonuclease digestion of the pAC3-yCD2 plasmid DNA with Psi I and Not I. The cDNA sequence of human IFN-γ gene was identified and confirmed using sequences obtained from different accession numbers (BC066255 and BC066257). Sequence alignment of the two revealed identical sequence. The open reading frame of the human IFN-γ was synthesized with Psi I and Not I restriction enzyme site present at each end of the DNA fragment for subsequent insertion at the corresponding site in the pAC3 backbone. The resulting construct, pAC3-hIL2, encodes 4 genes: the gag, the pol, the env, and the human IL2. (FIG. 14).

Vector stock is produced by transient transfection of the vector-encoding plasmid DNA into 293T cells using calcium phosphate method. Eighteen hours post transfection, the culture was replaced with fresh medium. Twenty-four hours post medium replacement, the supernatant containing the vector was collected and filtered through a 0.45 μm filter and used immediately or stored in aliquots at −80° C. for later use. Twenty micro-liter of the collected vector stocks was used to infect human prostate cancer cells, PC3. Twenty-four hours post infection, AZT was added to the cells to inhibit further viral replication. Forty-eight hours post infection, genomic DNA of infected PC3 cells was extracted for titer assay. The titer of the vector stocks was determined by qPCR with an inclusion of standards of known copy numbers.

The expression of human IL-2 is first tested at the RNA level. Total RNA is extracted from transduced CF2TH and HT1080 cells at 5 days post infection using standard RNA extraction method. RT-PCR was performed to detect the expression of human IL-2. Fifty nano-gram of total RNA was used in the RT reaction to generate cDNA. One tenth of the volume from RT reaction was subsequently used for PCR using PCR primer set specific for human IL-2. Result from RT-PCR shows that human IL-2 is expressed in HT1080 cells transduced with pAC3-hIL2 vector.

The expression of secreted human IL-2 protein was tested by standard ELISA. Vector stock collected from day 5 post infection was serially diluted in the ELISA assay in order to obtain a linear range between protein concentration and dilution factor. The result showed that human IL-2 protein is secreted at a higher concentration by the CF2TH cells than HT1080 at day 5 post infection.

Example 16: Anti-Tumor Efficacy Studies with Interleukin 2 Expressing Vector in a Mouse Subcutaneous Tumor Model The objective of this study is to assess the effect of a novel MLV based replication-competent retroviral vector carrying the murine leukocytotrophic hormone interleukin 2 (IL-2) sequence (pAC3-mIL2) on tumor growth, when delivered via intratumoral (IT) injection in BALB/c mice bearing subcutaneous colon carcinoma (CT26.WT).

Female BALB/c mice (age ~8 weeks) are purchased from Jackson Laboratories (Bar Harbor, Me.). Mice will be acclimated for 7 days after arrival before start of studies.

CT26.WT cells (ATCC, Manassas Va.) are an N-nitroso-N-methylurethane-(NNMU) induced, undifferentiated colon carcinoma cell line. Cells are cultured in Dulbecco's modified Eagles medium with 10% fetal bovine serum, sodium pyruvate, and Glutamax (Hyclone, Logan Utah, and Invitrogen, San Diego Calif.). Cells are resuspended in PBS (Hyclone, Logan Utah) for implantation. CT26.WT cells (2E5 in 100 μL) are injected into the right flank of BALB/c mice.

Vectors preparations are made by transient transfection (or from a producer cell line; refer to provisional) with titers of approximately 6E6 TU/ml. For initial studies vector is not further purified or concentrated. For follow on experiments to determine full dose response curves, high titer purified material is prepared with a titer expected around 10E8/ml. Vector is administered IT in a volume of 100 μL and the total dose/mouse of approximately 6E5 TU/mouse. Vector expressing gamma interferon is identified as Toca IL2.

Five groups of female BALB/c (55 mice, 9-10 weeks of age) are implanted subcutaneously with CT26.WT tumor cells (Day 0) and then dosed (day 4-7 depending on growth rate of the CT26 tumor; approximately 50-100 mm$^3$) with vehicle (Groups 1), with control vector [AC3-GFP(V), (Group 2), IT Toca IL2 vector injection (Groups 3), or intravenous Toca IL2 vector injection (group 4). Group 5 mice have no tumor implanted and are intravenously injected with vector only.

Tumor growth analysis is carried out to 2000 mm$^3$ or to 60 days based on which ever comes first. 10 mice from each group will be plotted for tumor size over time. Statistical significance will be determined using analysis of variance (ANOVA). P values of <0.05 are considered statistically significant in all analyses, which are performed with Prism 5 statistical software (GraphPad Software) or equivalent. In-life observations are also taken to assess any adverse events to IL-2 expression during treatment.

Delivery of IL-2 by replicating MLV reduces and in some instances clears tumors burden from the BALB/c CT26 mouse model.

Example 17: Efficient Delivery of Intravenously Injected Replication Competent Recombinant Retroviral Vector Containing the GFP Gene Across the Blood/Brain Barrier to Intracranial Tumors B6C3F1 mice undergo intracranial administration (Hamilton injection) into the right striatum of 1e4 Tu2449 cells administered/mouse on Day 0. Treatment for PBS control or vector started on day 3. The control group received 100 uL intravenous (IV) PBS, and all other groups received IV administration of MLV-GFP vector at 9E6 TU/100 ul (titer: 9E7 TU/mL) per day unless otherwise indicated. The 2 day IV dose group was given MLV-GFP on back to back days, the 3 day dose group on day 1, 3, and 5, and five straight days of IV MLV-GFP were delivered for the 5 day dose group. 14 days after vector injection, mice are directly visualized for GFP+ cells in the brain. Tumors are then surgically isolated from the brains and processed for analysis of GFP+ cells by flow cytometry. Spleens from the same mice are also processed for analysis of GFP+ cells.

Figure 15:
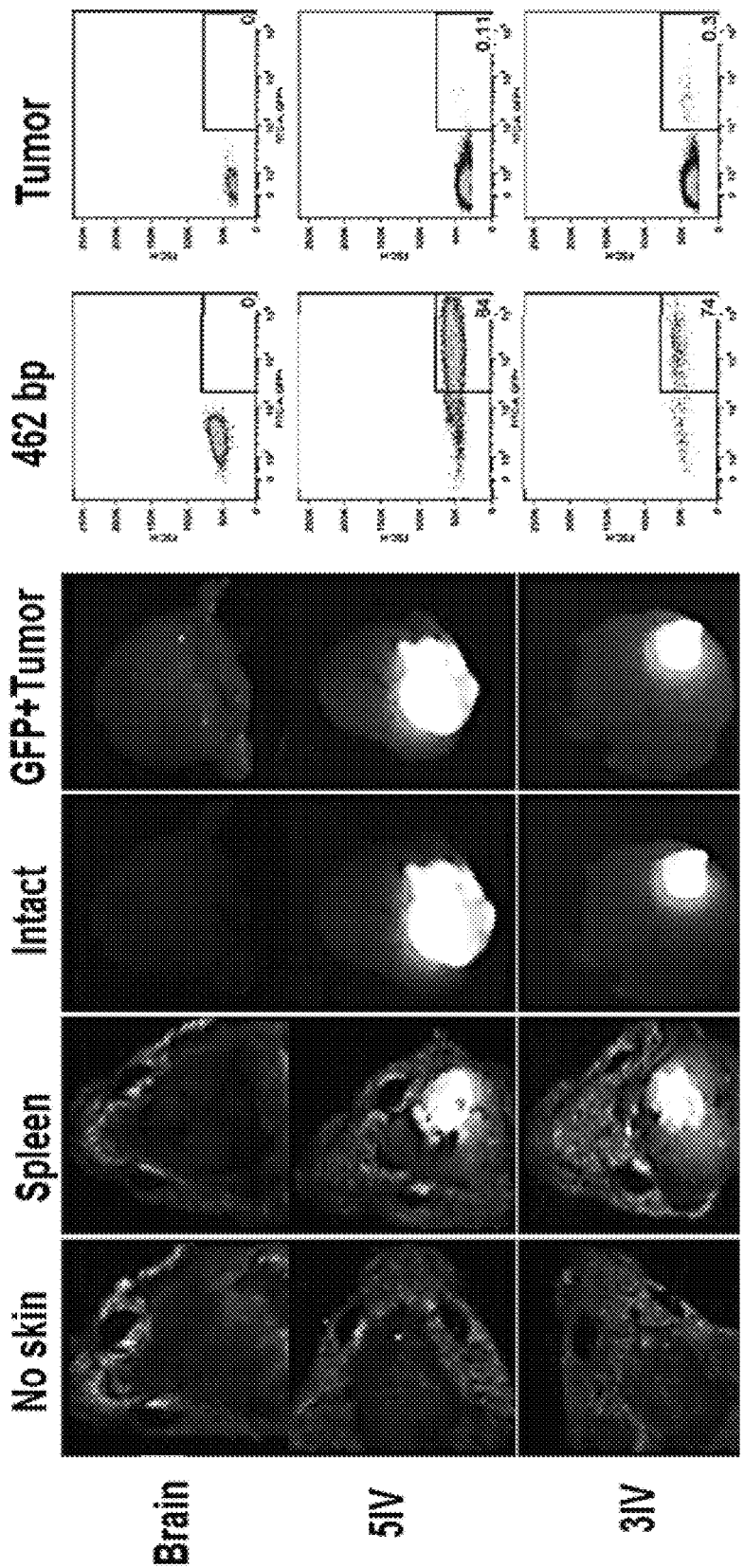
FIG. 15 shows the visualization and measurement of intracranial GFP+ tumors transduced with MLV-GFP 14 days after intravenous delivery of the MLV-GFP vector.
Figure 15:
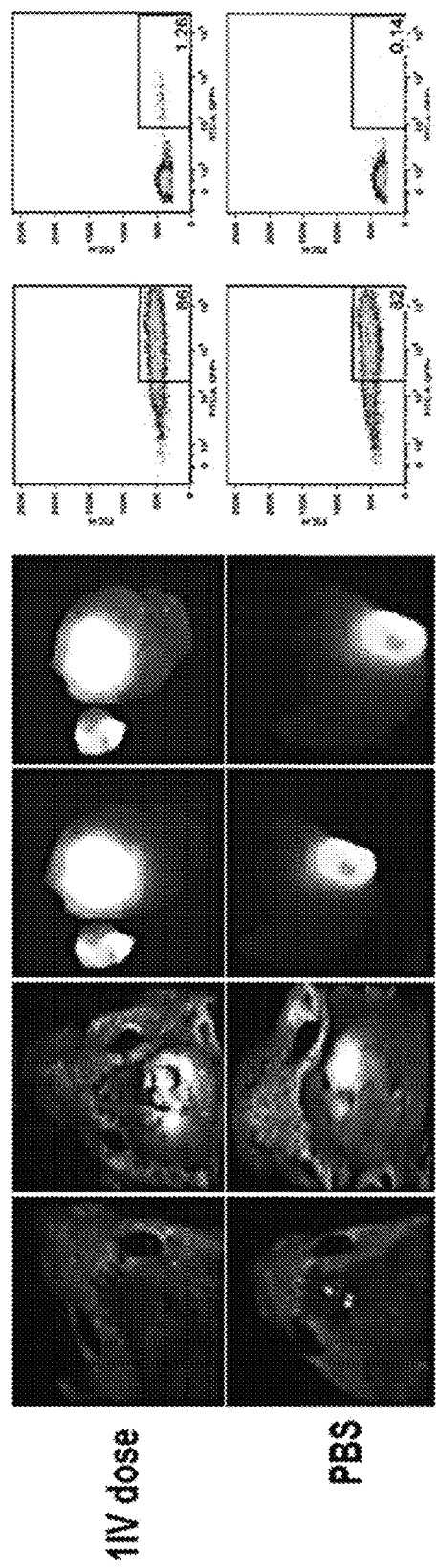
Figure 16:
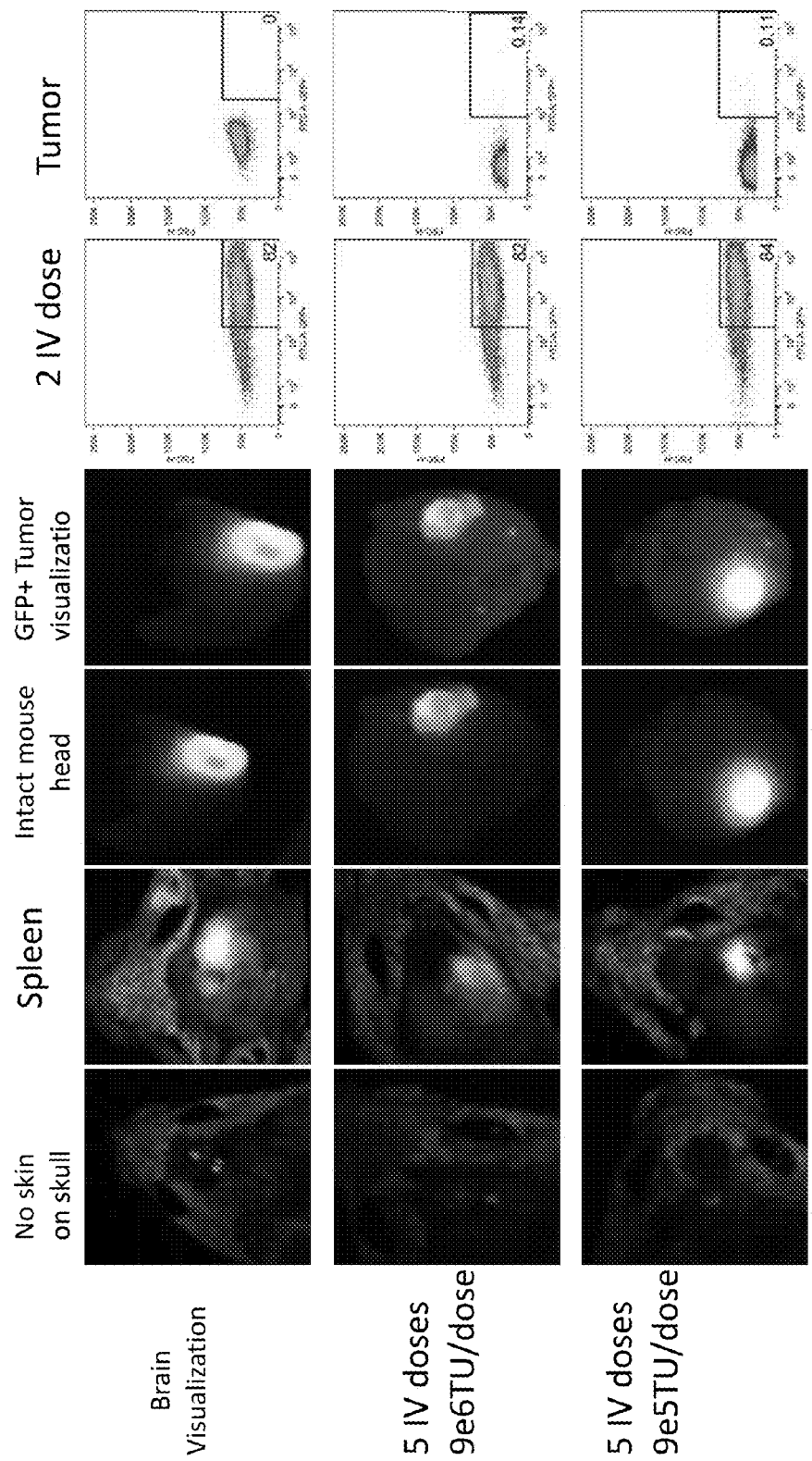
FIG. 16 shows the results of varying the vector TU dose levels in a 5 day course of intravenous MLV-GFP vector delivery to intracranial tumors.

All intravenous dose schedules, from one to five doses, were capable of transducing intracranial Tu2449 tumors in B6C3F1 mice 14 days after intravenous delivery of the MLV-GFP vector. Tumors had GFP levels higher than 74 percent positivity of Tu2449 cells in all mice dosed with at least one intravenous injection of 9e6 TU MLV-GFP. Ten fold dilutions of vector intravenously injected produced GFP+ tumors but not at the percent positive levels seen in the highest 9e6 TU dose groups. Analysis of cells isolated from the spleen showed minimal GFP+ cells further confirming the tumor-selective nature of the transducing replication competent retroviral vector (FIG. 15-16).

Example 18: Blocking IFNAR-1 Signaling Enhances Virus Spread and Uptake in Subcutaneous Tumors Objective: This study was undertaken to assess the effectiveness of blocking IFNAR-1 (Type 1 interferon Receptor) signaling towards increasing virus uptake and spread in a subcutaneous tumor model.

Methods and Materials: Female BALB/c mice (age ~8 weeks) were purchased from Jackson Laboratories (Bar Harbor Me.). Mice were acclimated for 7 days after arrival.

EMT6 cells (ATCC, Manassas Va.) are derived from a transplantable murine mammary carcinoma that arose in BALB/cCRGL mice. Cells were cultured in Dulbecco's modified Eagles medium with 10% fetal bovine serum, sodium pyruvate, and Glutamax (Hyclone, Logan Utah, and Invitrogen, San Diego Calif.). Cells are resuspended in PBS (Hyclone, Logan Utah) for implantation. EMT6 are subcutaneously injected into the right flank of BALB/c mice (5E4 cells/100 μL).

IFNAR-1 blocking antibody (4 mg/mL; Biolegend®, San Diego Calif.) was mixed at equal ratio with vector at time of intratumoral injection (50 μL each). Subsequent intratumoral injections were done at 50 μL.

Vector preparations had a titer of approximately 6.3E8 TU/ml. Vector was administered intratumorally (IT) in a volume of 100 μl for a total dose/mouse of approximately 6.3E7 TU/tumor/mouse.

Three groups of female BALB/c mice (30 mice, 9-10 weeks of age) were implanted subcutaneously with EMT6 tumor cells (Day j). When tumors reached a size between 50-150 mm$^3$, Group 1 tumors (10 mice) were directly injected with 100 μL PBS; Group 2 tumors (10 mice) were directly injected with vector mixed with IFNAR-1 blocking antibody (50 μL each); Group 3 tumors (10 mice) were directly injected with vector mixed with PBS (50 μL each). Group 2 tumors were subsequently injected daily with 50 μL IFNAR-1 blocking antibody for an additional 4 days. Group 1 mice were injected with PBS (800 L) and Group 2 and 3 mice were injected with 5-FC (500 mg/kg IP BID) 12 days after vector injection. Tumor volumes were measured two or three times a week from Group 1 (Toca 511+PBS), Group 2 (Toca 511+aIFN ab+5-FC), and Group 3 (Toca 511+5-FC). The study was terminated on Day 28 after tumor implantation. Serum from mice was collected for quantitation of FBAL (5-FU metabolite) by HPLC separation followed by mass spectrometer identification of FBAL (Microconstants San Diego Calif.). Tumors were collected for virus copy number per genome determination by qPCR analysis.

Figure 17:
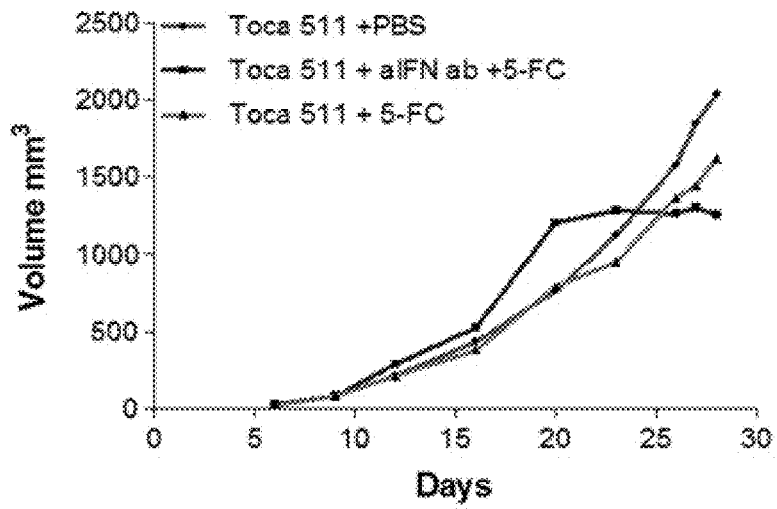
FIG. 17 shows the effect of anti-IFN antibody on tumor volume.
Figure 18:
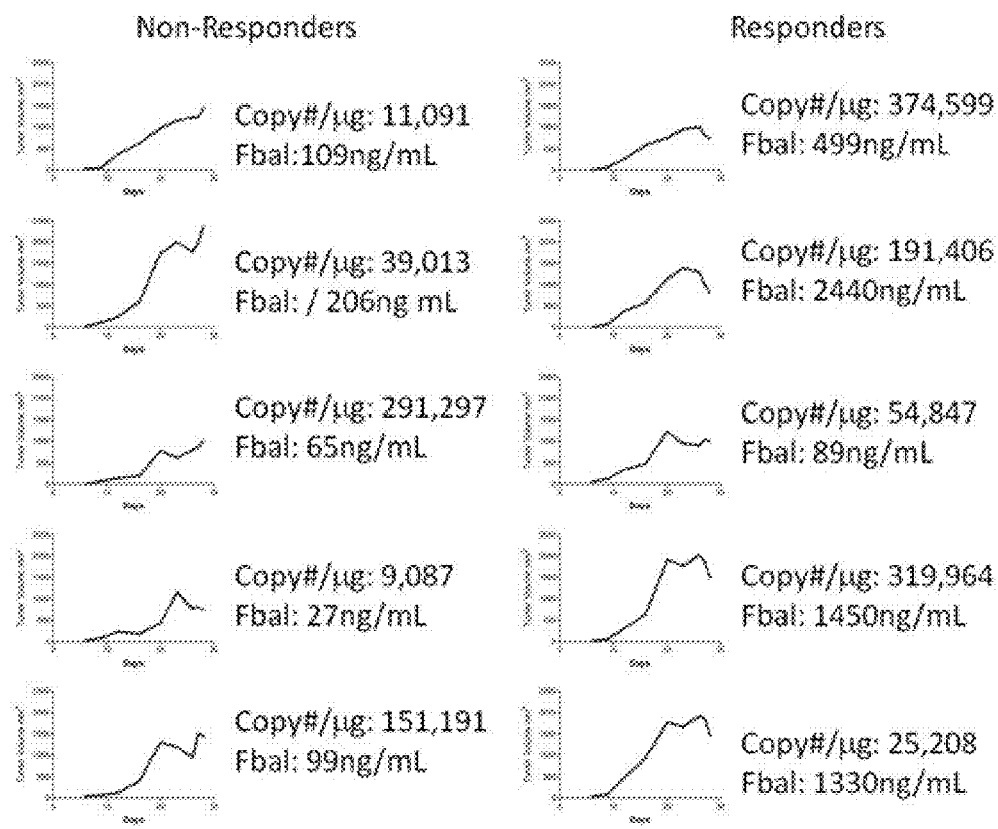
FIG. 18 shows copy number and FBAL measurements in responders and non-responders.
Figure 19:
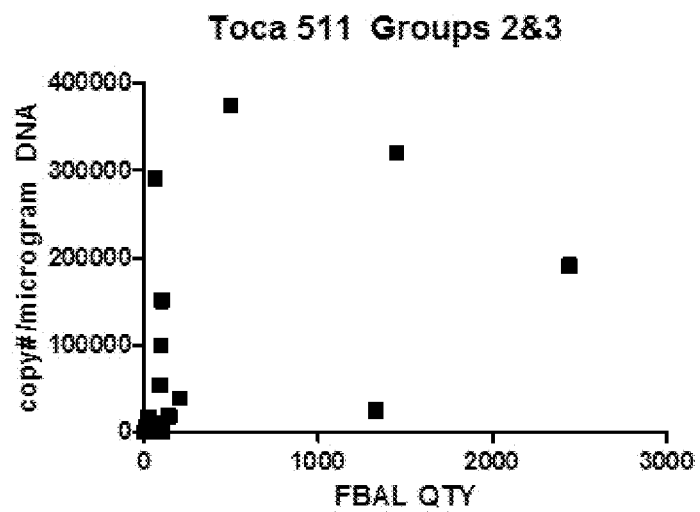
FIG. 19 shows show correlation of virus copy number and FBAL serum levels.

Results: Group 2 mice showed decreased tumor volume immediately following 5-FC treatment compared to Group 1 and 3 controls (FIG. 17). Group 2 mouse tumor volumes can be further broken down into two groups: responders and non-responders to 5-FC treatment that further are associated with increased virus genome copy number and high levels of FBAL detected in the serum (FIG. 18). For Groups 2 and 3 that received virus, statistically significant correlations (Spearman or Pearson analysis) were shown for virus copy number/genome and FBAL serum levels and for body weight and FBAL serum levels (FIG. 19).

The data demonstrate that blocking of IFANR-1 signaling facilitates infection and spread of vector in subcutaneous tumors. Multiple intratumoral injections of blocking IFNAR-1 antibody in combination with a single intratumoral injection of Toca 511 allows for therapeutic spread of virus when used in combination with 5-FC. Serum FBAL levels correlated with increased vector genome copy number.

Example 19: Anti-Tumor Efficacy Studies Examining IV Delivery of Vector in a Mouse Glioma Model The objective of this study is to determine if intravenous (IV) delivery of vector would home and spread in an intracranial tumor by assessing survival in a murine intracranial glioma model.

Female B6C3F1 mice (age ~8 weeks) underwent surgical placement of an indwelling guide cannula with a 3.0 mm projection implanted into the right striatum, and fitted with a cap containing a 3.5 mm projection. The stereotaxic coordinates are AP=+0.5 mm, ML=−1.8 mm (from bregma).

On Day 0, Tu2449 cells (1.2E4 cells in 1 μL) were implanted intracranially into all 4 groups of mice by infusion at 0.2 μL per minute (5 minutes, followed by a hold of 5 minutes) through an injection cannula with a 3.5 mm projection inserted through the guide cannula.

Starting on Day 3, Group 3 received IV (100 μL/day) injection of vector for 3 days (every other day) for a total vector dose of 1.95E8 TU/g of brain dose level; Group 4 received IV (100 μL/day) injection of vector for 5 continuous days for a total vector dose of 3.25E8 TU/g of brain dose level. Starting on Day 10, Groups 2-4 began cycles of 5-FC (500 mg/kg in 800 μL, IP, BID) for 4 consecutive days, followed by 10 days off drug; Group 1 received PBS as control (800 μL, IP, BID). Survival was assessed for at least 4 cycles.

Figure 20:
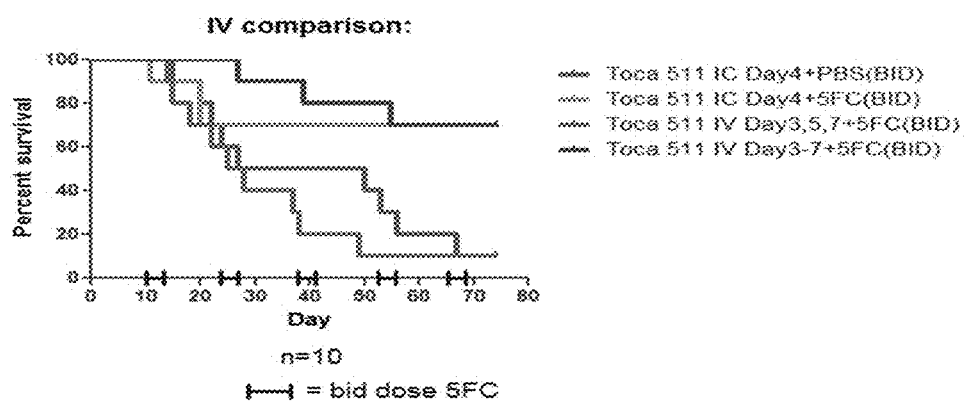
FIG. 20 shows a Kaplan-Meyer survival plot of mice receiving IC or IV delivery of vector followed by BID treatment of with 5-FC.

Survival analysis to Day 75 was performed on 10 mice each from Groups 1-4 and plotted as a Kaplan-Meyer plot (FIG. 20). Survival curves are compared by the log-rank test. P values of <0.05 are considered statistically significant in all analyses, which are performed with Prism 5 statistical software (GraphPad Software) or equivalent.

Results from treatment with the 5-day continuous IV vector administration+5-FC show a statistically significant survival advantage in this murine glioma model compared to treatment with vehicle, or 3-day IV vector administration+ 5-FC, while comparable to the IC vector+5-FC reference (p-value=0.8446). Multi-day IV dosing gives a more consistent viral uptake, spreading, and thus efficacy.

Example 20: Comparison of Vector Homing and Spread by Intracranial (IC) and Intravenous (IV) Delivery in Athymic Mouse Model The primary objective of this study is to compare vector homing and spread via IC and IV administration in athymic mouse model using both Tu2449 (mouse glioma cells) and U87 (human glioma cells) lines.

Female athymic mice (age ~8 weeks) underwent surgical placement of an indwelling guide cannula with a 3.0 mm projection implanted into the right striatum, and fitted with a cap containing a 3.5 mm projection. The stereotaxic coordinates are AP=+0.5 mm, ML=−1.8 mm (from bregma).

On Day 0, Tu2449 or U87-MG cells (2E4 cells in 1 μL) were implanted intracranially into all 4 groups of mice by infusion at 0.2 μL per minute (5 minutes, followed by a hold of 5 minutes) through an injection cannula with a 3.5 mm projection inserted through the guide cannula.

On Day 5, Groups 1 and 3 received IC (5 μL) injection of vector at 2.48E3 TU/g of brain dose level; Group 2 and 4 received IV (100 μL/day) injection of vector for 5 continuous days at a total dose of 1.24E8 TU/g of brain dose level.

Figure 21:
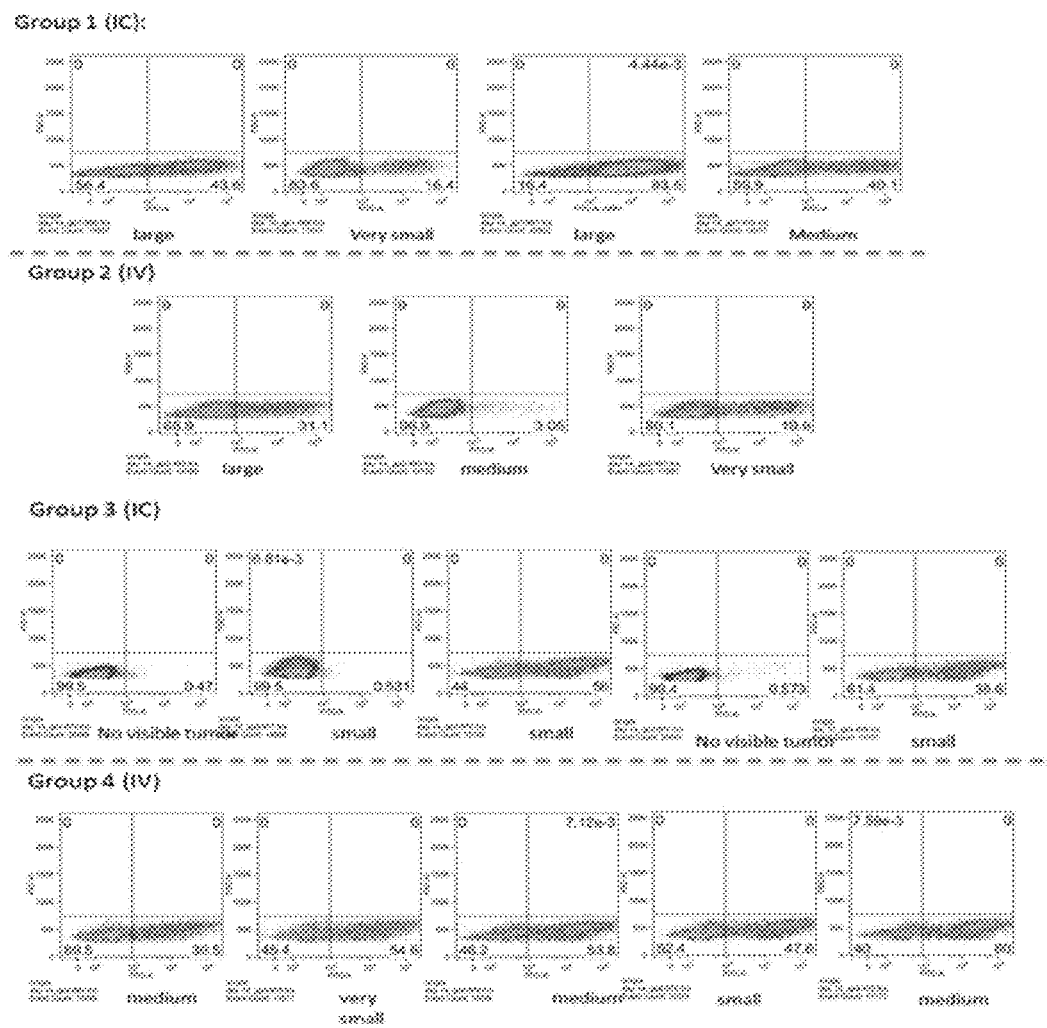
FIG. 21 shows FACS analysis of GFP positive cells (numbers represent percentage) of gated cells within the tumor for groups 1 and 2 on day 14 with Tu2449 cells and group 3 and 4 on day 14 with U87-cells.

Tumors were removed and analyzed by FLOW cytometry for the GFP positive cells from Groups 1-4 at Day 14. Flowjo software was used to analyze the data (FIG. 21).

Results show that using either Tu2449 or U87-UCLA cells as intracranial tumor implants in athymic mouse models, administration of vector via IV route successfully homed and infected the tumor cells at Day 14 after tumor implant as did the vector administered IC.

Example: 21

Screening of Agent that Modulate Vector Spread or Gene Therapy Using Oncoretroviral Vectors A wide range of agents that may affect a number of properties of the RRV, including agents that interact with the innate immune system, interferon production, viral transcription and integration were tested. One issue that makes such empirical testing necessary, apart from the general lack of information, is that although there maybe some initial reason for testing improved spread or therapeutic outcome, such as enhancement of some parts of the retroviral life cycle or inhibition of some pathway in innate immunity, it is completely unclear how that translates into a viral infection therapy with replicating retroviral vectors. It has been recognized that gamma retroviruses cannot productively infect non-replicating cells, and that the rate of cell replication has a profound effect on the efficiency of retroviral spread in that cell population. This is in contrast to other replicating viruses that have been proposed for anti-tumor therapy such as Vaccinia, Adenovirus, Vesicular Stomatitis virus, Measles, Parvoviruses and others known to those skilled in the art.

Table 5 shows a list of agents that we have tested in vitro either by interference with IFN induction in cultures of human plasmacytoid dendritic cells, neutralization of IFN action or inhibition/enhancement of vector spread, and notes where positive or negative effects have been observed ("Efficacy").

TABLE 5

In vitro testing of agents that may affect RVV efficacy in vivo.

| Drug | Targeted pathway | Target | Test system | Efficacy |
|---|---|---|---|---|
| BX795 | TLR | Ikkε | IFN production after in vitro stimulation of cultured human glioma cells | + |
| MS-275 | TLR | upstream of IRF3 | IFN production after in vitro stimulation of cultured human glioma cells | + |
| Bortezomib | TLR | S26 proteosome | IFN production after in vitro stimulation of cultured human plasmacytoid dendritic cells | + |
| B18R | IFNα/β | IFN IFN neutralization | IFN production after in vitro stimulation of cultured human glioma cells | + |
| Neu Ab αIFNα/βR2 | IFNα/β | IFNα/βR2 | Initial viral spread in cultured human glioma cells by flow cytometric analysis | + |
| CYT-387 | IFNα/β | JAK1/2 | Initial viral spread in cultured human glioma cells by flow cytometric analysis | − |
| Vse1 | IFNα/β | unidentified | Initial viral spread in cultured human glioma cells by flow cytometric analysis | − |
| CUDU-101 | IFNα/β | unidentified | Initial viral spread in cultured human glioma cells by flow cytometric analysis | − |
| Droxinostat | IFNα/β | unidentified | Initial viral spread in cultured human glioma cells by flow cytometric analysis | − |
| ITF2357 | IFNα/β | unidentified | Initial viral spread in cultured human glioma cells by flow cytometric analysis | − |
| MS-275 | IFNα/β | unidentified | Initial viral spread in cultured human glioma cells by flow cytometric analysis | − |
| imidazolo-oxinodole | PKR | PKR | Initial viral spread in cultured human glioma cells by flow cytometric analysis | − |
| Dexamethasone | Viral Transcription | Viral LTR | Initial viral spread in cultured human glioma cells by flow cytometric analysis | + |
| Mifepristone | Integration | Unidentified | Initial viral spread in cultured human glioma cells by flow cytometric analysis | + |

In addition, a number of agents were tested in the following various in vivo models: implanted subcutaneous tumors including EM6/CT26 mouse tumors in Balb/c mice and human U897 xenografts in nude mice; intracranial tumor models (usually syngeneic Tu2449 in B6C3F1 mice) or intracranial human U87 xenografts in nude mice. Usually initial testing was with GFP vectors (AC3-GFP aka T2.0006) first for spread then CD vectors (e.g., Toca 511) were tested for efficacy, if warranted.

Table 6 below summarizes some of the data gathered from the in vivo screening procedures.

TABLE 6

| Category | Mechanism | Outcome summary IC tumor model | Outcome summary SQ tumor model |
|---|---|---|---|
| Immune Modulator | | | |
| Suppressors to facilitate viral spread | | | |
| *General* | | | |
| Cyclosporine | Binds cyclophilin, inhibits T-cells | Not tested | No positive effect on vector spread |
| Dexamethasone (Depo Medrol for mice) | Suppresses prostaglandins, histamines, complement etc. | No Significant Survival improvement, with continuous administration. | Tumor growth slowed down. Performs best when given only during initial infection period |
| Bortezomib (Bortezomib) | Proteosome inhibitor | Significant Survival improvement out to day 42 | Not tested |
| *Specific innate blockers* | | | |
| Neoadjuvant interferon beta | Select for IFN resistance | Not tested | CT26 interferon resistant cell line implants: No positive effect on vector spread |
| Anti-IFN type 1 Receptor ab | Receptor blocking | Survival improvement | Significant improvement in vector spread. Therapeutic effect in combination with Toca 511 and 5-FC (toxicity due to high level of systemic 5-FU production). |
| VSE-1 | Inhibits IFN receptor signaling | Not tested | No positive effect on vector spread |
| Nuclear (eg. STAT, NF-kB, HDAC) | Transcription inhibition | In vitro HDAC screens showed MLV inhibition and/or cellular toxicity | |
| Mifepristone | Glucocorticoid receptor antagonist-facilitates gamma retroviral integration | In vitro data suggests benefit | In vitro data suggests benefit |
| Extracellular (eg. Anti-IFN ab or B18R) | Prevents Type I interferon binding to receptor | In vitro data suggests benefit | In vitro data suggests benefit |
| Rapamycin | mTor inhibitor | Not Tested | No significant positive effect on vector spread |
| Enhancers to induce anti-tumor immune response | | | |
| GMCSF | Activates macrophage | Not tested | Direct IT injection, No positive effect on vector spread; no inhibition of tumor growth |
| Thymosin alpha 1 | immunostimulant adjuvant | Two pilot studies showed significant increase in survival | Not tested |
| *General Facilitator* | | | |
| Polycation: chitosan, polybrene | Charge neutralization | Not tested | No positive effect on vector spread (polybrene) |
| Species matched packaging cell line | Reduce complement activation | Increases vector half life in blood four fold after iv administration in dogs | Increases vector half life in blood four fold after iv administration in dogs |
| *Mechanical* | | | |
| Large volume intravenous | | Positive Toca GFP delivery to U87/nude and Tu-2449 model 1x dose. Significant survival improvement Tu-2449 model after 5x Toca 511 i.v. dosing | Positive proof of concept delivery to tumor in combination with 5x dosing IFN blocking ab |
| Poloxamer 407 (Lutrol) | Biocomp, reverse thermal gel | Decrease in survival compared to Toca 511 control | Positive effect on spread early but not long term increase in vector spread |
| Hyaluronidase | Degrades connective tissue | Not tested | No significant positive effect on vector spread |
| Multiple direct injections | | Not tested | No significant positive effect on vector spread |
| Chondroitinase ABC | Degrades connective tissue | Not tested | No significant positive effect on vector spread |
| DMSO | Solvent/Delivery agent | Not tested | No significant positive effect on vector spread |

TABLE 6-continued

| Category | Mechanism | Outcome summary IC tumor model | Outcome summary SQ tumor model |
|---|---|---|---|
| GBM Combination In Clinical Use | | | |
| Avastin | AntiVEGF | Worse outcome compared to Toca 511 treatment alone | Not tested |
| Cyclophosphamide | Alkylating agent | Not tested | No significant positive effect on vector spread |
| Irinotecan | Topoisomerase inhibitor | No survival improvement | Not tested |
| Temozolomide | Alkylating agent | Worse outcome compared to Toca 511 treatment alone | Not tested |
| XRT | DNA damage | In vitro data suggests benefit | In vitro data suggests benefit |
| 5FU Combinations in Clinical Use | | | |
| Methotrexate | Antimetabolite | No significant survival improvement | Not tested |
| 5-FC continuous: IP injection 500 mg/kg | | 21 and 14 day cycles showed significant survival advantage, at early timepoints | Therapeutic effect in combination with IFN blocking ab (toxicity due to high level of systemic 5-FU production). |

From these experiments it can be seen that activity was observed with: BX795; MX275; Bortezomib; B18R vaccinia protein; anti-IFN Receptor antibody; dexamethasone; mifepristone; radiation; use of species matched producer cell line for vector production and administration; and iv administration. No benefit was observed, for example, with Vse-1, an agent for which a large benefit was seen in tumor models utilizing VSV as a antitumor agent (Diallo J-S. et al., Mol. Ther., 18: 1123-1129, 2010), emphasizing the difference between oncolytic viruses that replicate in dividing and non-dividing cells and the retroviral replicating viruses described in this disclosure.

Example 22: Anti-Tumor Efficacy Studies with the Combination of Bortezomib (Velcade®) and Vector in a Mouse Glioma Model The objective of this study is to determine if Bortezomib facilitate Toca 511 vector spread by assessing survival in a murine intracranial glioma model.

Female B6C3F1 mice (age ~8 weeks) underwent surgical placement of an indwelling guide cannula with a 3.0 mm projection implanted into the right striatum, and fitted with a cap containing a 3.5 mm projection. The stereotaxic coordinates are AP=+0.5 mm, ML=−1.8 mm (from bregma).

On Day 0, Tu2449 cells (1.4E4 cells in 1 μL) were implanted intracranially into all 4 groups of mice by infusion at 0.2 μL per minute (5 minutes, followed by a hold of 5 minutes) through an injection cannula with a 3.5 mm projection inserted through the guide cannula.

On Day 0 and every 7 days, Groups 3 and 4 received Bortezomib treatment (1 mg/kg; 25 μg/mouse) IP. On Day 4, Groups 1, 2 and 4 received IC (5 μL) vector of 6.3E4 TU/g of brain dose level and Group 3 received vehicle control. Starting on Day 10, Groups 2-4 began cycles of 5-FC (500 mg/kg in 800 μL, IP, BID) for 4 consecutive days, followed by 10 days off drug; Group 1 received PBS as control (800 μL, IP, BID). Survival was assessed for at least 4 cycles.

Figure 24:
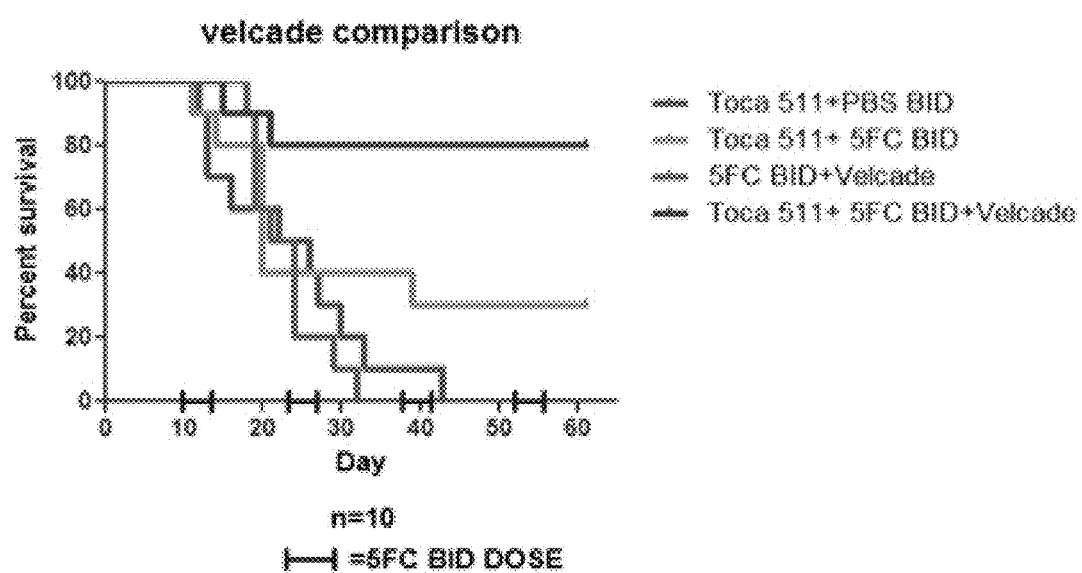
FIG. 24 shows a Kaplan-Meyer survival plot of mice receiving Velcade® therapy and Toca511 followed by BID treatment of with 5-FC.

Survival analysis to Day 60 was performed on 10 mice each from Groups 1-4 and plotted as a Kaplan-Meyer plot (FIG. 24). Survival curves are compared by the log-rank test. P values of <0.05 are considered statistically significant in all analyses, which are performed with Prism 5 statistical software (GraphPad Software) or equivalent.

Results from treatment with the combination of Bortezomib and vector show a statistically significant survival advantage in this murine glioma model compared to treatment with vector, vehicle, or Bortezomib alone.

What is claimed is:

1. A composition comprising:
a steroid or an inhibitor of a pattern recognition receptor (PRR) or an interferon (IFN) signaling pathway inhibitor, wherein the inhibitor of PRR is an antagonist of toll-like receptor-7 (TLR7) or TLR8 or an inhibitor of downstream TLR signaling, and wherein the IFN signaling pathway inhibitor is selected from the group consisting of an anti-IFN antibody, anti-IFN receptor antibody, and a combination thereof, and
wherein the composition further comprises a recombinant replication-competent gammaretrovirus or a viral vector encoding a replication-competent gammaretrovirus.

2. The composition of claim 1, wherein the replication-competent gammaretrovirus comprises:
a retroviral GAG protein;
a retroviral POL protein;
a retroviral envelope;
a retroviral RNA polynucleotide comprising a 3' untranslated region (U3) and repeat region (R) sequence at the 3' end of the retroviral polynucleotide sequence, an R and 5' untranslated region (U5) sequence at the 5' end of the retroviral polynucleotide, a gag nucleic acid domain, a pol nucleic acid domain and an env nucleic acid domain;
a cassette comprising an internal ribosome entry site (IRES) operably linked to a heterologous polynucleotide, wherein the cassette is positioned 5' to the U3 region and 3' to the env nucleic acid domain encoding the retroviral envelop; and
cis-acting sequences necessary for reverse transcription, packaging and integration in a target cell.

3. The composition of claim 2, wherein the retroviral RNA polynucleotide sequence is derived from murine leukemia virus (MLV), Moloney murine leukemia virus (MoMLV), Feline leukemia virus (FeLV) or Gibbon ape leukemia virus (GALV).

4. The composition of claim 3, wherein the MLV is an amphotropic MLV.

5. The composition of claim 1, wherein the viral vector comprises a sequence as set forth in SEQ ID NO: 1, 2, or 3.

6. The composition of claim 2, wherein the heterologous nucleic acid sequence encodes a biological response modifier.

7. The composition of claim 6, wherein the biological response modifier comprises an immunopotentiating cytokine.

8. The composition of claim 7, wherein the immunopotentiating cytokine is selected from the group consisting of interleukins 1 through 15, interferon, tumor necrosis factor (TNF), and granulocyte-macrophage-colony stimulating factor (GM-CSF).

9. The composition of claim 2, wherein the heterologous polynucleotide encodes a polypeptide that converts a nontoxic prodrug into a toxic drug.

10. The composition of claim 9, wherein the polypeptide that converts a nontoxic prodrug into a toxic drug is thymidine kinase, purine nucleoside phosphorylase (PNP), or cytosine deaminase.

11. The composition of claim 2, wherein the heterologous nucleic acid sequence encodes a targeting moiety.

12. The composition of claim 11, wherein the targeting moiety comprises a cancer antigen.

13. The composition of claim 2, wherein the heterologous polynucleotide sequence encodes a binding domain.

14. The composition of claim 13, wherein the binding domain comprises a receptor domain, an antibody, or antibody fragment.

15. The composition of claim 2, wherein the heterologous polynucleotide sequence comprises an inhibitory polynucleotide.

16. The composition of claim 15, wherein the inhibitory polynucleotide comprises an RNAi or siRNA sequence.

17. A composition comprising a member selected from the group consisting of:
  (i) an inhibitor of a pattern recognition receptor (PRR) or a interferon (IFN) signaling pathway inhibitor, wherein the inhibitor of PRR is an antagonist of toll-like receptor-7 (TLR7) or TLR8 or an inhibitor of downstream TLR signaling, and wherein the IFN signaling pathway inhibitor selected from the group consisting of an anti-IFN antibody, anti-IFN receptor antibody and a combination thereof;
  (ii) a steroid,
  (iii) an anti-progestin agent, and
  (iv) any combination of (i)-(iii),
in combination with a recombinant replicative gamma retrovirus comprising a heterologous polynucleotide, wherein the composition is for treating a cell proliferative disorder or disease.

18. A method of treating a cell proliferative disease or disorder comprising administering or contacting a subject in need of such treatment with a therapeutically effective amount of a composition of claim 17.

19. The method of claim 18, wherein the recombinant replicative gammaretrovirus comprises a polynucleotide that expressed a polypeptide having cytosine deaminase activity.

20. The method of claim 19, further comprising administering 5-fluorocytosine (5-FC) to the subject, wherein the 5-FC is converted to 5-fluorouracil (5-FU), and irradiating the subject.

21. The method of claim 18, wherein the steroid is selected from the group consisting of prednisone, prednisolone, fluticasone, dexamethasone, budesonide, or a salt thereof.

22. The method of claim 18, wherein the anti-progestin agent mifepristone.

23. The method of claim 19, further comprising measuring α-fluoro-β-alanine (FBAL) levels in a sample from the subject to determine therapeutic expression of cytosine deaminase activity.

24. The method of claim 23, wherein the sample is plasma or urine.

25. The method of claim 23, further comprising adjusting a therapeutic dose of 5-FC or the recombinant replication competent retrovirus.

26. The method of claim 18, wherein the recombinant retroviral vector is administered intravenously.

27. The method of claim 18, wherein the cell proliferative disorder is selected from the group consisting of lung cancer, colon-rectum cancer, breast cancer, prostate cancer, urinary tract cancer, uterine cancer, brain cancer, head and neck cancer, pancreatic cancer, melanoma, stomach cancer and ovarian cancer, rheumatoid arthritis or other autoimmune disease.

* * * * *

SEQUENCE LISTING

```
<160> NUMBER OF SEQ ID NOS: 4

<210> SEQ ID NO 1
<211> LENGTH: 11892
<212> TYPE: DNA
<213> ORGANISM: Artificial Sequence
<220> FEATURE:
<223> OTHER INFORMATION: pAC3-yCD2 recombinant vector

<400> SEQUENCE: 1
tagttattaa tagtaatcaa ttacggggtc attagttcat agcccatata tggagttccg     60
cgttacataa cttacggtaa atggcccgcc tggctgaccg cccaacgacc cccgcccatt    120
gacgtcaata atgacgtatg ttcccatagt aacgccaata gggactttcc attgacgtca    180
atgggtggag tatttacggt aaactgccca cttggcagta catcaagtgt atcatatgcc    240
aagtacgccc cctattgacg tcaatgacgg taaatggccc gcctggcatt atgcccagta    300
```

```
catgacctta tgggactttc ctacttggca gtacatctac gtattagtca tcgctattac      360
catggtgatg cggttttggc agtacatcaa tgggcgtgga tagcggtttg actcacgggg      420
atttccaagt ctccacccca ttgacgtcaa tgggagtttg ttttggcacc aaaatcaacg      480
ggactttcca aaatgtcgta acaactccgc cccattgacg caaatgggcg gtaggcgtgt      540
acggtgggag gtctatataa gcagagctgg tttagtgaac cggcgccagt cctccgattg      600
actgagtcgc ccgggtaccc gtgtatccaa taaaccctct tgcagttgca tccgacttgt      660
ggtctcgctg ttccttggga gggtctcctc tgagtgattg actacccgtc agcggggatc      720
tttcatttgg gggctcgtcc gggatcggga gaccctgcc cagggaccac cgacccacca      780
ccgggaggta agctggccag caacttatct gtgtctgtcc gattgtctag tgtctatgac      840
tgattttatg cgcctgcgtc ggtactagtt agctaactag ctctgtatct ggcggacccg      900
tggtggaact gacgagttcg gaacacccgg ccgcaaccct gggagacgtc ccagggactt      960
cgggggccgt ttttgtggcc cgacctgagt ccaaaaatcc cgatcgtttt ggactctttg     1020
gtgcaccccc cttagaggag ggatatgtgg ttctggtagg agacgagaac ctaaaacagt     1080
tcccgcctcc gtctgaattt ttgctttcgg tttgggaccg aagccgcgcc gcgcgtcttg     1140
tctgctgcag catcgttctg tgttgtctct gtctgactgt gtttctgtat ttgtctgaga     1200
atatgggcca gactgttacc actcccttaa gtttgacctt aggtcactgg aaagatgtcg     1260
agcggatcgc tcacaaccag tcggtagatg tcaagaagag acgttgggtt accttctgct     1320
ctgcagaatg ccaacctttt aacgtcggat ggccgcgaga cggcacccctt aaccgagacc     1380 tcatcaccca ggttaagatc aaggtctttt cacctggccc gcatggacac ccagaccagg     1440 tccctacat cgtgacctgg gaagccttgg cttttgaccc ccctccctgg gtcaagccct     1500
ttgtacaccc taagcctccg cctcctcttc ctccatccgc cccgtctctc cccttgaac     1560 ctcctcgttc gaccccgcct cgatcctccc tttatccagc cctcactcct tctctaggcg     1620
ccaaacctaa acctcaagtt ctttctgaca gtgggggggcc gctcatcgac ctacttacag     1680 aagaccccccc gccttatagg gacccaagac caccccttc cgacagggac ggaaatggtg     1740
gagaagcgac ccctgcggga gaggcaccgg accccctcccc aatggcatct cgcctacgtg     1800
ggagacggga gcccccttgtg gccgactcca ctacctcgca ggcattcccc ctccgcgcag     1860
gaggaaacgg acagcttcaa tactggccgt tctcctcttc tgacctttac aactggaaaa     1920
ataataaccc ttcttttttct gaagatccag gtaaactgac agctctgatc gagtctgttc     1980
tcatcaccca tcagcccacc tgggacgact gtcagcagct gttggggact ctgctgaccg     2040
gagaagaaaa acaacggggtg ctcttagagg ctagaaaggc ggtgcggggc gatgatgggc     2100
gccccactca actgcccaat gaagtcgatg ccgcttttcc cctcgagcgc ccagactggg     2160
attacaccac ccaggcaggt aggaaccacc tagtccacta tcgccagttg ctcctagcgg     2220
gtctccaaaa cgcgggcaga agccccacca atttggccaa ggtaaaagga ataacacaag     2280
ggcccaatga gtctccctcg gccttcctag agagacttaa ggaagcctat cgcaggtaca     2340
ctccttatga ccctgaggac ccagggcaag aaactaatgt gtctatgtct ttcatttggc     2400
agtctgcccc agacattggg agaaagttag agaggttaga gatttaaaa aacaagacgc     2460 ttggagattt ggttagagag gcagaaaaga tctttaataa acgagaaacc ccggaagaaa     2520
gagaggaacg tatcaggaga gaaacagagg aaaaagaaga acgccgtagg acagaggatg     2580
agcagaaaga gaaagaaaga gatcgtagga gacatagaga gatgagcaag ctattggcca     2640
```

```
ctgtcgttag tggacagaaa caggatagac agggaggaga acgaaggagg tcccaactcg    2700
atcgcgacca gtgtgcctac tgcaaagaaa aggggcactg ggctaaagat tgtcccaaga    2760
aaccacgagg acctcgggga ccaagacccc agacctccct cctgacccta gatgactagg    2820
gaggtcaggg tcaggagccc cccctgaacc caggataacc ctcaaagtc gggggcaac     2880 ccgtcacctt cctggtagat actggggccc aacactccgt gctgacccaa aatcctggac    2940
ccctaagtga taagtctgcc tgggtccaag ggctactgg aggaaagcgg tatcgctgga    3000
ccacggatcg caaagtacat ctagctaccg gtaaggtcac ccactctttc ctccatgtac    3060
cagactgtcc ctatcctctg ttaggaagag atttgctgac taaactaaaa gcccaaatcc    3120
actttgaggg atcaggagcc caggttatgg gaccaatggg gcagccctg caagtgttga    3180 ccctaaatat agaagatgag catcggctac atgagacctc aaaagagcca gatgtttctc    3240
tagggtccac atggctgtct gattttcctc aggcctgggc ggaaaccggg ggcatgggac    3300
tggcagttcg ccaagctcct ctgatcatac ctctgaaagc aacctctacc cccgtgtcca    3360
taaaacaata ccccatgtca caagaagcca gactggggat caagcccac atacagagac     3420 tgttggacca gggaatactg gtaccctgcc agtcccctg gaacacgccc ctgctacccg    3480
ttaagaaacc agggactaat gattataggc ctgtccagga tctgagagaa gtcaacaagc    3540
gggtggaaga catccacccc accgtgccca acccttacaa cctcttgagc gggctcccac    3600
cgtcccacca gtggtacact gtgcttgatt taaaggatgc cttttctgc ctgagactcc     3660 accccaccag tcagcctctc ttcgcctttg agtggagaga tccagagatg gaatctcag    3720 gacaattgac ctggaccaga ctcccacagg gtttcaaaaa cagtcccacc ctgtttgatg    3780
aggcactgca cagagaccta gcagacttcc ggatccagca cccagacttg atcctgctac    3840
agtacgtgga tgacttactg ctggccgcca cttctgagct agactgccaa caaggtactc    3900
gggccctgtt acaaacccta gggaacctcg ggtatcgggc ctcggccaag aaagcccaaa    3960
tttgccagaa acaggtcaag tatctggggt atcttctaaa agagggtcag agatggctga    4020
ctgaggccag aaaagagact gtgatggggc agcctactcc gaagacccct cgacaactaa    4080
gggagttcct agggacggca ggcttctgtc gcctctggat ccctgggttt gcagaaatgg    4140
cagccccctt gtaccctctc accaaaacgg ggactctgtt taattggggc ccagaccaac    4200
aaaaggccta tcaagaaatc aagcaagctc ttctaactgc cccagccctg ggttgccag     4260 atttgactaa gcccttgaa ctctttgtcg acgagaagca gggctacgcc aaaggtgtcc     4320
taacgcaaaa actgggacct tggcgtcggc cggtggccta cctgtccaaa agctagacc     4380 cagtagcagc tgggtggccc ccttgcctac ggatggtagc agccattgcc gtactgacaa    4440
aggatgcagg caagctaacc atgggacagc cactagtcat tctggccccc catgcagtag    4500
aggcactagt caaacaaccc cccgaccgct ggctttccaa cgcccggatg actcactatc    4560
aggccttgct tttggacacg gaccgggtcc agttcggacc ggtggtagcc ctgaacccgg    4620
ctacgctgct cccactgcct gaggaagggc tgcaacacaa ctgccttgat atcctggccg    4680
aagcccacgg aaccccgaccc gacctaacgg accagccgct cccagacgcc gaccacacct    4740
ggtacacgga tggaagcagt ctcttacaag agggacagcg taaggcggga gctgcggtga    4800
ccaccgagac cgaggtaatc tgggctaaag ccctgccagc cgggacatcc gctcagcggg    4860
ctgaactgat agcactcacc caggcccaa agatggcaga aggtaagaag ctaaatgttt     4920
atactgatag ccgttatgct tttgctactg cccatatcca tggagaaata tacagaaggc    4980
gtgggttgct cacatcagaa ggcaaagaga tcaaaaataa agacgagatc ttggcccctac    5040
```

```
taaaagccct ctttctgccc aaaagactta gcataatcca ttgtccagga catcaaaagg    5100
gacacagcgc cgaggctaga ggcaaccgga tggctgacca agcggcccga aaggcagcca    5160
tcacagagac tccagacacc tctaccctcc tcatagaaaa ttcatcaccc tacacctcag    5220
aacattttca ttacacagtg actgatataa aggacctaac caagttgggg gccatttatg    5280
ataaaacaaa gaagtattgg gtctaccaag gaaaacctgt gatgcctgac cagtttactt    5340
ttgaattatt agactttctt catcagctga ctcacctcag cttctcaaaa atgaaggctc    5400
tcctagagag aagccacagt ccctactaca tgctgaaccg ggatcgaaca ctcaaaaata    5460
tcactgagac ctgcaaagct tgtgcacaag tcaacgccag caagtctgcc gttaaacagg    5520
gaactagggt ccgcgggcat cggcccggca ctcattggga gatcgatttc accgagataa    5580
agcccggatt gtatggctat aaatatcttc tagtttttat agatacccttt tctggctgga   5640 tagaagcctt cccaaccaag aaagaaaccg ccaaggtcgt aaccaagaag ctactagagg    5700
agatcttccc caggttcggc atgcctcagg tattgggaac tgacaatggg cctgccttcg    5760
tctccaaggt gagtcagaca gtggccgatc tgttggggat tgattggaaa ttacattgtg    5820
catacagacc ccaaagctca ggccaggtag aaagaatgaa tagaaccatc aaggagactt    5880
taactaaatt aacgcttgca actggctcta gagactgggt gctcctactc cccttagccc    5940
tgtaccgagc ccgcaacacg ccgggccccc atggcctcac cccatatgag atcttatatg    6000
gggcaccccc gccccttgta aacttccctg accctgacat gacaagagtt actaacagcc    6060
cctctctcca agctcactta caggctctct acttagtcca gcacgaagtc tggagacctc    6120
tggcggcagc ctaccaagaa caactggacc gaccggtggt acctcaccct taccgagtcg    6180
gcgacacagt gtgggtccgc cgacaccaga ctaagaacct agaacctcgc tggaaaggac    6240
cttacacagt cctgctgacc accccaccg ccctcaaagt agacggcatc gcagcttgga    6300
tacacgccgc ccacgtgaag gctgccgacc ccggggtgg accatcctct agactgacat    6360
ggcgcgttca acgctctcaa aaccccctca agataagatt aacccgtgga agcccttaat    6420
agtcatggga gtcctgttag gagtagggat ggcagagagc ccccatcagg tctttaatgt    6480
aacctggaga gtcaccaacc tgatgactgg gcgtaccgcc aatgccacct ccctcctggg    6540
aactgtacaa gatgccttcc caaaattata ttttgatcta tgtgatctgg tcggagagga    6600 gtgggacccct tcagaccagg aaccgtatgt cgggtatggc tgcaagtacc ccgcagggag    6660
acagcggacc cggacttttg acttttacgt gtgccctggg cataccgtaa agtcggggtg    6720
tgggggacca ggagagggct actgtggtaa atggggggtgt gaaaccaccg acaggcttca    6780
ctggaagccc acatcatcgt gggacctaat ctcccttaag cgcggtaaca ccccctggga    6840
cacgggatgc tctaaagttg cctgtggccc ctgctacgac ctctccaaag tatccaattc    6900
cttccaaggg gctactcgag ggggcagatg caaccctcta gtcctagaat tcactgatgc    6960
aggaaaaaag gctaactggg acgggcccaa atcgtgggga ctgagactgt accggacagg    7020
aacagatcct attaccatgt tctccctgac ccggcaggtc cttaatgtgg accccgagt    7080 ccccataggg cccaacccag tattacccga ccaaagactc ccttcctcac caatagagat    7140
tgtaccggct ccacagccac ctagccccct caataccagt tacccccctt ccactaccag    7200
tacaccctca acctcccta caagtccaag tgtcccacag ccaccccag gaactggaga    7260 tagactacta gctctagtca aaggagccta tcaggcgctt aacctcacca atccgacaa    7320 gacccaagaa tgttggctgt gcttagtgtc gggacctcct tattacgaag gagtagcggt    7380
```

```
cgtgggcact tataccaatc attccaccgc tccggccaac tgtacggcca cttcccaaca   7440
taagcttacc ctatctgaag tgacaggaca gggcctatgc atgggggcag tacctaaaac   7500
tcaccaggcc ttatgtaaca ccacccaaag cgccggctca ggatcctact accttgcagc   7560
acccgccgga acaatgtggg cttgcagcac tggattgact ccctgcttgt ccaccacggt   7620
gctcaatcta accacagatt attgtgtatt agttgaactc tggcccagag taatttacca   7680
ctcccccgat tatatgtatg gtcagcttga acagcgtacc aaatataaaa gagagccagt   7740
atcattgacc ctggcccttc tactaggagg attaaccatg ggagggattg cagctggaat   7800
agggacgggg accactgcct taattaaaac ccagcagttt gagcagcttc atgccgctat   7860
ccagacagac ctcaacgaag tcgaaaagtc aattaccaac ctagaaaagt cactgacctc   7920
gttgtctgaa gtagtcctac agaaccgcag aggcctagat ttgctattcc taaaggaggg   7980
aggtctctgc gcagccctaa agaagaatg ttgtttttat gcagaccaca cggggctagt   8040
gagagacagc atggccaaat taagagaaag gcttaatcag agacaaaaac tatttgagac   8100
aggccaagga tggttcgaag ggctgtttaa tagatccccc tggtttacca ccttaatctc   8160
caccatcatg ggacctctaa tagtactctt actgatctta ctctttggac cttgcattct   8220
caatcgattg gtccaattg ttaaagacag gatctcagtg gtccaggctc tggttttgac   8280
tcagcaatat caccagctaa aacccataga gtacgagcca tgaacgcgtt actggccgaa   8340
gccgcttgga ataaggccgg tgtgcgtttg tctatatgtt attttccacc atattgccgt   8400
cttttggcaa tgtgagggcc cggaaacctg gccctgtctt cttgacgagc attcctaggg   8460
gtctttcccc tctcgccaaa ggaatgcaag gtctgttgaa tgtcgtgaag gaagcagttc   8520
ctctggaagc ttcttgaaga caaacaacgt ctgtagcgac cctttgcagg cagcggaacc   8580
ccccacctgg cgacaggtgc ctctgcggcc aaaagccacg tgtataagat acacctgcaa   8640
aggcggcaca accccagtgc cacgttgtga gttggatagt tgtggaaaga gtcaaatggc   8700
tctcctcaag cgtattcaac aaggggctga aggatgccca aaggtaccc cattgtatgg   8760
gatctgatct ggggcctcgg tgcacatgct ttacatgtgt ttagtcgagg ttaaaaaaac   8820
gtctaggccc cccgaaccac ggggacgtgg ttttccttg aaaaacacga ttataaatgg   8880
tgaccggcgg catggcctcc aagtgggatc aaaagggcat ggatatcgct tacgaggagg   8940
ccctgctggg ctacaaggag ggcggcgtgc ctatcggcgg ctgtctgatc aacaacaagg   9000
acggcagtgt gctgggcagg ggccacaaca tgaggttcca gaagggctcc gccaccctgc   9060
acggcgagat ctccaccctg agaactgtg cagctggt gggcaaggtg tacaaggaca   9120
ccaccctgta caccaccctg tcccttgtg acatgtgtac cggcgctatc atcatgtacg   9180
gcatccctag gtgtgtgatc ggcgagaacg tgaacttcaa gtccaagggc gagaagtacc   9240
tgcaaaccag gggccacgag gtggtggttg ttgacgatga gaggtgtaag aagctgatga   9300
agcagttcat cgacgagagg cctcaggact ggttcgagga tatcggcgag taagcggccg   9360
cagataaaat aaaagatttt atttagtctc cagaaaaagg ggggaatgaa agaccccacc   9420
tgtaggtttg gcaagctagc ttaagtaacg ccattttgca aggcatggaa aaatacataa   9480
ctgagaatag agaagttcag atcaaggtca ggaacagatg aacagctga atatgggcca   9540
aacaggatat ctgtggtaag cagttcctgc cccggctcag ggccaagaac agatggaaca   9600
gctgaatatg gccaaacag gatatctgtg gtaagcagtt cctgccccgg ctcagggcca   9660
agaacagatg gtccccagat gcggtccagc cctcagcagt ttctagagaa ccatcagatg   9720
tttccagggt gccccaagga cctgaaatga ccctgtgcct tatttgaact aaccaatcag   9780
```

```
ttcgcttctc gcttctgttc gcgcgcttct gctccccgag ctcaataaaa gagcccacaa    9840
cccctcactc ggggcgccag tcctccgatt gactgagtcg cccgggtacc cgtgtatcca    9900
ataaaccctc ttgcagttgc atccgacttg tggtctcgct gttccttggg agggtctcct    9960
ctgagtgatt gactacccgt cagcggggggt ctttcattac atgtgagcaa aaggccagca  10020
aaaggccagg aaccgtaaaa aggccgcgtt gctggcgttt ttccataggc tccgcccccc   10080
tgacgagcat cacaaaaatc gacgctcaag tcagaggtgg cgaaacccga caggactata   10140
aagataccag gcgtttcccc ctggaagctc cctcgtgcgc tctcctgttc cgaccctgcc   10200
gcttaccgga tacctgtccg cctttctccc ttcgggaagc gtggcgcttt ctcaatgctc   10260
acgctgtagg tatctcagtt cggtgtaggt cgttcgctcc aagctgggct gtgtgcacga   10320
accccccgtt cagcccgacc gctgcgcctt atccggtaac tatcgtcttg agtccaaccc   10380
ggtaagacac gacttatcgc cactggcagc agccactggt aacaggatta gcagagcgag   10440
gtatgtaggc ggtgctacag agttcttgaa gtggtggcct aactacggct acactagaag   10500
gacagtattt ggtatctgcg ctctgctgaa gccagttacc ttcggaaaaa gagttggtag   10560
ctcttgatcc ggcaaacaaa ccaccgctgg tagcggtggt ttttttgttt gcaagcagca   10620
gattacgcgc agaaaaaaag gatctcaaga agatcctttg atcttttcta cggggtctga   10680
cgctcagtgg aacgaaaact cacgttaagg gattttggtc atgagattat caaaaaggat   10740
cttcacctag atccttttaa attaaaaatg aagttttaaa tcaatctaaa gtatatatga   10800
gtaaacttgg tctgacagtt accaatgctt aatcagtgag gcacctatct cagcgatctg   10860
tctatttcgt tcatccatag ttgcctgact ccccgtcgtg tagataacta cgatacggga   10920
gggcttacca tctggcccca gtgctgcaat gataccgcga gacccacgct caccggctcc   10980
agatttatca gcaataaacc agccagccgg aagggccgag cgcagaagtg gtcctgcaac   11040
tttatccgcc tccatccagt ctattaattg ttgccgggaa gctagagtaa gtagttcgcc   11100
agttaatagt ttgcgcaacg ttgttgccat tgctgcaggc atcgtggtgt cacgctcgtc   11160
gtttggtatg gcttcattca gctccggttc ccaacgatca aggcgagtta catgatcccc   11220
catgttgtgc aaaaaagcgg ttagctcctt cggtcctccg atcgttgtca gaagtaagtt   11280
ggccgcagtg ttatcactca tggttatggc agcactgcat aattctctta ctgtcatgcc   11340
atccgtaaga tgcttttctg tgactggtga gtactcaacc aagtcattct gagaatagtg   11400
tatgcggcga ccgagttgct cttgcccggc gtcaacacgg gataataccg cgccacatag   11460
cagaacttta aaagtgctca tcattggaaa acgttcttcg gggcgaaaac tctcaaggat   11520
cttaccgctg ttgagatcca gttcgatgta acccactcgt gcacccaact gatcttcagc   11580
atcttttact ttcaccagcg tttctgggtg agcaaaaaca ggaaggcaaa atgccgcaaa   11640
aaagggaata agggcgacac ggaaatgttg aatactcata ctcttccttt ttcaatatta   11700
ttgaagcatt tatcagggtt attgtctcat gagcggatac atatttgaat gtatttagaa   11760
aaataaacaa ataggggttc cgcgcacatt tccccgaaaa gtgccacctg acgtctaaga   11820
aaccattatt atcatgacat taacctataa aaataggcgt atcacgaggc cctttcgtct   11880
tcaagaattc at                                                       11892
```

<210> SEQ ID NO 2
<211> LENGTH: 11892
<212> TYPE: DNA
<213> ORGANISM: Artificial Sequence
<220> FEATURE:

<223> OTHER INFORMATION: pAC3-yCD recombinant vector

<400> SEQUENCE: 2

```
tagttattaa tagtaatcaa ttacggggtc attagttcat agcccatata tggagttccg      60
cgttacataa cttacggtaa atggcccgcc tggctgaccg cccaacgacc cccgcccatt     120
gacgtcaata atgacgtatg ttcccatagt aacgccaata gggactttcc attgacgtca     180
atgggtggag tatttacggt aaactgccca cttggcagta catcaagtgt atcatatgcc     240
aagtacgccc cctattgacg tcaatgacgg taaatggccc gcctggcatt atgcccagta     300
catgacctta tgggactttc ctacttggca gtacatctac gtattagtca tcgctattac     360
catggtgatg cggttttggc agtacatcaa tgggcgtgga tagcggtttg actcacgggg     420
atttccaagt ctccacccca ttgacgtcaa tgggagtttg ttttggcacc aaaatcaacg     480
ggactttcca aaatgtcgta caactccgc cccattgacg caaatgggcg gtaggcgtgt     540
acggtgggag gtctatataa gcagagctgg tttagtgaac cggcgccagt cctccgattg     600
actgagtcgc ccgggtaccc gtgtatccaa taaaccctct tgcagttgca tccgacttgt     660
ggtctcgctg ttccttggga gggtctcctc tgagtgattg actacccgtc agcgggggtc     720
tttcatttgg gggctcgtcc gggatcggga gacccctgcc cagggaccac cgacccacca     780
ccggaggta agctggccag caacttatct gtgtctgtcc gattgtctag tgtctatgac     840
tgattttatg cgcctgcgtc ggtactagtt agctaactag ctctgtatct ggcggacccg     900
tggtggaact gacgagttcg gaacacccgg ccgcaaccct gggagacgtc cagggactt      960
cgggggccgt ttttgtggcc cgacctgagt ccaaaaatcc cgatcgtttt ggactctttg    1020
gtgcacccc cttagaggag ggatatgtgg ttctggtagg agacgagaac ctaaaacagt    1080
tcccgcctcc gtctgaattt ttgctttcgg tttgggaccg aagccgcgcc gcgcgtcttg    1140
tctgctgcag catcgttctg tgttgtctct gtctgactgt gtttctgtat tgtctgaga     1200
atatgggcca gactgttacc actcccttaa gtttgacctt aggtcactgg aaagatgtcg    1260
agcggatcgc tcacaaccag tcggtagatg tcaagaagag cgttgggtt accttctgct    1320
ctgcagaatg ccaaccttt aacgtcggat ggccgcgaga cggcacctt aaccgagacc     1380
tcatcaccca ggttaagatc aaggtctttt cacctggccc gcatggacac ccagaccagg    1440
tccctacat cgtgacctgg gaagcttgg cttttgaccc cctccctgg gtcaagccct      1500
ttgtacaccc taagcctccg cctcctcttc ctccatccgc cccgtctctc cccttgaac     1560
ctcctcgttc gacccccgcct cgatcctccc tttatccagc cctcactcct tctctaggcg    1620
ccaaacctaa acctcaagtt ctttctgaca gtgggggggcc gctcatcgac ctacttacag    1680
aagacccccc gccttatagg gacccaagac caccccttc cgacagggac ggaaatggtg    1740
gagaagcgac ccctgcggga gaggcaccgg acccctcccc aatggcatct cgcctacgtg    1800
ggagacggga gccccctgtg gccgactcca ctacctcgca ggcattcccc ctccgcgcag    1860
gaggaaacgg acagcttcaa tactggccgt tctcctcttc tgacctttac aactggaaaa    1920
ataataaccc ttctttttct gaagatccag gtaaactgac agctctgatc gagtctgttc    1980
tcatcaccca tcagcccacc tgggacgact gtcagcagct gttggggact ctgctgaccg    2040
gagaagaaaa acaacgggtg ctcttagagg ctagaaaggc ggtgcggggc gatgatgggc    2100
gccccactca actgcccaat gaagtcgatg ccgcttttcc cctcgagcgc ccagactggg    2160
attacaccac ccaggcaggt aggaaccacc tagtccacta tcgccagttg ctcctagcgg    2220
gtctccaaaa cgcgggcaga agccccacca atttggccaa ggtaaaagga ataacacaag    2280
```

```
ggcccaatga gtctccctcg gccttcctag agagacttaa ggaagcctat cgcaggtaca    2340
ctccttatga ccctgaggac ccagggcaag aaactaatgt gtctatgtct ttcatttggc    2400
agtctgcccc agacattggg agaaagttag agaggttaga agatttaaaa aacaagacgc    2460
ttggagattt ggttagagag gcagaaaaga tctttaataa acgagaaacc ccggaagaaa    2520
gagaggaacg tatcaggaga gaaacagagg aaaagaaga acgccgtagg acagaggatg    2580
agcagaaaga gaaagaaaga gatcgtagga gacatagaga gatgagcaag ctattggcca    2640
ctgtcgttag tggacagaaa caggatagac agggaggaga acgaaggagg tcccaactcg    2700
atcgcgacca gtgtgcctac tgcaaagaaa aggggcactg ggctaaagat tgtcccaaga    2760
aaccacgagg acctcgggga ccaagacccc agacctccct cctgacccta gatgactagg    2820
gaggtcaggg tcaggagccc cccctgaacc caggataac cctcaaagtc gggggcaac    2880 ccgtcacctt cctggtagat actggggccc aacactccgt gctgacccaa aatcctggac    2940
ccctaagtga taagtctgcc tgggtccaag gggctactgg aggaaagcgg tatcgctgga    3000
ccacggatcg caaagtacat ctagctaccg gtaaggtcac ccactctttc ctccatgtac    3060
cagactgtcc ctatcctctg ttaggaagag atttgctgac taaactaaaa gcccaaatcc    3120
actttgaggg atcaggagcc caggttatgg gaccaatggg gcagcccctg caagtgttga    3180
ccctaaatat agaagatgag catcggctac atgagacctc aaaagagcca gatgtttctc    3240
tagggtccac atggctgtct gattttcctc aggcctgggc ggaaaccggg ggcatgggac    3300
tggcagttcg ccaagctcct ctgatcatac ctctgaaagc aacctctacc ccgtgtcca    3360 taaaacaata ccccatgtca caagaagcca gactggggat caagcccac atacagagac    3420 tgttggacca gggaatactg gtaccctgcc agtcccctg gaacacgccc ctgctacccg    3480
ttaagaaacc agggactaat gattataggc ctgtccagga tctgagagaa gtcaacaagc    3540
gggtggaaga catccacccc accgtgccca acccttacaa cctcttgagc gggctcccac    3600
cgtcccacca gtggtacact gtgcttgatt taaaggatgc cttttttctgc ctgagactcc    3660 accccaccag tcagcctctc ttcgcctttg agtggagaga tccagagatg ggaatctcag    3720
gacaattgac ctggaccaga ctcccacagg gtttcaaaaa cagtcccacc ctgtttgatg    3780
aggcactgca cagagaccta gcagacttcc ggatccagca cccagacttg atcctgctac    3840
agtacgtgga tgacttactg ctggccgcca cttctgagct agactgccaa caaggtactc    3900
gggccctgtt acaaacccta gggaacctcg ggtatcgggc ctcggccaag aaagcccaaa    3960
tttgccagaa acaggtcaag tatctggggt atcttctaaa agagggtcag agatggctga    4020
ctgaggccag aaaagagact gtgatggggc agcctactcc gaagacccct cgacaactaa    4080
gggagttcct agggacggca ggcttctgtc gcctctggat ccctgggttt gcagaaatgg    4140
cagccccctt gtaccctctc accaaaacgg ggactctgtt taattggggc ccagaccaac    4200
aaaaggccta tcaagaaatc aagcaagctc ttctaactgc cccagcctg ggttgccag    4260 atttgactaa gcccttgaa ctctttgtcg acgagaagca gggctacgcc aaaggtgtcc    4320
taacgcaaaa actgggacct tggcgtcggc cggtggccta cctgtccaaa aagctagacc    4380
cagtagcagc tgggtggccc ccttgcctac ggatggtagc agccattgcc gtactgacaa    4440
aggatgcagg caagctaacc atgggacagc cactagtcat tctggcccc catgcagtag    4500 aggcactagt caaacaaccc cccgaccgct ggctttccaa cgcccggatg actcactatc    4560
aggccttgct tttggacacg gaccgggtcc agttcggacc ggtggtagcc ctgaacccgg    4620
```

```
ctacgctgct cccactgcct gaggaagggc tgcaacacaa ctgccttgat atcctggccg    4680
aagcccacgg aacccgaccc gacctaacgg accagccgct cccagacgcc gaccacacct    4740
ggtacacgga tggaagcagt ctcttacaag agggacagcg taaggcggga gctgcggtga    4800
ccaccgagac cgaggtaatc tgggctaaag ccctgccagc cgggacatcc gctcagcggg    4860
ctgaactgat agcactcacc caggccctaa agatggcaga aggtaagaag ctaaatgttt    4920
atactgatag ccgttatgct tttgctactg cccatatcca tggagaaata tacagaaggc    4980
gtgggttgct cacatcagaa ggcaaagaga tcaaaaataa agacgagatc ttggccctac    5040
taaaagccct ctttctgccc aaaagactta gcataatcca ttgtccagga catcaaaagg    5100
gacacagcgc cgaggctaga ggcaaccgga tggctgacca agcggcccga aaggcagcca    5160
tcacagagac tccagacacc tctaccctcc tcatagaaaa ttcatcaccc tacacctcag    5220
aacattttca ttacacagtg actgatataa aggacctaac caagttgggg gccatttatg    5280
ataaaacaaa gaagtattgg gtctaccaag gaaaacctgt gatgcctgac cagtttactt    5340
ttgaattatt agactttctt catcagctga ctcacctcag cttctcaaaa atgaaggctc    5400
tcctagagag aagccacagt ccctactaca tgctgaaccg ggatcgaaca ctcaaaaata    5460
tcactgagac ctgcaaagct tgtgcacaag tcaacgccag caagtctgcc gttaaacagg    5520
gaactagggt ccgcgggcat cggcccggcc tcattgggga gatcgatttc accgagataa    5580
agcccggatt gtatgctat aaatatcttc tagtttttat agataccttt tctggctgga    5640
tagaagcctt cccaaccaag aaagaaaccg ccaaggtcgt aaccaagaag ctactagagg    5700
agatcttccc caggttcggc atgcctcagg tattgggaac tgacaatggg cctgccttcg    5760
tctccaaggt gagtcagaca gtggccgatc tgttggggat tgattggaaa ttacattgtg    5820
catacagacc ccaaagctca ggccaggtag aaagaatgaa tagaaccatc aaggagactt    5880
taactaaatt aacgcttgca actggctcta gagactgggt gctcctactc cccttagccc    5940
tgtaccgagc ccgcaacacg ccgggccccc atggcctcac cccatatgag atcttatatg    6000
gggcaccccc gccccttgta aacttccctg accctgacat gacaagagtt actaacagcc    6060
cctctctcca agctcactta caggctctct acttagtcca gcacgaagtc tggagacctc    6120
tggcggcagc ctaccaagaa caactggacc gaccggtggt acctcaccct taccgagtcg    6180
gcgacacagt gtgggtccgc cgacaccaga ctaagaacct agaacctcgc tggaaaggac    6240
cttacacagt cctgctgacc accccccaccg ccctcaaagt agacggcatc gcagcttgga    6300
tacacgccgc ccacgtgaag gctgccgacc ccggggtgg accatcctct agactgacat    6360
ggcgcgttca acgctctcaa aacccctca agataagatt aacccgtgga agcccttaat    6420
agtcatggga gtcctgttag gagtagggat ggcagagagc ccccatcagg tctttaatgt    6480
aacctggaga gtcaccaacc tgatgactgg gcgtaccgcc aatgccacct ccctcctggg    6540
aactgtacaa gatgccttcc caaaattata ttttgatcta tgtgatctgg tcggagagga    6600
gtgggaccct tcagaccagg aaccgtatgt cgggtatggc tgcaagtacc ccgcagggag    6660
acagcggacc cggactttg acttttacgt gtgccctggg cataccgtaa agtcggggtg    6720
tgggggacca ggagagggct actgtggtaa atggggtgt gaaaccaccg acaggcttta    6780
ctggaagccc acatcatcgt gggacctaat ctcccttaag cgcggtaaca ccccctggga    6840
cacgggatgc tctaaagttg cctgtggccc ctgctacgac ctctccaaag tatccaattc    6900
cttccaaggg gctactcgag ggggcagatg caacccctcta gtcctagaat tcactgatgc    6960
aggaaaaaag gctaactggg acgggcccaa atcgtgggga ctgagactgt accggacagg    7020
```

```
aacagatcct attaccatgt tctccctgac ccggcaggtc cttaatgtgg gacccccgagt    7080 ccccataggg cccaacccag tattacccga ccaaagactc ccttcctcac caatagagat    7140
tgtaccggct ccacagccac ctagccccct caataccagt tacccccctt ccactaccag    7200
tacaccctca acctccccta caagtccaag tgtcccacag ccaccccag gaactggaga     7260 tagactacta gctctagtca aaggagccta tcaggcgctt aacctcacca atcccgacaa    7320
gacccaagaa tgttggctgt gcttagtgtc gggacctcct tattacgaag gagtagcggt    7380
cgtgggcact tataccaatc attccaccgc tccggccaac tgtacggcca cttcccaaca    7440
taagcttacc ctatctgaag tgacaggaca gggcctatgc atggggggcag tacctaaaac   7500 tcaccaggcc ttatgtaaca ccacccaaag cgccggctca ggatcctact accttgcagc    7560
acccgccgga acaatgtggg cttgcagcac tggattgact ccctgcttgt ccaccacggt    7620
gctcaatcta accacagatt attgtgtatt agttgaactc tggcccagag taatttacca    7680
ctcccccgat tatatgtatg gtcagcttga acagcgtacc aaatataaaa gagagccagt    7740
atcattgacc ctggcccttc tactaggagg attaaccatg ggagggattg cagctggaat    7800
agggacgggg accactgcct taattaaaac ccagcagttt gagcagcttc atgccgctat    7860
ccagacagac ctcaacgaag tcgaaaagtc aattaccaac ctagaaaagt cactgaccctc   7920 gttgtctgaa gtagtcctac agaaccgcag aggcctagat ttgctattcc taaaggaggg    7980
aggtctctgc gcagccctaa aagaagaatg ttgtttttat gcagaccaca cggggctagt    8040
gagagacagc atggccaaat taagagaaag gcttaatcag agacaaaaac tatttgagac    8100
aggccaagga tggttcgaag ggctgtttaa tagatccccc tggtttacca ccttaatctc    8160
caccatcatg ggacctctaa tagtactctt actgatctta ctctttggac cttgcattct    8220
caatcgattg gtccaatttg ttaaagacag gatctcagtg gtccaggctc tggttttgac    8280
tcagcaatat caccagctaa acccataga gtacgagcca tgaacgcgtt actggccgaa    8340
gccgcttgga ataaggccgg tgtgcgtttg tctatatgtt attttccacc atattgccgt    8400
cttttggcaa tgtgagggcc cggaaacctg gccctgtctt cttgacgagc attcctaggg    8460
gtctttcccc tctcgccaaa ggaatgcaag gtctgttgaa tgtcgtgaag gaagcagttc    8520
ctctggaagc ttcttgaaga caaacaacgt ctgtagcgac cctttgcagg cagcggaacc    8580
ccccacctgg cgacaggtgc ctctgcggcc aaaagccacg tgtataagat acacctgcaa    8640
aggcggcaca accccagtgc cacgttgtga gttggatagt tgtggaaaga gtcaaatggc    8700
tctcctcaag cgtattcaac aaggggctga aggatgccca gaaggtaccc cattgtatgg    8760
gatctgatct ggggcctcgg tgcacatgct ttacatgtgt ttagtcgagg ttaaaaaaac    8820
gtctaggccc cccgaaccac ggggacgtgg ttttcctttg aaaaacacga ttataaatgg    8880
tgacaggggg aatggcaagc aagtgggatc agaagggtat ggacattgcc tatgaggagg    8940
cggccttagg ttacaaagag ggtggtgttc ctattggcgg atgtcttatc aataacaaag    9000
acggaagtgt tctcggtcgt ggtcacaaca tgagatttca aaagggatcc gccacactac    9060
atggtgagat ctccactttg gaaaactgtg ggagattaga gggcaaagtg tacaaagata    9120
ccactttgta tacgacgctg tctccatgcg acatgtgtac aggtgccatc atcatgtatg    9180
gtattccacg ctgtgttgtc ggtgagaacg ttaatttcaa agtaagggc gagaaatatt      9240 tacaaactag aggtcacgag gttgttgttg ttgacgatga gaggtgtaaa aagatcatga     9300
aacaatttat cgatgaaaga cctcaggatt ggtttgaaga tattggtgag taggcggccg    9360
```

```
cagataaaat aaaagatttt atttagtctc cagaaaaagg ggggaatgaa agaccccacc    9420
tgtaggtttg gcaagctagc ttaagtaacg ccattttgca aggcatggaa aaatacataa    9480
ctgagaatag agaagttcag atcaaggtca ggaacagatg gaacagctga atatgggcca    9540
aacaggatat ctgtggtaag cagttcctgc cccggctcag ggccaagaac agatggaaca    9600
gctgaatatg ggccaaacag atatctgtg gtaagcagtt cctgcccgg ctcagggcca    9660 agaacagatg gtccccagat gcggtccagc cctcagcagt ttctagagaa ccatcagatg    9720
tttccagggt gccccaagga cctgaaatga ccctgtgcct tatttgaact aaccaatcag    9780
ttcgcttctc gcttctgttc gcgcgcttct gctccccgag ctcaataaaa gagcccacaa    9840
cccctcactc ggggcgccag tcctccgatt gactgagtcg cccgggtacc cgtgtatcca    9900
ataaaccctc ttgcagttgc atccgacttg tggtctcgct gttccttggg agggtctcct    9960
ctgagtgatt gactacccgt cagcggggt ctttcattac atgtgagcaa aaggccagca   10020
aaaggccagg aaccgtaaaa aggccgcgtt gctggcgttt ttccataggc tccgcccccc   10080
tgacgagcat cacaaaaatc gacgctcaag tcagaggtgg cgaaacccga caggactata   10140
aagataccag gcgttttccc ctggaagctc cctcgtgcgc tctcctgttc cgaccctgcc   10200
gcttaccgga tacctgtccg cctttctccc ttcgggaagc gtggcgcttt ctcaatgctc   10260
acgctgtagg tatctcagtt cggtgtaggt cgttcgctcc aagctgggct gtgtgcacga   10320
accccccgtt cagcccgacc gctgcgcctt atccggtaac tatcgtcttg agtccaaccc   10380
ggtaagacac gacttatcgc cactggcagc agccactggt aacaggatta gcagagcgag   10440
gtatgtaggc ggtgctacag agttcttgaa gtggtggcct aactacggct acactagaag   10500
gacagtattt ggtatctgcg ctctgctgaa gccagttacc ttcggaaaaa gagttggtag   10560
ctcttgatcc ggcaaacaaa ccaccgctgg tagcggtggt ttttttgttt gcaagcagca   10620
gattacgcgc agaaaaaaag gatctcaaga agatcctttg atcttttcta cggggtctga   10680
cgctcagtgg aacgaaaact cacgttaagg gattttggtc atgagattat caaaaaggat   10740
cttcacctag atccttttaa attaaaaatg aagttttaaa tcaatctaaa gtatatatga   10800
gtaaacttgg tctgacagtt accaatgctt aatcagtgag gcacctatct cagcgatctg   10860
tctatttcgt tcatccatag ttgcctgact ccccgtcgtg tagataacta cgatacggga   10920
gggcttacca tctggcccca gtgctgcaat gataccgcga gacccacgct caccggctcc   10980
agatttatca gcaataaacc agccagccgg aagggccgag cgcagaagtg gtcctgcaac   11040
tttatccgcc tccatccagt ctattaattg ttgccgggaa gctagagtaa gtagttcgcc   11100
agttaatagt ttgcgcaacg ttgttgccat tgctgcaggc atcgtggtgt cacgctcgtc   11160
gtttggtatg gcttcattca gctccggttc ccaacgatca aggcgagtta catgatcccc   11220
catgttgtgc aaaaaagcgg ttagctcctt cggtcctccg atcgttgtca gaagtaagtt   11280
ggccgcagtg ttatcactca tggttatggc agcactgcat aattctctta ctgtcatgcc   11340
atccgtaaga tgcttttctg tgactggtga gtactcaacc aagtcattct gagaatagtg   11400
tatgcggcga ccgagttgct cttgcccggc gtcaacacgg gataataccg cgccacatag   11460
cagaacttta aaagtgctca tcattggaaa acgttcttcg gggcgaaaac tctcaaggat   11520
cttaccgctg ttgagatcca gttcgatgta acccactcgt gcacccaact gatcttcagc   11580
atcttttact ttcaccagcg tttctgggtg agcaaaaaca ggaaggcaaa atgccgcaaa   11640
aaagggaata agggcgacac ggaaatgttg aatactcata ctcttccttt ttcaatatta   11700
ttgaagcatt tatcagggtt attgtctcat gagcggatac atatttgaat gtatttagaa   11760
```

-continued

```
aaataaacaa ataggggttc cgcgcacatt tccccgaaaa gtgccacctg acgtctaaga      11820
aaccattatt atcatgacat taacctataa aaataggcgt atcacgaggc cctttcgtct      11880
tcaagaattc at                                                          11892
```

<210> SEQ ID NO 3
<211> LENGTH: 11893
<212> TYPE: DNA
<213> ORGANISM: Artificial Sequence
<220> FEATURE:
<223> OTHER INFORMATION: pAC3-yCD2 recombinant vector

<400> SEQUENCE: 3

```
tagttattaa tagtaatcaa ttacggggtc attagttcat agcccatata tggagttccg        60
cgttacataa cttacggtaa atggcccgcc tggctgaccg cccaacgacc cccgcccatt       120
gacgtcaata atgacgtatg ttcccatagt aacgccaata gggactttcc attgacgtca       180
atgggtggag tatttacggt aaactgccca cttggcagta catcaagtgt atcatatgcc       240
aagtacgccc cctattgacg tcaatgacgg taaatggccc gcctggcatt atgcccagta       300
catgacctta tgggactttc ctacttggca gtacatctac gtattagtca tcgctattac       360
catggtgatg cggttttggc agtacatcaa tgggcgtgga tagcggtttg actcacgggg       420
atttccaagt ctccacccca ttgacgtcaa tgggagtttg ttttggcacc aaaatcaacg       480
ggactttcca aaatgtcgta acaactccgc cccattgacg caaatgggcg gtaggcgtgt       540
acggtgggag gtctatataa gcagagctgg tttagtgaac cggcgccagt cctccgattg       600
actgagtcgc ccgggtaccc gtgtatccaa taaaccctct tgcagttgca tccgacttgt       660
ggtctcgctg ttccttggga gggtctcctc tgagtgattg actacccgtc agcggggtc        720 tttcatttgg gggctcgtcc gggatcggga ccccctgcc  cagggaccac cgacccacca       780 ccggaggta agctgccag caacttatct gtgtctgtcc gattgtctag tgtctatgac          840
tgattttatg cgcctgcgtc ggtactagtt agctaactag ctctgtatct ggcggacccg       900
tggtggaact gacgagttcg gaacacccgg ccgcaaccct gggagacgtc ccagggactt       960
cgggggccgt ttttgtggcc cgacctgagt ccaaaaatcc cgatcgtttt ggactctttg      1020
gtgcaccccc cttagaggag ggatatgtgg ttctggtagg agacgagaac ctaaaacagt      1080
tcccgcctcc gtctgaattt ttgctttcgg tttgggaccg aagccgcgcc gcgcgtcttg      1140
tctgctgcag catcgttctg tgttgtctct gtctgactgt gtttctgtat tgtctgaaa       1200 atatgggcca gactgttacc actcccttaa gtttgacctt aggtcactgg aaagatgtcg      1260
agcggatcgc tcacaaccag tcggtagatg tcaagaagag acgttgggtt accttctgct      1320
ctgcagaatg gccaaccttt aacgtcggat ggccgcgaga cggcaccttt aaccgagacc      1380
tcatcaccca ggttaagatc aaggtctttt cacctggccc gcatggacac ccagaccagg      1440 tccctacat cgtgacctgg gaagccttgg cttttgaccc ctccctggg gtcaagccct          1500 ttgtacaccc taagcctccg cctcctcttc ctccatccgc cccgtctctc cccttgaac        1560 ctcctcgttc gaccccgcct cgatcctccc tttatccagc cctcactcct tctctaggcg      1620
ccaaacctaa acctcaagtt cttttctgaca gtgggggcc gctcatcgac ctacttacag      1680
aagacccccc gccttatagg gacccaagac cacccccttc cgacagggac ggaaatggtg      1740
gagaagcgac ccctgcggga gaggcaccgg accccctccc aatggcatct cgcctacgtg      1800
ggagacggga gcccctgtg  gccgactcca ctacctcgca ggcattcccc ctccgcgcag      1860
```

```
gaggaaacgg acagcttcaa tactggccgt tctcctcttc tgacctttac aactggaaaa    1920
ataataaccc ttcttttttct gaagatccag gtaaactgac agctctgatc gagtctgtcc    1980
tcatcaccca tcagcccacc tgggacgact gtcagcagct gttggggact ctgctgaccg    2040
gagaagaaaa acaacgggtg ctcttagagg ctagaaaggc ggtgcggggc gatgatgggc    2100
gccccactca actgcccaat gaagtcgatg ccgcttttcc cctcgagcgc ccagactggg    2160
attacaccac ccaggcaggt aggaaccacc tagtccacta tcgccagttg ctcctagcgg    2220
gtctccaaaa cgcgggcaga agccccacca atttggccaa ggtaaaagga ataacacaag    2280
ggcccaatga gtctccctcg gccttcctag agagacttaa ggaagcctat cgcaggtaca    2340
ctccttatga ccctgaggac ccagggcaag aaactaatgt gtctatgtct ttcatttggc    2400
agtctgcccc agacattggg agaaagttag agaggttaga gatttaaaa aacaagacgc    2460 ttggagattt ggttagagag gcagaaaaga tctttaataa cgagaaacc ccggaagaaa    2520 gagaggaacg tatcaggaga gaaacagagg aaaagaaga acgccgtagg acagaggatg    2580
agcagaaaga gaaagaaaga gatcgtagga gacatagaga gatgagcaag ctattggcca    2640
ctgtcgttag tggacagaaa caggatagaa agggaggaga acgaaggagg tcccaactcg    2700
atcgcgacca gtgtgcctac tgcaaagaaa aggggcactg ggctaaagat tgtcccaaga    2760
aaccacgagg acctcgggga ccaagacccc agacctccct cctgacccta gatgactagg    2820
gaggtcaggg tcaggagccc cccctgaac ccaggataac cctcaaagtc ggggggcaac    2880
ccgtcacctt cctggtagat actggggccc aacactccgt gctgacccaa atcctggac    2940 ccctaagtga taagtctgcc tgggtccaag gggctactgg aggaaagcgg tatcgctgga    3000
ccacggatcg caaagtacat ctagctaccg gtaaggtcac ccactctttc ctccatgtac    3060
cagactgtcc ctatcctctg ttaggaagag atttgctgac taaactaaaa gcccaaatcc    3120
actttgaggg atcaggagcc caggttatgg gaccaatggg gcagcccctg caagtgttga    3180
ccctaaatat agaagatgag tatcggctac atgagacctc aaaagagcca gatgtttctc    3240
tagggtccac atggctgtct gattttcctc aggcctgggc ggaaaccggg ggcatgggac    3300
tggcagttcg ccaagctcct ctgatcatac ctctgaaagc aacctctacc cccgtgtcca    3360
taaaacaata ccccatgtca caagaagcca gactgggat caagccccac atacagagac    3420
tgttggacca gggaatactg gtaccctgcc agtcccctg gaacacgccc ctgctacccg    3480
ttaagaaacc agggactaat gattataggc ctgtccagga tctgagagaa gtcaacaagc    3540
gggtggaaga catccacccc accgtgccca acccttacaa cctcttgagc gggctcccac    3600
cgtcccacca gtggtacact gtgcttgatt taaaggatgc cttttttctgc ctgagactcc    3660 accccaccag tcagcctctc ttcgcctttg agtggagaga tccagagatg ggaatctcag    3720
gacaattgac ctggaccaga ctcccacagg gtttcaaaaa cagtcccacc ctgtttgatg    3780
aggcactgca cagagaccta gcagacttcc ggatccagca cccagacttg atcctgctac    3840
agtacgtgga tgacttactg ctggccgcca cttctgagct agactgccaa caaggtactc    3900
gggccctgtt acaaacccta gggaacctcg gtatcgggc ctcggccaag aaagcccaaa    3960
tttgccagaa acaggtcaag tatctggggt atcttctaaa agagggtcag agatggctga    4020
ctgaggccag aaaagagact gtgatggggc agcctactcc gaagacccct cgacaactaa    4080
gggagttcct agggacggca ggcttctgtc gcctctggat ccctgggttt gcagaaatgg    4140 cagcccccett gtaccctctc accaaaaacgg ggactctgtt taattgggc ccagaccaac    4200 aaaaggccta tcaagaaatc aagcaagctc ttctaactgc cccagccctg gggttgccag    4260
```

```
atttgactaa gcccctttgaa ctctttgtcg acgagaagca gggctacgcc aaaggtgtcc    4320
taacgcaaaa actgggacct tggcgtcggc cggtggccta cctgtccaaa aagctagacc    4380
cagtagcagc tgggtggccc ccttgcctac ggatggtagc agccattgcc gtactgacaa    4440
aggatgcagg caagctaacc atgggacagc cactagtcat tctggccccc catgcagtag    4500
aggcactagt caaacaaccc cccgaccgct ggctttccaa cgcccggatg actcactatc    4560
aggccttgct tttggacacg gaccgggtcc agttcggacc ggtggtagcc ctgaacccgg    4620
ctacgctgct cccactgcct gaggaagggc tgcaacacaa ctgccttgat atcctggccg    4680
aagcccacgg aacccgaccc gacctaacgg accagccgct cccagacgcc gaccacacct    4740
ggtacacgga tggaagcagt ctcttacaag agggacagcg taaggcggga gctgcggtga    4800
ccaccgagac cgaggtaatc tgggctaaag ccctgccagc cgggacatcc gctcagcggg    4860
ctgaactgat agcactcacc caggccctaa agatggcaga aggtaagaag ctaaatgttt    4920
atactgatag ccgttatgct tttgctactg cccatatcca tggagaaata tacagaaggc    4980
gtgggttgct cacatcagaa ggcaaagaga tcaaaaataa agacgagatc ttggccctac    5040
taaaagccct ctttctgccc aaaagactta gcataatcca ttgtccagga catcaaaagg    5100
gacacagcgc cgaggctaga ggcaaccgga tggctgacca agcggcccga aaggcagcca    5160
tcacagagac tccagacacc tctaccctcc tcatagaaaa ttcatcaccc tacacctcag    5220
aacattttca ttacacagtg actgatataa aggacctaac caagttgggg gccatttatg    5280
ataaaacaaa gaagtattgg gtctaccaag gaaaacctgt gatgcctgac cagtttactt    5340
ttgaattatt agactttctt catcagctga ctcacctcag cttctcaaaa atgaaggctc    5400
tcctagagag aagccacagt ccctactaca tgctgaaccg ggatcgaaca ctcaaaaata    5460
tcactgagac ctgcaaagct tgtgcacaag tcaacgccag caagtctgcc gttaaacagg    5520
gaactagggt ccgcgggcat cggcccggca ctcattggga gatcgatttc accgagataa    5580
agcccggatt gtatggctat aaatatcttc tagtttttat agataccttt tctggctgga    5640
tagaagcctt cccaaccaag aaagaaaccg ccaaggtcgt aaccaagaag ctactagagg    5700
agatcttccc caggttcggc atgcctcagg tattgggaac tgacaatggg cctgccttcg    5760
tctccaaggt gagtcagaca gtggccgatc tgttggggat tgattggaaa ttacattgtg    5820
catacagacc ccaaagctca ggccaggtag aaagaatgaa tagaaccatc aaggagactt    5880
taactaaatt aacgcttgca actggctcta gagactgggt gctcctactc cccttagccc    5940
tgtaccgagc ccgcaacacg ccgggccccc atggcctcac cccatatgag atcttatatg    6000
gggcaccccc gccccttgta aacttccctg accctgacat gacaagagtt actaacagcc    6060
cctctctcca agctcactta caggctctct acttagtcca gcacgaagtc tggagacctc    6120
tggcggcagc ctaccaagaa caactggacc gaccggtggt acctcaccct taccgagtcg    6180
gcgacacagt gtgggtccgc cgacaccaga ctaagaacct agaacctcgc tggaaaggac    6240
cttacacagt cctgctgacc acccccaccg ccctcaaagt agacggcatc gcagcttgga    6300
tacacgccgc ccacgtgaag gctgccgacc ccggggggtgg accatcctct agactgacat    6360
ggcgcgttca acgtctctcaa aaccccctca agataagatt aacccgtgga agcccttaat    6420
agtcatggga gtcctgttag gagtagggat ggcagagagc cccatcagg tctttaatgt    6480 aacctggaga gtcaccaacc tgatgactgg gcgtaccgcc aatgccacct ccctcctggg    6540
aactgtacaa gatgccttcc caaaattata ttttgatcta tgtgatctgg tcggagagga    6600
```

```
gtgggaccct tcagaccagg aaccgtatgt cgggtatggc tgcaagtacc ccgcagggag    6660
acagcggacc cggacttttg acttttacgt gtgccctggg cataccgtaa agtcggggtg    6720
tgggggacca ggagagggct actgtggtaa atggggtgt gaaaccaccg acaggctta    6780 ctggaagccc acatcatcgt gggacctaat ctcccttaag cgcggtaaca ccccctggga    6840
cacgggatgc tctaaagttg cctgtggccc ctgctacgac ctctccaaag tatccaattc    6900
cttccaaggg gctactcgag ggggcagatg caaccctcta gtcctagaat tcactgatgc    6960
aggaaaaaag gctaactggg acgggcccaa atcgtgggga ctgagactgt accggacagg    7020
aacagatcct attaccatgt tctccctgac ccggcaggtc cttaatgtgg accccgagt    7080 ccccataggg cccaacccag tattacccga ccaaagactc ccttcctcac caatagagat    7140
tgtaccggct ccacagccac ctagccccct caataccagt tacccccctt ccactaccag    7200
tacaccctca acctccccta caagtccaag tgtcccacag ccaccccag gaactggaga    7260 tagactacta gctctagtca aaggagccta tcaggcgctt aacctcacca atcccgacaa    7320
gacccaagaa tgttggctgt gcttagtgtc gggacctcct tattacgaag gagtagcggt    7380
cgtgggcact tataccaatc attccaccgc tccggccaac tgtacggcca cttcccaaca    7440
taagcttacc ctatctgaag tgacaggaca gggcctatgc atggggggcag tacctaaaac    7500 tcaccaggcc ttatgtaaca ccacccaaag cgccggctca ggatcctact accttgcagc    7560
acccgccgga acaatgtggg cttgcagcac tggattgact ccctgcttgt ccaccacggt    7620
gctcaatcta accacagatt attgtgtatt agttgaactc tggcccagag taatttacca    7680
ctcccccgat tatatgtatg gtcagcttga acagcgtacc aaatataaaa gagagccagt    7740
atcattgacc ctggcccttc tactaggagg attaaccatg ggagggattg cagctggaat    7800
agggacgggg accactgcct taattaaaac ccagcagttt gagcagcttc atgccgctat    7860
ccagacagac ctcaacgaag tcgaaaagtc aattaccaac ctagaaaagt cactgacctc    7920
gttgtctgaa gtagtcctac agaaccgcag aggcctagat tgctattcc taaaggaggg    7980 aggtctctgc gcagccctaa agaagaatg ttgtttttat gcagaccaca cggggctagt    8040
gagagacagc atggccaaat taagagaaag gcttaatcag agacaaaaac tatttgagac    8100
aggccaagga tggttcgaag ggctgtttaa tagatccccc tggtttacca ccttaatctc    8160
caccatcatg ggacctctaa tagtactctt actgatctta ctctttggac cttgcattct    8220
caatcgattg gtccaatttg ttaaagacag gatctcagtg gtccaggctc tggttttgac    8280
tcagcaatat caccagctaa aacccataga gtacgagcca tgaacgcgtt actggccgaa    8340
gccgcttgga ataaggccgg tgtgcgtttg tctatatgtt attttccacc atattgccgt    8400
cttttggcaa tgtgagggcc cggaaacctg gccctgtctt cttgacgagc attcctaggg    8460
gtctttcccc tctcgccaaa ggaatgcaag gtctgttgaa tgtcgtgaag gaagcagttc    8520
ctctggaagc ttcttgaaga caaacaacgt ctgtagcgac cctttgcagg cagcggaacc    8580
ccccacctgg cgacaggtgc ctctgcggcc aaaagccacg tgtataagat acacctgcaa    8640
aggcggcaca accccagtgc cacgttgtga gttggatagt tgtggaaaga gtcaaatggc    8700
tctcctcaag cgtattcaac aaggggctga aggatgccca gaaggtaccc cattgtatgg    8760
gatctgatct ggggcctcgg tgcacatgct ttacatgtgt ttagtcgagg ttaaaaaaac    8820
gtctaggccc cccgaaccac ggggacgtgg ttttcctttg aaaaacacga ttataaatgg    8880
tgaccggcgc catggcctcc aagtgggatc aaaagggcat ggatatcgct tacgaggagg    8940
ccctgctggg ctacaaggag ggcggcgtgc ctatcggcgg ctgtctgatc aacaacaagg    9000
```

```
acggcagtgt gctgggcagg ggccacaaca tgaggttcca gaagggctcc gccaccctgc   9060
acggcgagat ctccaccctg gagaactgtg gcaggctgga gggcaaggtg tacaaggaca   9120
ccacgctgta caccaccctg tccccttgtg acatgtgtac cggcgctatc atcatgtacg   9180
gcatccctag gtgtgtgatc ggcgagaacg tgaacttcaa gtccaagggc gagaagtacc   9240
tgcaaaccag ggggccacgag gtggtggttg ttgacgatga gaggtgtaag aagctgatga   9300
agcagttcat cgacgagagg cctcaggact ggttcgagga tatcggcgag taagcggccg   9360
cagataaaat aaaagatttt atttagtctc cagaaaaagg gggaatgaa agaccccacc    9420
tgtaggtttg gcaagctagc ttaagtaacg ccatttttgca aggcatggaa aaatacataa   9480
ctgagaatag agaagttcag atcaaggtca ggaacagatg aacagctga atatgggcca   9540
aacaggatat ctgtggtaag cagttcctgc cccggctcag ggccaagaac agatggaaca   9600
gctgaatatg gccaaacag gatatctgtg gtaagcagtt cctgccccgg ctcagggcca   9660
agaacagatg gtccccagat gcggtccagc cctcagcagt ttctagagaa ccatcagatg   9720
tttccagggt gccccaagga cctgaaatga ccctgtgcct tatttgaact aaccaatcag   9780
ttcgcttctc gcttctgttc gcgcgcttct gctccccgag ctcaataaaa gagcccacaa   9840
cccctcactc ggggcgccag tcctccgatt gactgagtcg cccgggtacc cgtgtatcca   9900
ataaaccctc ttgcagttgc atccgacttg tggtctcgct gttccttggg agggtctcct   9960
ctgagtgatt gactacccgt cagcgggggt ctttcattac atgtgagcaa aaggccagca  10020
aaaggccagg aaccgtaaaa aggccgcgtt gctggcgttt ttccataggc tccgcccccc  10080
tgacgagcat cacaaaaatc gacgctcaag tcagaggtgg cgaaacccga caggactata  10140
aagataccag gcgtttcccc ctggaagctc cctcgtgcgc tctcctgttc cgaccctgcc  10200
gcttaccgga tacctgtccg cctttctccc ttcgggaagc gtggcgcttt ctcatagctc  10260
acgctgtagg tatctcagtt cggtgtaggt cgttcgctcc aagctgggct gtgtgcacga  10320
acccccccgtt cagcccgacc gctgcgcctt atccggtaac tatcgtcttg agtccaaccc  10380
ggtaagacac gacttatcgc cactggcagc agccactggt aacaggatta gcagagcgag  10440
gtatgtaggc ggtgctacag agttcttgaa gtggtggcct aactacggct acactagaag  10500
gacagtattt ggtatctgcg ctctgctgaa gccagttacc ttcggaaaaa gagttggtag  10560
ctcttgatcc ggcaaacaaa ccaccgctgg tagcggtggt ttttttgttt gcaagcagca  10620
gattacgcgc agaaaaaaag gatctcaaga agatcctttg atcttttcta cggggtctga  10680
cgctcagtgg aacgaaaact cacgttaagg gattttggtc atgagattat caaaaaggat  10740
cttcacctag atccttttaa attaaaaatg aagttttaaa tcaatctaaa gtatatatga  10800
gtaaacttgg tctgacagtt accaatgctt aatcagtgag gcacctatct cagcgatctg  10860
tctatttcgt tcatccatag ttgcctgact ccccgtcgtg tagataacta cgatacggga  10920
gggcttacca tctggcccca gtgctgcaat gataccgcga gacccacgct caccggctcc  10980
agatttatca gcaataaacc agccagccgg aagggccgag cgcagaagtg gtcctgcaac  11040
tttatccgcc tccatccagt ctattaattg ttgccgggaa gctagagtaa gtagttcgcc  11100
agttaatagt ttgcgcaacg ttgttgccat tgctgcaggc atcgtggtgt cacgctcgtc  11160
gtttggtatg gcttcattca gctccggttc ccaacgatca aggcgagtta catgatcccc  11220
catgttgtgc aaaaaagcgg ttagctcctt cggtcctccg atcgttgtca gaagtaagtt  11280
ggccgcagtg ttatcactca tggttatggc agcactgcat aattctctta ctgtcatgcc  11340
```

| | |
|---|---:|
| atccgtaaga tgcttttctg tgactggtga gtactcaacc aagtcattct gagaatagtg | 11400 |
| tatgcggcga ccgagttgct cttgcccggc gtcaacacgg gataataccg cgccacatag | 11460 |
| cagaacttta aaagtgctca tcattggaaa acgttcttcg gggcgaaaac tctcaaggat | 11520 |
| cttaccgctg ttgagatcca gttcgatgta acccactcgt gcacccaact gatcttcagc | 11580 |
| atcttttact ttcaccagcg tttctgggtg agcaaaaaca ggaaggcaaa atgccgcaaa | 11640 |
| aaagggaata aggcgacac ggaaatgttg aatactcata ctcttccttt ttcaatatta | 11700 |
| ttgaagcatt tatcagggtt attgtctcat gagcggatac atatttgaat gtatttagaa | 11760 |
| aaataaacaa ataggggttc cgcgcacatt tccccgaaaa gtgccacctg acgtctaaga | 11820 |
| aaccattatt atcatgacat taacctataa aaataggcgt atcacgaggc cctttcgtct | 11880 |
| tcaagaattc cat | 11893 |

<210> SEQ ID NO 4
<211> LENGTH: 12007
<212> TYPE: DNA
<213> ORGANISM: Artificial Sequence
<220> FEATURE:
<223> OTHER INFORMATION: RCR Vector - pACE-CD

<400> SEQUENCE: 4

| | |
|---|---:|
| tagttattaa tagtaatcaa ttacggggtc attagttcat agcccatata tggagttccg | 60 |
| cgttacataa cttacggtaa atggcccgcc tggctgaccg cccaacgacc cccgcccatt | 120 |
| gacgtcaata atgacgtatg ttcccatagt aacgccaata gggactttcc attgacgtca | 180 |
| atgggtggag tatttacggt aaactgccca cttggcagta catcaagtgt atcatatgcc | 240 |
| aagtacgccc cctattgacg tcaatgacgg taaatggccc gcctggcatt atgcccagta | 300 |
| catgacctta tgggactttc ctacttggca gtacatctac gtattagtca tcgctattac | 360 |
| catggtgatg cggttttggc agtacatcaa tgggcgtgga tagcggtttg actcacgggg | 420 |
| atttccaagt ctccacccca ttgacgtcaa tgggagtttg ttttggcacc aaaatcaacg | 480 |
| ggactttcca aaatgtcgta caactccgcc ccattgacg caaatgggcg gtaggcgtgt | 540 |
| acggtgggag gtctatataa gcagagctgg tttagtgaac cggcgccagt cctccgattg | 600 |
| actgagtcgc ccgggtaccc gtgtatccaa taaaccctct tgcagttgca tccgacttgt | 660 |
| ggtctcgctg ttccttggga gggtctcctc tgagtgattg actacccgtc agcggggtc | 720 |
| tttcatttgg ggctcgtcc gggatcggga gacccctgcc cagggaccac cgacccacca | 780 |
| ccggaggta agctggccag caacttatct gtgtctgtcc gattgtctag tgtctatgac | 840 |
| tgatttatg cgcctgcgtc ggtactagtt agctaactag ctctgtatct ggcggacccg | 900 |
| tggtggaact gacgagttcg gaacacccgg ccgcaaccct gggagacgtc cagggactt | 960 |
| cgggggccgt ttttgtggcc cgacctgagt ccaaaaatcc cgatcgtttt ggactctttg | 1020 |
| gtgcacccccc cttagaggag ggatatgtgg ttctggtagg agacgagaac ctaaaacagt | 1080 |
| tcccgcctcc gtctgaattt ttgctttcgg tttgggaccg aagccgcgcc gcgcgtcttg | 1140 |
| tctgctgcag catcgttctg tgttgtctct gtctgactgt gtttctgtat ttgtctgaga | 1200 |
| atatgggcca gactgttacc actcccttaa gtttgacctt aggtcactgg aaagatgtcg | 1260 |
| agcggatcgc tcacaaccag tcggtagatg tcaagaagag acgttgggtt accttctgct | 1320 |
| ctgcagaatg gccaaccttt aacgtcggat ggccgcgaga cggcacccttt aaccgagacc | 1380 |
| tcatcaccca ggttaagatc aaggtctttt cacctggccc gcatggacac ccagaccagg | 1440 |
| tcccctacat cgtgacctgg gaagccttgg ctttgacccc cctccctgg gtcaagccct | 1500 |

```
ttgtacaccc taagcctccg cctcctcttc ctccatccgc cccgtctctc cccct tgaac    1560 ctcctcgttc gaccccgcct cgatcctccc tttatccagc cctcactcct tctctaggcg    1620
ccaaacctaa acctcaagtt ctttctgaca gtgggggggcc gctcatcgac ctacttacag    1680
aagacccccc gccttatagg gacccaagac caccccct tc cgacagggac ggaaatggtg    1740
gagaagcgac ccctgcggga gaggcaccgg acccctcccc aatggcatct cgcctacgtg    1800
ggagacggga gcccctgtg ccgactcca ctacctcgca ggcattcccc ctccgcgcag      1860
gaggaaacgg acagcttcaa tactggccgt tctcctcttc tgacctttac aactggaaaa    1920
ataataaccc ttctttttct gaagatccag gtaaactgac agctctgatc gagtctgttc    1980
tcatcaccca tcagcccacc tggacgact gtcagcagct gttggggact ctgctgaccg     2040
gagaagaaaa acaacggtgt ctcttagagg ctagaaaggc ggtgcggggc gatgatgggc    2100
gccccactca actgcccaat gaagtcgatg ccgcttttcc cctcgagcgc ccagactggg    2160
attacaccac ccaggcaggt aggaaccacc tagtccacta tcgccagttg ctcctagcgg    2220
gtctccaaaa cgcgggcaga agccccacca atttggccaa ggtaaaagga ataacacaag    2280
ggcccaatga gtctccctcg gccttcctag agagacttaa ggaagcctat cgcaggtaca    2340
ctccttatga ccctgaggac ccagggcaag aaactaatgt gtctatgtct ttcatttggc    2400
agtctgcccc agacattggg agaaagttag agaggttaga gatttaaaa aacaagacgc     2460 ttggagattt ggttagagag gcagaaaaga tctttaataa acgagaaacc ccggaagaaa    2520
gagaggaacg tatcaggaga gaaacagagg aaaaagaaga acgccgtagg acagaggatg    2580
agcagaaaga gaaagaaaga gatcgtagga gacatagaga gatgagcaag ctattggcca    2640
ctgtcgttag tggacagaaa caggatagac agggaggaga acgaaggagg tcccaactcg    2700
atcgcgacca gtgtgcctac tgcaaagaaa agggggcactg ggctaaagat tgtcccaaga   2760
aaccacgagg acctcgggga ccaagacccc agacctccct cctgacccta gatgactagg    2820
gaggtcaggg tcaggagccc cccctgaac ccaggataac cctcaaagtc gggggggcaac    2880 ccgtcacctt cctggtagat actggggccc aacactccgt gctgacccaa aatcctggac    2940
ccctaagtga taagtctgcc tgggtccaag gggctactgg aggaaagcgg tatcgctgga    3000
ccacggatcg caaagtacat ctagctaccg gtaaggtcac ccactctttc ctccatgtac    3060
cagactgtcc ctatcctctg ttaggaagag atttgctgac taaactaaaa gcccaaatcc    3120
actttgaggg atcaggagcc caggttatgg gaccaatggg gcagcccctg caagtgttga    3180
ccctaaatat agaagatgag catcggctac atgagacctc aaaagagcca gatgtttctc    3240
tagggtccac atggctgtct gattttcctc aggcctgggc ggaaaccggg ggcatgggac    3300
tggcagttcg ccaagctcct ctgatcatac ctctgaaagc aacctctacc cccgtgtcca    3360
taaaacaata ccccatgtca caagaagcca gactggggat caagccccac atacagagac    3420
tgttggacca gggaatactg gtaccctgcc agtcccctg gaacacgccc ctgctacccg     3480
ttaagaaacc agggactaat gattataggc ctgtccagga tctgagagaa gtcaacaagc    3540
gggtggaaga catccacccc accgtgccca accttacaa cctcttgagc gggctcccac     3600
cgtcccacca gtggtacact gtgctt gatt taaaggatgc cttttctgc ctgagactcc    3660 accccaccag tcagcctctc ttcgcctttg agtggagaga tccagagatg ggaatctcag    3720
gacaattgac ctggaccaga ctcccacagg gtttcaaaaa cagtcccacc ctgtttgatg    3780
aggcactgca cagagaccta gcagacttcc ggatccagca cccagacttg atcctgctac    3840
```

```
agtacgtgga tgacttactg ctggccgcca cttctgagct agactgccaa caaggtactc    3900
gggccctgtt acaaaccct a gggaacctcg ggtatcgggc ctcggccaag aaagcccaaa    3960
tttgccagaa acaggtcaag tatctggggt atcttctaaa agagggtcag agatggctga    4020
ctgaggccag aaaagagact gtgatggggc agcctactcc gaagacccct cgacaactaa    4080
gggagttcct agggacggca ggcttctgtc gcctctggat ccctgggttt gcagaaatgg    4140 cagcccctt gtaccctctc accaaaacgg ggactctgtt taattggggc ccagaccaac    4200
aaaaggccta tcaagaaatc aagcaagctc ttctaactgc cccagccctg gggttgccag    4260
atttgactaa gcccttgaa ctctttgtcg acgagaagca gggctacgcc aaaggtgtcc    4320
taacgcaaaa actgggacct tggcgtcggc cggtggccta cctgtccaaa aagctagacc    4380
cagtagcagc tgggtggccc ccttgcctac ggatggtagc agccattgcc gtactgacaa    4440
aggatgcagg caagctaacc atgggacagc cactagtcat tctggcccc catgcagtag    4500 aggcactagt caaacaaccc cccgaccgct ggctttccaa cgcccggatg actcactatc    4560
aggccttgct tttggacacg gaccgggtcc agttcggacc ggtggtagcc ctgaacccgg    4620
ctacgctgct cccactgcct gaggaagggc tgcaacacaa ctgccttgat atcctggccg    4680
aagcccacgg aacccgaccc gacctaacgg accagccgct cccagacgcc gaccacacct    4740
ggtacacgga tggaagcagt ctcttacaag agggacagcg taaggcggga gctgcggtga    4800
ccaccgagac cgaggtaatc tgggctaaag ccctgccagc cgggacatcc gctcagcggg    4860
ctgaactgat agcactcacc caggccctaa agatggcaga aggtaagaag ctaaatgttt    4920
atactgatag ccgttatgct tttgctactg cccatatcca tggagaaata tacagaaggc    4980
gtgggttgct cacatcagaa ggcaaagaga tcaaaaataa agacgagatc ttggccctac    5040 taaaagcccct ctttctgccc aaaagactta gcataatcca ttgtccagga catcaaaagg    5100
gacacagcgc cgaggctaga ggcaaccgga tggctgacca agcggcccga aaggcagcca    5160
tcacagagac tccagacacc tctaccctcc tcatagaaaa ttcatcaccc tacacctcag    5220
aacattttca ttacacagtg actgatataa aggacctaac caagttgggg gccatttatg    5280
ataaaacaaa gaagtattgg gtctaccaag gaaaacctgt gatgcctgac cagttttactt    5340 ttgaattatt agactttctt catcagctga ctcacctcag cttctcaaaa atgaaggctc    5400
tcctagagag aagccacagt ccctactaca tgctgaaccg ggatcgaaca ctcaaaaata    5460
tcactgagac ctgcaaagct tgtgcacaag tcaacgccag caagtctgcc gttaaacagg    5520
gaactagggt ccgcgggcat cggcccggca ctcattggga gatcgatttc accgagataa    5580 agccccggatt gtatggctat aaatatcttc tagtttttat agatacccttt tctggctgga    5640 tagaagcctt cccaaccaag aaagaaaccg ccaaggtcgt aaccaagaag ctactagagg    5700
agatcttccc caggttcggc atgcctcagg tattgggaac tgacaatggg cctgccttcg    5760
tctccaaggt gagtcagaca gtggccgatc tgttggggat tgattggaaa ttacattgtg    5820
catacagacc ccaaagctca ggccaggtag aaagaatgaa tagaaccatc aaggagactt    5880
taactaaatt aacgcttgca actggctcta gagactgggt gctcctactc cccttagccc    5940
tgtaccgagc ccgcaacacg ccgggcccccc atggcctcac cccatatgag atcttatatg    6000 gggcacccc gcccttgta aacttccctg accctgacat gacaagagtt actaacagcc    6060
cctctctcca agctcactta caggctctct acttagtcca gcacgaagtc tggagacctc    6120
tggcggcagc ctaccaagaa caactggacc gaccggtggt acctcaccct taccgagtcg    6180
gcgacacagt gtgggtccgc cgacaccaga ctaagaacct agaacctcgc tggaaaggac    6240
```

```
cttacacagt cctgctgacc acccccaccg ccctcaaagt agacggcatc gcagcttgga    6300
tacacgccgc ccacgtgaag gctgccgacc ccggggtgg accatcctct agactgacat    6360
ggcgcgttca acgctctcaa aaccccctca agataagatt aacccgtgga agcccttaat    6420
agtcatggga gtcctgttag gagtagggat ggcagagagc ccccatcagg tctttaatgt    6480
aacctggaga gtcaccaacc tgatgactgg gcgtaccgcc aatgccacct ccctcctggg    6540
aactgtacaa gatgccttcc caaaattata ttttgatcta tgtgatctgg tcggagagga    6600
gtgggaccct tcagaccagg aaccgtatgt cgggtatggc tgcaagtacc ccgcagggag    6660
acagcggacc cggactttg actttttacgt gtgccctggg cataccgtaa agtcggggtg    6720
tgggggacca ggagagggct actgtggtaa atgggggtgt gaaaccaccg gacaggctta    6780
ctggaagccc acatcatcgt gggacctaat ctcccttaag cgcggtaaca cccccctggga    6840 cacgggatgc tctaaagttg cctgtggccc ctgctacgac ctctccaaag tatccaattc    6900
cttccaaggg gctactcgag ggggcagatg caaccctcta gtcctagaat tcactgatgc    6960
aggaaaaaag gctaactggg acgggcccaa atcgtgggga ctgagactgt accggacagg    7020
aacagatcct attaccatgt tctccctgac ccggcaggtc cttaatgtgg accccgagt    7080 ccccataggg cccaacccag tattacccga ccaaagactc ccttcctcac caatagagat    7140
tgtaccggct ccacagccac ctagcccccct caataccagt tacccccctt ccactaccag    7200
tacaccctca acctccccta caagtccaag tgtcccacag ccaccccag gaactggaga    7260 tagactacta gctctagtca aaggagccta tcaggcgctt aacctcacca atcccgacaa    7320
gacccaagaa tgttggctgt gcttagtgtc gggacctcct tattacgaag gagtagcggt    7380
cgtgggcact tataccaatc attccaccgc tccggccaac tgtacggcca cttcccaaca    7440
taagcttacc ctatctgaag tgacaggaca gggcctatgc atggggcag tacctaaaac    7500 tcaccaggcc ttatgtaaca ccacccaaag cgccggctca ggatcctact accttgcagc    7560
acccgccgga acaatgtggg cttgcagcac tggattgact ccctgcttgt ccaccacggt    7620
gctcaatcta accacagatt attgtgtatt agttgaactc tggcccagag taatttacca    7680 ctccccgat tatatgtatg gtcagcttga acagcgtacc aaatataaaa gagagccagt    7740
atcattgacc ctggcccttc tactaggagg attaaccatg ggagggattg cagctggaat    7800
agggacgggg accactgcct taattaaaaac ccagcagttt gagcagcttc atgccgctat    7860
ccagacagac ctcaacgaag tcgaaaagtc aattaccaac ctagaaaagt cactgacctc    7920
gttgtctgaa gtagtcctac agaaccgcag aggcctagat tgctattcc taaaggaggg    7980 aggtctctgc gcagccctaa agaagaatg ttgttttat gcagaccaca cggggctagt    8040
gagagacagc atggccaaat taagagaag gcttaatcag agacaaaaac tatttgagac    8100
aggccaagga tggttcgaag ggctgtttaa tagatccccc tggtttacca ccttaatctc    8160
caccatcatg ggacctctaa tagtactctt actgatctta ctctttggac ttgcattct    8220 caatcgatta gtccaatttg ttaaagacag gatatcagtg gtccaggctc tagttttgac    8280
tcaacaatat caccagctga agcctataga gtacgagcca tgacgtacgt tactggccga    8340
agccgcttgg aataaggccg gtgtgcgttt gtctatatgt tatttccac catattgccg    8400 tcttttggca atgtgagggc ccggaaacct ggccctgtct tcttgacgag cattcctagg    8460
ggtctttccc ctctcgccaa aggaatgcaa ggtctgttga atgtcgtgaa ggaagcagtt    8520
cctctggaag cttcttgaag acaaacaacg tctgtagcga cccctttgcag gcagcggaac    8580
```

```
cccccacctg gcgacaggtg cctctgcggc caaaagccac gtgtataaga tacacctgca   8640
aaggcggcac aacccccagtg ccacgttgtg agttggatag ttgtggaaag agtcaaatgg   8700
ctctcctcaa gcgtattcaa caaggggctg aaggatgccc agaaggtacc ccattgtatg   8760
ggatctgatc tggggcctcg gtgcacatgc tttacatgtg tttagtcgag gttaaaaaaa   8820
cgtctaggcc ccccgaacca cggggacgtg gttttccttt gaaaaacacg ataataccat   8880
ggtgacaggg ggaatggcaa gcaagtggga tcagaagggt atggacattg cctatgagga   8940
ggcggcctta ggttacaaag agggtggtgt tcctattggc ggatgtctta tcaataacaa   9000
agacggaagt gttctcggtc gtggtcacaa catgagattt caaaagggat ccgccacact   9060
acatggtgag atctccactt tggaaaactg tgggagatta gagggcaaag tgtacaaaga   9120
taccactttg tatacgacgc tgtctccatg cgacatgtgt acaggtgcca tcatcatgta   9180
tggtattcca cgctgtgttg tcggtgagaa cgttaatttc aaaagtaagg gcgagaaata   9240
tttacaaact agaggtcacg aggttgttgt tgttgacgat gagaggtgta aaagatcat    9300 gaaacaattt atcgatgaaa gacctcagga ttggttttgaa gatattggtg agtaggcggc   9360
cgcgccatag ataaaataaa agatttttatt tagtctccag aaaaaggggg gaatgaaaga   9420
ccccacctgt aggtttggca agctagctta agtaacgcca ttttgcaagg catggaaaaa   9480
tacataactg agaatagaga agttcagatc aaggtcagga acagatggaa cagctgaata   9540
tgggccaaac aggatatctg tggtaagcag ttcctgcccc ggctcagggc caagaacaga   9600
tggaacagct gaatatgggc caaacaggat atctgtggta agcagttcct gccccggctc   9660
agggccaaga acagatggtc cccagatgcg gtccagccct cagcagtttc tagagaacca   9720
tcagatgttt ccagggtgcc ccaaggacct gaaatgaccc tgtgccttgt ttaaactaac   9780
caatcagttc gcttctcgct tctgttcgcg cgcttctgct ccccgagctc aataaaagag   9840
cccacaaccc ctcactcggg gcgccagtcc tccgattgac tgagtcgccc gggtacccgt   9900
gtatccaata aaccctcttg cagttgcatc cgacttgtgg tctcgctgtt ccttgggagg   9960
gtctcctctg agtgattgac tacccgtcag cgggggtctt tcatttgggg gctcgtccgg  10020
gatcgggaga cccctgccca gggaccaccg acccaccacc gggaggtaag ctggctgcct  10080
cgcgcgtttc ggtgatgacg gtgaaaacct ctgacatgtg agcaaaaggc cagcaaaagg  10140
ccaggaaccg taaaaaggcc gcgttgctgg cgttttttcca taggctccgc ccccctgacg  10200
agcatcacaa aaatcgacgc tcaagtcaga ggtggcgaaa cccgacagga ctataaagat  10260
accaggcgtt ccccctgga agctccctcg tgcgctctcc tgttccgacc ctgccgctta  10320
ccggatacct gtccgccttt ctcccttcgg gaagcgtggc gctttctcaa tgctcacgct  10380
gtaggtatct cagttcggtg taggtcgttc gctccaagct gggctgtgtg cacgaacccc  10440
ccgttcagcc cgaccgctgc gccttatccg gtaactatcg tcttgagtcc aacccggtaa  10500
gacacgactt atcgccactg gcagcagcca ctggtaacag gattagcaga gcgaggtatg  10560
taggcggtgc tacagagttc ttgaagtggt ggcctaacta cggctacact agaaggacag  10620
tatttggtat ctgcgctctg ctgaagccag ttaccttcgg aaaaagagtt ggtagctctt  10680
gatccggcaa acaaaccacc gctggtagcg gtggtttttt tgtttgcaag cagcagatta  10740
cgcgcagaaa aaaggatctc aagaagatc ctttgatctt ttctacgggg tctgacgctc   10800
agtggaacga aaactcacgt taagggattt tggtcatgag attatcaaaa aggatcttca  10860
cctagatcct tttaaattaa aaatgaagtt ttaaatcaat ctaaagtata tatgagtaaa  10920
cttggtctga cagttaccaa tgcttaatca gtgaggcacc tatctcagcg atctgtctat  10980
```

-continued

```
ttcgttcatc catagttgcc tgactccccg tcgtgtagat aactacgata cgggagggct    11040
taccatctgg ccccagtgct gcaatgatac cgcgagaccc acgctcaccg gctccagatt    11100
tatcagcaat aaaccagcca gccggaaggg ccgagcgcag aagtggtcct gcaactttat    11160
ccgcctccat ccagtctatt aattgttgcc gggaagctag agtaagtagt tcgccagtta    11220
atagtttgcg caacgttgtt gccattgctg caggcatcgt ggtgtcacgc tcgtcgtttg    11280
gtatggcttc attcagctcc ggttcccaac gatcaaggcg agttacatga tcccccatgt    11340
tgtgcaaaaa agcggttagc tccttcggtc ctccgatcgt tgtcagaagt aagttggccg    11400
cagtgttatc actcatggtt atggcagcac tgcataattc tcttactgtc atgccatccg    11460
taagatgctt ttctgtgact ggtgagtact caaccaagtc attctgagaa tagtgtatgc    11520
ggcgaccgag ttgctcttgc ccggcgtcaa cacgggataa taccgcgcca catagcagaa    11580
ctttaaaagt gctcatcatt ggaaaacgtt cttcggggcg aaaactctca aggatcttac    11640
cgctgttgag atccagttcg atgtaaccca ctcgtgcacc caactgatct tcagcatctt    11700
ttactttcac cagcgtttct gggtgagcaa aaacaggaag gcaaaatgcc gcaaaaaagg    11760
gaataagggc gacacggaaa tgttgaatac tcatactctt ccttttcaa tattattgaa     11820 gcatttatca gggttattgt ctcatgagcg gatacatatt tgaatgtatt tagaaaaata    11880
aacaaatagg ggttccgcgc acatttcccc gaaaagtgcc acctgacgtc taagaaacca    11940
ttattatcat gacattaacc tataaaaata ggcgtatcac gaggcccttt cgtcttcaag    12000
aattcat                                                              12007
```